(12) United States Patent
El Harrak et al.

(10) Patent No.: US 10,520,500 B2
(45) Date of Patent: Dec. 31, 2019

(54) LABELLED SILICA-BASED NANOMATERIAL WITH ENHANCED PROPERTIES AND USES THEREOF

(76) Inventors: Abdeslam El Harrak, Bischheim (FR); Victoire Goust, Strasbourg (FR); Andrew David Griffiths, Strasbourg (FR); Thomas Mangeat, Strasbourg (FR)

( * ) Notice: Subject to any disclaimer, the term of this patent is extended or adjusted under 35 U.S.C. 154(b) by 967 days.

(21) Appl. No.: 13/500,813

(22) PCT Filed: Oct. 11, 2010

(86) PCT No.: PCT/EP2010/065188
§ 371 (c)(1),
(2), (4) Date: Nov. 27, 2012

(87) PCT Pub. No.: WO2011/042564
PCT Pub. Date: Apr. 14, 2011

(65) Prior Publication Data
US 2013/0064776 A1 Mar. 14, 2013

Related U.S. Application Data

(60) Provisional application No. 61/250,247, filed on Oct. 9, 2009.

(51) Int. Cl.
| | |
|---|---|
| *A61B 10/00* | (2006.01) |
| *A61B 8/00* | (2006.01) |
| *A61B 5/00* | (2006.01) |
| *G01N 33/543* | (2006.01) |
| *G01N 33/552* | (2006.01) |
| *G01N 33/58* | (2006.01) |

(52) U.S. Cl.
CPC ..... *G01N 33/54346* (2013.01); *G01N 33/552* (2013.01); *G01N 33/582* (2013.01); *Y10T 428/2993* (2015.01)

(58) Field of Classification Search
CPC ............... A61K 51/00; A61K 51/1217; A61K 51/1241; A61K 51/12; A61K 51/1244; A61K 51/1248; A61K 51/1251; B82Y 5/00; B82Y 10/00; B82Y 30/00; C01P 2004/00; C01P 2004/04; C01P 2004/64; G01N 33/54346; G01N 33/552; G01N 33/582; Y10T 428/2993
USPC ..... 424/1.11, 1.29, 1.33, 9.1, 9.6, 1.65, 400, 424/489, 490; 428/404; 435/7.1, 7.4, 435/7.92; 506/9; 548/406; 549/214; 977/773, 896, 904
See application file for complete search history.

(56) References Cited

U.S. PATENT DOCUMENTS

| | | |
|---|---|---|
| 2,097,692 A | 11/1937 | Fiegel |
| 2,164,172 A | 6/1939 | Dalton |
| 2,656,508 A | 10/1953 | Coulter |
| 2,692,800 A | 10/1954 | Nichols et al. |
| 2,797,149 A | 6/1957 | Skeggs |
| 2,879,141 A | 3/1959 | Skeggs |
| 2,971,700 A | 2/1961 | Peeps |
| 3,479,141 A | 11/1969 | Smythe et al. |
| 3,608,821 A | 9/1971 | Simm et al. |
| 3,698,635 A | 10/1972 | Sickles |
| 3,816,331 A | 6/1974 | Brown, Jr. et al. |
| 3,930,061 A | 12/1975 | Scharfenberger |
| 3,960,187 A | 6/1976 | Stock et al. |
| 3,980,541 A | 9/1976 | Aine |
| 3,982,541 A | 9/1976 | L'Esperance, Jr. |
| 4,014,469 A | 3/1977 | Sato |
| 4,022,575 A | 5/1977 | Hansen et al. |
| 4,034,966 A | 7/1977 | Suh et al. |
| 4,059,552 A | 11/1977 | Zweigle et al. |
| 4,091,042 A | 5/1978 | Alexanderson et al. |
| 4,117,550 A | 9/1978 | Folland et al. |
| 4,130,394 A | 12/1978 | Negersmith |
| 4,210,809 A | 7/1980 | Pelavin |
| 4,253,846 A | 3/1981 | Smythe et al. |
| 4,266,721 A | 5/1981 | Sickles |
| 4,279,345 A | 7/1981 | Allred |
| 4,297,345 A | 10/1981 | Howarth |
| 4,315,754 A | 2/1982 | Ruzicka et al. |
| 4,378,957 A | 4/1983 | Malkin et al. |
| 4,383,767 A | 5/1983 | Jido |
| 4,439,980 A | 4/1984 | Biblarz et al. |
| 4,508,265 A | 4/1985 | Jido |
| 4,533,634 A | 8/1985 | Maldonado et al. |
| 4,566,908 A * | 1/1986 | Nakatani ............ C09B 67/0033 106/287.11 |
| 4,585,209 A | 4/1986 | Aine et al. |
| 4,618,476 A | 10/1986 | Columbus |

(Continued)

FOREIGN PATENT DOCUMENTS

| | | |
|---|---|---|
| AU | 2004225691 B2 | 6/2010 |
| CA | 2520548 A1 | 10/2004 |

(Continued)

OTHER PUBLICATIONS

Adang, A.E. et al., The contribution of combinatorial chemistry to lead generation: an interim analysis, Curr Med Chem 8: 985-998 (2001).
Advisory Action for U.S. Appl. No. 11/360,845, dated Jun. 14, 2010.
Advisory Action for U.S. Appl. No. 11/698,298 dated May 20, 2011.
Affholter and F. Arnold, Engineering a Revolution, Chemistry in Britain, Apr. 1999, p. 48.
Agrawal and Tang, Site-specific functionalization of oligodeoxynucleotides for non-radioactive labelling, Tetrahedron Letters 31:1543-1546 (1990).
Aharoni et al., High-Throughput screens and selections of enzyme-encoding genes, Curr Opin Chem Biol, 9(2): 210-6 (2005).

(Continued)

*Primary Examiner* — D. L. Jones
(74) *Attorney, Agent, or Firm* — Brown Rudnick LLP; Thomas C. Meyers

(57) ABSTRACT

The present invention relates to labelled silica-based nanoparticles with enhanced properties, to process for preparing them and to uses thereof.

19 Claims, 12 Drawing Sheets

(56) References Cited

U.S. PATENT DOCUMENTS

| | | |
|---|---|---|
| 4,675,285 A | 6/1987 | Clark et al. |
| 4,676,274 A | 6/1987 | Brown |
| 4,683,195 A | 7/1987 | Mullis et al. |
| 4,683,202 A | 7/1987 | Mullis |
| 4,739,044 A | 4/1988 | Stabinsky |
| 4,757,141 A | 7/1988 | Fung et al. |
| 4,767,515 A | 8/1988 | Scott et al. |
| 4,767,929 A | 8/1988 | Valentine |
| 4,779,805 A | 10/1988 | Jackson et al. |
| 4,801,086 A | 1/1989 | Noakes |
| 4,801,529 A | 1/1989 | Perlman |
| 4,829,996 A | 5/1989 | Noakes et al. |
| 4,853,336 A | 8/1989 | Saros et al. |
| 4,865,444 A | 9/1989 | Green et al. |
| 4,883,750 A | 11/1989 | Whiteley et al. |
| 4,908,112 A | 3/1990 | Pace |
| 4,931,225 A | 6/1990 | Cheng |
| 4,941,959 A | 7/1990 | Scott |
| 4,962,885 A | 10/1990 | Coffee |
| 4,963,498 A | 10/1990 | Hillman et al. |
| 4,981,580 A | 1/1991 | Auer |
| 4,996,004 A | 2/1991 | Bucheler et al. |
| 5,091,652 A | 2/1992 | Mathies et al. |
| 5,096,615 A | 3/1992 | Prescott et al. |
| 5,122,360 A | 6/1992 | Harris et al. |
| 5,180,662 A | 1/1993 | Sitkovsky |
| 5,185,099 A | 2/1993 | Delpuech et al. |
| 5,188,290 A | 2/1993 | Gebauer et al. |
| 5,188,291 A | 2/1993 | Cross |
| 5,204,112 A | 4/1993 | Hope et al. |
| 5,207,973 A | 5/1993 | Harris et al. |
| 5,241,159 A | 8/1993 | Chatteriee et al. |
| 5,260,466 A | 11/1993 | McGibbon |
| 5,262,027 A | 11/1993 | Scott |
| 5,270,163 A | 12/1993 | Gold et al. |
| 5,296,375 A | 3/1994 | Kricka et al. |
| 5,304,487 A | 4/1994 | Wilding et al. |
| 5,310,653 A | 5/1994 | Hanausek-Walaszek et al. |
| 5,313,009 A | 5/1994 | Guenkel et al. |
| 5,344,489 A * | 9/1994 | Matijevic ............ C09B 67/0013 106/442 |
| 5,344,594 A | 9/1994 | Sheridon |
| 5,378,957 A | 1/1995 | Kelly |
| 5,397,605 A | 3/1995 | Barbieri et al. |
| 5,399,461 A | 3/1995 | Van et al. |
| 5,399,491 A | 3/1995 | Kacian et al. |
| 5,403,617 A | 4/1995 | Haaland |
| 5,413,924 A | 5/1995 | Kosak et al. |
| 5,417,235 A | 5/1995 | Wise et al. |
| 5,427,946 A | 6/1995 | Kricka et al. |
| 5,445,934 A | 8/1995 | Fodor et al. |
| 5,452,878 A | 9/1995 | Gravesen et al. |
| 5,452,955 A | 9/1995 | Lundstrom |
| 5,454,472 A | 10/1995 | Benecke et al. |
| 5,460,945 A | 10/1995 | Springer et al. |
| 5,475,096 A | 12/1995 | Gold et al. |
| 5,480,614 A | 1/1996 | Kamahori |
| 5,486,335 A | 1/1996 | Wilding et al. |
| 5,498,392 A | 3/1996 | Wilding et al. |
| 5,500,415 A | 3/1996 | Dollat et al. |
| 5,503,851 A | 4/1996 | Mank et al. |
| 5,512,131 A | 4/1996 | Kumar et al. |
| 5,516,635 A | 5/1996 | Ekins et al. |
| 5,518,709 A | 5/1996 | Sutton et al. |
| 5,523,162 A | 6/1996 | Franz et al. |
| 5,587,128 A | 12/1996 | Wilding et al. |
| 5,604,097 A | 2/1997 | Brenner |
| 5,612,188 A | 3/1997 | Shuler et al. |
| 5,616,478 A | 4/1997 | Chetverin et al. |
| 5,617,997 A | 4/1997 | Kobayashi et al. |
| 5,635,358 A | 6/1997 | Wilding et al. |
| 5,636,400 A | 6/1997 | Young |
| 5,641,658 A | 6/1997 | Adams et al. |
| 5,643,729 A | 7/1997 | Taniguchi et al. |
| 5,655,517 A | 8/1997 | Coffee |
| 5,656,155 A | 8/1997 | Norcross et al. |
| 5,661,222 A | 8/1997 | Hare |
| 5,662,874 A | 9/1997 | David |
| 5,670,325 A | 9/1997 | Lapidus et al. |
| 5,681,600 A | 10/1997 | Antinone et al. |
| 5,695,934 A | 12/1997 | Brenner |
| 5,726,026 A | 3/1998 | Wilding et al. |
| 5,726,404 A | 3/1998 | Brody |
| 5,733,526 A | 3/1998 | Trevino et al. |
| 5,739,036 A | 4/1998 | Parris |
| 5,744,366 A | 4/1998 | Kricka et al. |
| 5,750,988 A | 5/1998 | Apffel et al. |
| 5,762,775 A | 6/1998 | DePaoli et al. |
| 5,779,868 A | 7/1998 | Parce et al. |
| 5,783,431 A | 7/1998 | Peterson et al. |
| 5,840,506 A | 11/1998 | Giordano |
| 5,846,719 A | 12/1998 | Brenner et al. |
| 5,849,491 A | 12/1998 | Radomski et al. |
| 5,858,187 A | 1/1999 | Ramsey et al. |
| 5,858,655 A | 1/1999 | Arnold |
| 5,858,670 A | 1/1999 | Lam et al. |
| 5,863,722 A | 1/1999 | Brenner |
| 5,868,322 A | 2/1999 | Loucks, Jr. et al. |
| 5,872,010 A | 2/1999 | Karger et al. |
| 5,876,771 A | 3/1999 | Sizer et al. |
| 5,880,071 A | 3/1999 | Parce et al. |
| 5,882,680 A | 3/1999 | Suzuki et al. |
| 5,884,846 A | 3/1999 | Tan |
| 5,887,755 A | 3/1999 | Hood, III |
| 5,888,746 A | 3/1999 | Tabiti et al. |
| 5,888,778 A | 3/1999 | Shuber |
| 5,904,933 A | 5/1999 | Riess et al. |
| 5,921,678 A | 7/1999 | Desai et al. |
| 5,927,852 A | 7/1999 | Serafin |
| 5,928,870 A | 7/1999 | Lapidus et al. |
| 5,932,100 A | 8/1999 | Yager et al. |
| 5,935,331 A | 8/1999 | Naka et al. |
| 5,942,056 A | 8/1999 | Singh |
| 5,942,443 A | 8/1999 | Parce et al. |
| 5,958,203 A | 9/1999 | Parce et al. |
| 5,972,187 A | 10/1999 | Parce et al. |
| 5,980,936 A | 11/1999 | Krafft et al. |
| 5,989,815 A | 11/1999 | Skolnick et al. |
| 5,989,892 A | 11/1999 | Nishimaki et al. |
| 5,995,341 A | 11/1999 | Tanaka et al. |
| 5,997,636 A | 12/1999 | Gamarnik et al. |
| 6,008,003 A | 12/1999 | Haak-Frendscho et al. |
| 6,023,540 A | 2/2000 | Walt et al. |
| 6,028,066 A | 2/2000 | Unger |
| 6,042,709 A | 3/2000 | Parce et al. |
| 6,045,755 A | 4/2000 | Lebl et al. |
| 6,046,056 A | 4/2000 | Parce et al. |
| 6,048,551 A | 4/2000 | Hilfinger et al. |
| 6,068,199 A | 5/2000 | Coffee |
| 6,080,295 A | 6/2000 | Parce et al. |
| 6,086,740 A | 7/2000 | Kennedy |
| 6,096,495 A | 8/2000 | Kasai et al. |
| 6,103,537 A | 8/2000 | Ullman et al. |
| 6,105,571 A | 8/2000 | Coffee |
| 6,105,877 A | 8/2000 | Coffee |
| 6,116,516 A | 9/2000 | Ganan-Calvo |
| 6,118,849 A | 9/2000 | Tanimori et al. |
| 6,119,953 A | 9/2000 | Ganan-Calvo et al. |
| 6,120,666 A | 9/2000 | Jacobson et al. |
| 6,124,388 A | 9/2000 | Takai et al. |
| 6,124,439 A | 9/2000 | Friedman et al. |
| 6,130,052 A | 10/2000 | Van Baren et al. |
| 6,130,098 A | 10/2000 | Handique et al. |
| 6,137,214 A | 10/2000 | Raina |
| 6,138,077 A | 10/2000 | Brenner |
| 6,139,303 A | 10/2000 | Reed et al. |
| 6,140,053 A | 10/2000 | Koster |
| 6,143,496 A | 11/2000 | Brown et al. |
| 6,149,789 A | 11/2000 | Benecke et al. |
| 6,150,180 A | 11/2000 | Parce et al. |
| 6,150,516 A | 11/2000 | Brenner et al. |
| 6,165,778 A | 12/2000 | Kedar |
| 6,171,796 B1 | 1/2001 | An et al. |
| 6,171,850 B1 | 1/2001 | Nagle et al. |

(56) References Cited

U.S. PATENT DOCUMENTS

| | | |
|---|---|---|
| 6,172,214 B1 | 1/2001 | Brenner |
| 6,172,218 B1 | 1/2001 | Brenner |
| 6,174,160 B1 | 1/2001 | Lee et al. |
| 6,174,469 B1 | 1/2001 | Ganan-Calvo |
| 6,180,372 B1 | 1/2001 | Franzen |
| 6,184,012 B1 | 2/2001 | Neri et al. |
| 6,187,214 B1 | 2/2001 | Ganan-Calvo |
| 6,189,803 B1 | 2/2001 | Ganan-Calvo |
| 6,196,525 B1 | 3/2001 | Ganan-Calvo |
| 6,197,335 B1 | 3/2001 | Sherman |
| 6,197,835 B1 | 3/2001 | Ganan-Calvo |
| 6,203,993 B1 | 3/2001 | Shuber et al. |
| 6,210,396 B1 | 4/2001 | MacDonald et al. |
| 6,210,891 B1 | 4/2001 | Nyren et al. |
| 6,210,896 B1 | 4/2001 | Chan |
| 6,214,558 B1 | 4/2001 | Shuber et al. |
| 6,221,654 B1 | 4/2001 | Quake et al. |
| 6,227,466 B1 | 5/2001 | Hartman et al. |
| 6,234,402 B1 | 5/2001 | Ganan-Calvo |
| 6,235,383 B1 | 5/2001 | Hong et al. |
| 6,235,475 B1 | 5/2001 | Brenner et al. |
| 6,241,159 B1 | 6/2001 | Ganan-Calvo et al. |
| 6,243,373 B1 | 6/2001 | Turock |
| 6,248,378 B1 | 6/2001 | Ganan-Calvo |
| 6,251,661 B1 | 6/2001 | Urabe et al. |
| 6,252,129 B1 | 6/2001 | Coffee |
| 6,258,568 B1 | 7/2001 | Nyren |
| 6,258,858 B1 | 7/2001 | Nakajima et al. |
| 6,263,222 B1 | 7/2001 | Diab et al. |
| 6,266,459 B1 | 7/2001 | Walt et al. |
| 6,267,353 B1 | 7/2001 | Friedline et al. |
| 6,267,858 B1 | 7/2001 | Parce et al. |
| 6,268,165 B1 | 7/2001 | O'Brien |
| 6,268,222 B1 | 7/2001 | Chandler et al. |
| 6,274,320 B1 | 8/2001 | Rothberg et al. |
| 6,274,337 B1 | 8/2001 | Parce et al. |
| 6,294,344 B1 | 9/2001 | O'Brien |
| 6,296,673 B1 | 10/2001 | Santarsiero et al. |
| 6,299,145 B1 | 10/2001 | Ganan-Calvo |
| 6,301,055 B1 | 10/2001 | Legrand et al. |
| 6,306,659 B1 | 10/2001 | Parce et al. |
| 6,310,354 B1 | 10/2001 | Hanninen et al. |
| 6,310,653 B1 | 10/2001 | Malcolm, Jr. et al. |
| 6,316,208 B1 | 11/2001 | Roberts et al. |
| 6,316,213 B1 | 11/2001 | O'Brien |
| 6,318,640 B1 | 11/2001 | Coffee |
| 6,336,463 B1 | 1/2002 | Ohta |
| 6,344,325 B1 | 2/2002 | Quake et al. |
| 6,352,828 B1 | 3/2002 | Brenner |
| 6,355,193 B1 | 3/2002 | Stott |
| 6,355,198 B1 | 3/2002 | Kim et al. |
| 6,357,670 B2 | 3/2002 | Ganan-Calvo |
| 6,386,463 B1 | 5/2002 | Ganan-Calvo |
| 6,391,559 B1 | 5/2002 | Brown et al. |
| 6,394,429 B2 | 5/2002 | Ganan-Calvo |
| 6,399,339 B1 | 6/2002 | Wolberg et al. |
| 6,399,389 B1 | 6/2002 | Parce et al. |
| 6,403,373 B1 | 6/2002 | Scanlan et al. |
| 6,405,936 B1 | 6/2002 | Ganan-Calvo |
| 6,408,878 B2 | 6/2002 | Unger et al. |
| 6,409,832 B2 | 6/2002 | Weigl et al. |
| 6,429,025 B1 | 8/2002 | Parce et al. |
| 6,429,148 B1 | 8/2002 | Chu et al. |
| 6,432,143 B2 | 8/2002 | Kubiak et al. |
| 6,432,148 B1 | 8/2002 | Ganan-Calvo |
| 6,432,630 B1 | 8/2002 | Blankenstein |
| 6,439,103 B1 | 8/2002 | Miller |
| 6,440,706 B1 | 8/2002 | Vogelstein et al. |
| 6,450,139 B1 | 9/2002 | Watanabe |
| 6,450,189 B1 | 9/2002 | Ganan-Calvo |
| 6,454,193 B1 | 9/2002 | Busick et al. |
| 6,464,336 B1 | 10/2002 | Sharma |
| 6,464,886 B2 | 10/2002 | Ganan-Calvo |
| 6,475,441 B1 | 11/2002 | Parce et al. |
| 6,481,648 B1 | 11/2002 | Zimmermann |
| 6,489,103 B1 | 12/2002 | Griffiths et al. |
| 6,503,933 B1 | 1/2003 | Moloney et al. |
| 6,506,609 B1 | 1/2003 | Wada et al. |
| 6,508,988 B1 | 1/2003 | Van Dam et al. |
| 6,520,425 B1 | 2/2003 | Reneker |
| 6,524,456 B1 | 2/2003 | Ramsey et al. |
| 6,530,944 B2 * | 3/2003 | West et al. ............... 607/88 |
| 6,540,395 B2 | 4/2003 | Muhlbauer et al. |
| 6,540,895 B1 | 4/2003 | Spence et al. |
| 6,551,836 B1 | 4/2003 | Chow et al. |
| 6,553,944 B1 | 4/2003 | Allen et al. |
| 6,553,960 B1 | 4/2003 | Yoshikawa et al. |
| 6,554,202 B2 | 4/2003 | Ganan-Calvo |
| 6,557,334 B2 | 5/2003 | Jager |
| 6,557,834 B2 | 5/2003 | Ganan-Calvo |
| 6,558,944 B1 | 5/2003 | Parce et al. |
| 6,558,960 B1 | 5/2003 | Parce et al. |
| 6,560,030 B2 | 5/2003 | Legrand et al. |
| 6,565,010 B2 | 5/2003 | Anderson et al. |
| 6,569,631 B1 | 5/2003 | Pantoliano et al. |
| 6,576,420 B1 | 6/2003 | Carson et al. |
| 6,591,852 B1 | 7/2003 | McNeely et al. |
| 6,592,321 B2 | 7/2003 | Bonker et al. |
| 6,592,821 B1 | 7/2003 | Wada et al. |
| 6,608,726 B2 | 8/2003 | Legrand et al. |
| 6,610,499 B1 | 8/2003 | Fulwyler et al. |
| 6,614,598 B1 | 9/2003 | Quake et al. |
| 6,627,603 B1 | 9/2003 | Bibette et al. |
| 6,630,006 B2 | 10/2003 | Santarsiero et al. |
| 6,630,353 B1 | 10/2003 | Parce et al. |
| 6,632,619 B1 | 10/2003 | Harrison et al. |
| 6,638,749 B1 | 10/2003 | Beckman et al. |
| 6,645,432 B1 | 11/2003 | Anderson et al. |
| 6,646,253 B1 | 11/2003 | Rohwer et al. |
| 6,653,626 B2 | 11/2003 | Fischer et al. |
| 6,656,267 B2 | 12/2003 | Newman |
| 6,659,370 B1 | 12/2003 | Inoue |
| 6,660,252 B2 | 12/2003 | Matathia et al. |
| 6,670,142 B2 | 12/2003 | Lau et al. |
| 6,679,441 B1 | 1/2004 | Borra et al. |
| 6,680,178 B2 | 1/2004 | Harris et al. |
| 6,682,890 B2 | 1/2004 | Mack et al. |
| 6,717,136 B2 | 4/2004 | Andersson et al. |
| 6,729,561 B2 | 5/2004 | Hirae et al. |
| 6,739,036 B2 | 5/2004 | Koike et al. |
| 6,744,046 B2 | 6/2004 | Valaskovic et al. |
| 6,752,922 B2 | 6/2004 | Huang et al. |
| 6,753,147 B2 | 6/2004 | Vogelstein et al. |
| 6,766,817 B2 | 7/2004 | da Silva |
| 6,767,194 B2 | 7/2004 | Jeon et al. |
| 6,767,704 B2 | 7/2004 | Waldman et al. |
| 6,790,328 B2 | 9/2004 | Jacobson et al. |
| 6,793,753 B2 | 9/2004 | Unger et al. |
| 6,797,056 B2 | 9/2004 | David |
| 6,800,849 B2 | 10/2004 | Staats |
| 6,806,058 B2 | 10/2004 | Jesperson et al. |
| 6,808,382 B2 | 10/2004 | Lanfranchi |
| 6,808,882 B2 | 10/2004 | Griffiths et al. |
| 6,814,980 B2 | 11/2004 | Levy et al. |
| 6,818,395 B1 | 11/2004 | Quake et al. |
| 6,832,787 B1 | 12/2004 | Renzi |
| 6,833,242 B2 | 12/2004 | Quake et al. |
| 6,841,350 B2 | 1/2005 | Ogden et al. |
| 6,844,377 B1 * | 1/2005 | Auweter ............. C08K 5/0041 523/223 |
| 6,872,250 B2 | 3/2005 | David et al. |
| 6,890,487 B1 | 5/2005 | Sklar et al. |
| 6,897,018 B1 | 5/2005 | Yuan et al. |
| 6,905,844 B2 | 6/2005 | Kim |
| 6,918,404 B2 | 7/2005 | Dias da Silva |
| 6,926,313 B1 | 8/2005 | Renzi |
| 6,935,768 B2 | 8/2005 | Lowe et al. |
| 6,936,417 B2 | 8/2005 | Orntoft |
| 6,942,978 B1 | 9/2005 | O'Brien |
| 6,949,342 B2 | 9/2005 | Golub et al. |
| 6,960,437 B2 | 11/2005 | Enzelberger et al. |
| 6,974,667 B2 | 12/2005 | Horne et al. |
| 6,998,232 B1 | 2/2006 | Feinstein et al. |
| 7,022,472 B2 | 4/2006 | Robbins et al. |

(56) References Cited

U.S. PATENT DOCUMENTS

| | | |
|---|---|---|
| 7,041,481 B2 | 5/2006 | Anderson et al. |
| 7,049,072 B2 | 5/2006 | Seshi |
| 7,056,674 B2 | 6/2006 | Baker et al. |
| 7,057,026 B2 | 6/2006 | Barnes et al. |
| 7,066,586 B2 | 6/2006 | da Silva |
| 7,068,874 B2 | 6/2006 | Wang et al. |
| 7,078,180 B2 | 7/2006 | Genetta |
| 7,081,192 B1 | 7/2006 | Wang et al. |
| 7,081,340 B2 | 7/2006 | Baker et al. |
| 7,090,983 B1 | 8/2006 | Muramatsu et al. |
| 7,115,230 B2 | 10/2006 | Sundararajan et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,153,700 B1 | 12/2006 | Pardee et al. |
| 7,156,917 B2 | 1/2007 | Moriyama et al. |
| 7,163,801 B2 | 1/2007 | Reed |
| 7,169,560 B2 | 1/2007 | Lapidus et al. |
| 7,171,311 B2 | 1/2007 | Dai et al. |
| 7,198,899 B2 | 4/2007 | Schleyer et al. |
| 7,204,431 B2 | 4/2007 | Li et al. |
| 7,229,770 B1 | 6/2007 | Price et al. |
| 7,252,943 B2 | 8/2007 | Griffiths et al. |
| 7,267,938 B2 | 9/2007 | Anderson et al. |
| 7,268,167 B2 | 9/2007 | Higuchi et al. |
| 7,282,337 B1 | 10/2007 | Harris |
| 7,291,462 B2 | 11/2007 | O'Brien et al. |
| 7,294,503 B2 | 11/2007 | Quake et al. |
| 7,300,765 B2 | 11/2007 | Patel |
| 7,308,364 B2 | 12/2007 | Shaughnessy et al. |
| 7,314,721 B2 | 1/2008 | Gure et al. |
| 7,316,906 B2 | 1/2008 | Chiorazzi et al. |
| 7,326,529 B2 | 2/2008 | Ali et al. |
| 7,332,280 B2 | 2/2008 | Levy et al. |
| 7,332,590 B2 | 2/2008 | Nacht et al. |
| 7,341,211 B2 | 3/2008 | Ganan Calvo et al. |
| 7,348,142 B2 | 3/2008 | Wang |
| 7,358,231 B1 | 4/2008 | McCaffey et al. |
| 7,361,474 B2 | 4/2008 | Siegler |
| 7,364,862 B2 | 4/2008 | Ali et al. |
| 7,368,255 B2 | 5/2008 | Bae et al. |
| 7,378,233 B2 | 5/2008 | Sidransky et al. |
| 7,378,280 B2 | 5/2008 | Quake et al. |
| 7,390,463 B2 | 6/2008 | He et al. |
| 7,393,665 B2 | 7/2008 | Brenner |
| 7,405,002 B2 * | 7/2008 | Ying ............... C30B 29/60 428/404 |
| 7,416,851 B2 | 8/2008 | Davi et al. |
| 7,429,467 B2 | 9/2008 | Holliger et al. |
| 7,432,064 B2 | 10/2008 | Salceda et al. |
| 7,442,507 B2 | 10/2008 | Polsky et al. |
| 7,449,303 B2 | 11/2008 | Coignet |
| 7,468,271 B2 | 12/2008 | Golovchenko et al. |
| 7,473,530 B2 | 1/2009 | Huttemann |
| 7,473,531 B1 | 1/2009 | Domon et al. |
| 7,476,506 B2 | 1/2009 | Schleyer et al. |
| 7,479,370 B2 | 1/2009 | Coignet |
| 7,479,371 B2 | 1/2009 | Ando et al. |
| 7,479,376 B2 | 1/2009 | Waldman et al. |
| 7,482,129 B2 | 1/2009 | Soyupak et al. |
| 7,501,244 B2 | 3/2009 | Reinhard et al. |
| 7,504,214 B2 | 3/2009 | Erlander et al. |
| 7,507,532 B2 | 3/2009 | Chang et al. |
| 7,507,541 B2 | 3/2009 | Raitano et al. |
| 7,510,707 B2 | 3/2009 | Platica et al. |
| 7,510,842 B2 | 3/2009 | Podust et al. |
| 7,514,209 B2 | 4/2009 | Dai et al. |
| 7,514,210 B2 | 4/2009 | Holliger et al. |
| 7,524,633 B2 | 4/2009 | Sidransky |
| 7,527,933 B2 | 5/2009 | Sahin et al. |
| 7,537,897 B2 | 5/2009 | Brenner et al. |
| 7,541,383 B2 | 6/2009 | Fu et al. |
| 7,544,473 B2 | 6/2009 | Brenner |
| 7,556,776 B2 | 7/2009 | Fraden et al. |
| 7,582,446 B2 | 9/2009 | Griffiths et al. |
| 7,622,081 B2 | 11/2009 | Chou et al. |
| 7,632,562 B2 | 12/2009 | Nair et al. |
| 7,635,562 B2 | 12/2009 | Harris et al. |
| 7,638,276 B2 | 12/2009 | Griffiths et al. |
| 7,655,435 B2 | 2/2010 | Holliger et al. |
| 7,655,470 B2 | 2/2010 | Ismagilov et al. |
| 7,666,593 B2 | 2/2010 | Lapidus |
| 7,691,576 B2 | 4/2010 | Holliger et al. |
| 7,698,287 B2 | 4/2010 | Becker et al. |
| 7,708,949 B2 | 5/2010 | Stone et al. |
| 7,718,578 B2 | 5/2010 | Griffiths et al. |
| 7,736,890 B2 | 6/2010 | Sia et al. |
| 7,741,130 B2 | 6/2010 | Lee, Jr. et al. |
| 7,814,175 B1 | 10/2010 | Chang et al. |
| 7,824,889 B2 | 11/2010 | Vogelstein et al. |
| 7,897,044 B2 | 3/2011 | Hoyos et al. |
| 7,897,341 B2 | 3/2011 | Griffiths et al. |
| 7,901,939 B2 | 3/2011 | Ismagilov et al. |
| 7,968,287 B2 | 6/2011 | Griffiths et al. |
| 8,012,382 B2 | 9/2011 | Kim et al. |
| 8,153,402 B2 | 4/2012 | Holliger et al. |
| 9,080,056 B2 * | 7/2015 | Glennon ............... B01J 20/283 |
| 2001/0010338 A1 | 8/2001 | Ganan-Calvo |
| 2001/0020011 A1 | 9/2001 | Mathiowitz et al. |
| 2001/0023078 A1 | 9/2001 | Bawendi et al. |
| 2001/0029983 A1 | 10/2001 | Unger et al. |
| 2001/0034031 A1 | 10/2001 | Short et al. |
| 2001/0041343 A1 | 11/2001 | Pankowsky |
| 2001/0041344 A1 | 11/2001 | Sepetov et al. |
| 2001/0042793 A1 | 11/2001 | Ganan-Calvo |
| 2001/0048900 A1 | 12/2001 | Bardell et al. |
| 2001/0050881 A1 | 12/2001 | Depaoli et al. |
| 2002/0004532 A1 | 1/2002 | Matathia et al. |
| 2002/0005354 A1 | 1/2002 | Spence et al. |
| 2002/0008028 A1 | 1/2002 | Jacobson et al. |
| 2002/0012971 A1 | 1/2002 | Mehta |
| 2002/0022038 A1 | 2/2002 | Biatry et al. |
| 2002/0022261 A1 | 2/2002 | Anderson et al. |
| 2002/0033422 A1 | 3/2002 | Ganan-Calvo |
| 2002/0036139 A1 | 3/2002 | Becker et al. |
| 2002/0058332 A1 | 5/2002 | Quake et al. |
| 2002/0067800 A1 | 6/2002 | Newman et al. |
| 2002/0119459 A1 | 8/2002 | Griffiths |
| 2002/0143437 A1 | 10/2002 | Handique et al. |
| 2002/0155080 A1 | 10/2002 | Glenn et al. |
| 2002/0158027 A1 | 10/2002 | Moon et al. |
| 2002/0164271 A1 | 11/2002 | Ho |
| 2002/0164629 A1 | 11/2002 | Quake et al. |
| 2003/0012586 A1 | 1/2003 | Iwata et al. |
| 2003/0015425 A1 | 1/2003 | Bohm et al. |
| 2003/0017579 A1 | 1/2003 | Corn et al. |
| 2003/0039169 A1 | 2/2003 | Ehrfeld et al. |
| 2003/0059764 A1 | 3/2003 | Ravkin et al. |
| 2003/0061687 A1 | 4/2003 | Hansen et al. |
| 2003/0064414 A1 | 4/2003 | Benecky et al. |
| 2003/0082795 A1 | 5/2003 | Shuler et al. |
| 2003/0124586 A1 | 7/2003 | Griffiths et al. |
| 2003/0144260 A1 | 7/2003 | Gilon |
| 2003/0148544 A1 | 8/2003 | Nie et al. |
| 2003/0183525 A1 | 10/2003 | Elrod et al. |
| 2003/0224509 A1 | 12/2003 | Moon et al. |
| 2003/0229376 A1 | 12/2003 | Sandhu |
| 2003/0230486 A1 | 12/2003 | Chien et al. |
| 2003/0232356 A1 | 12/2003 | Dooley et al. |
| 2004/0005582 A1 | 1/2004 | Shipwash |
| 2004/0005594 A1 | 1/2004 | Holliger et al. |
| 2004/0018525 A1 | 1/2004 | Wirtz et al. |
| 2004/0027915 A1 | 2/2004 | Lowe et al. |
| 2004/0037813 A1 | 2/2004 | Simpson et al. |
| 2004/0041093 A1 | 3/2004 | Schultz et al. |
| 2004/0050946 A1 | 3/2004 | Wang et al. |
| 2004/0053247 A1 | 3/2004 | Cordon-Cardo et al. |
| 2004/0068019 A1 | 4/2004 | Higuchi et al. |
| 2004/0071781 A1 | 4/2004 | Chattopadhyay et al. |
| 2004/0079881 A1 | 4/2004 | Fischer et al. |
| 2004/0096515 A1 | 5/2004 | Bausch et al. |
| 2004/0101822 A1 * | 5/2004 | Wiesner ............... B82Y 30/00 435/5 |
| 2004/0136497 A1 | 7/2004 | Meldrum et al. |

(56) References Cited

U.S. PATENT DOCUMENTS

| | | |
|---|---|---|
| 2004/0146921 A1 | 7/2004 | Eveleigh et al. |
| 2004/0159633 A1 | 8/2004 | Whitesides et al. |
| 2004/0181131 A1 | 9/2004 | Maynard et al. |
| 2004/0181343 A1 | 9/2004 | Wigstrom et al. |
| 2004/0182712 A1 | 9/2004 | Basol |
| 2004/0188254 A1 | 9/2004 | Spaid |
| 2004/0224419 A1 | 11/2004 | Zheng et al. |
| 2004/0253731 A1 | 12/2004 | Holliger et al. |
| 2004/0258203 A1 | 12/2004 | Yamano et al. |
| 2005/0032238 A1 | 2/2005 | Karp et al. |
| 2005/0032240 A1 | 2/2005 | Lee et al. |
| 2005/0037392 A1 | 2/2005 | Griffiths et al. |
| 2005/0042648 A1 | 2/2005 | Griffiths et al. |
| 2005/0048467 A1 | 3/2005 | Sastry et al. |
| 2005/0064460 A1 | 3/2005 | Holliger et al. |
| 2005/0069920 A1 | 3/2005 | Griffiths et al. |
| 2005/0079510 A1 | 4/2005 | Berka et al. |
| 2005/0084923 A1 | 4/2005 | Mueller et al. |
| 2005/0087122 A1 | 4/2005 | Ismagliov et al. |
| 2005/0095611 A1 | 5/2005 | Chan et al. |
| 2005/0100895 A1 | 5/2005 | Waldman et al. |
| 2005/0129582 A1 | 6/2005 | Breidford et al. |
| 2005/0152908 A1 | 7/2005 | Liew et al. |
| 2005/0164239 A1 | 7/2005 | Griffiths et al. |
| 2005/0170431 A1 | 8/2005 | Ibrahim et al. |
| 2005/0172476 A1 | 8/2005 | Stone et al. |
| 2005/0183995 A1 | 8/2005 | Deshpande et al. |
| 2005/0207940 A1 | 9/2005 | Butler et al. |
| 2005/0221339 A1 | 10/2005 | Griffiths et al. |
| 2005/0226742 A1 | 10/2005 | Unger et al. |
| 2005/0227264 A1 | 10/2005 | Nobile et al. |
| 2005/0260566 A1 | 11/2005 | Fischer et al. |
| 2005/0272159 A1 | 12/2005 | Ismagilov et al. |
| 2006/0003347 A1 | 1/2006 | Griffiths et al. |
| 2006/0003429 A1 | 1/2006 | Frost et al. |
| 2006/0003439 A1 | 1/2006 | Ismagilov et al. |
| 2006/0036348 A1 | 2/2006 | Handique et al. |
| 2006/0046257 A1 | 3/2006 | Pollock et al. |
| 2006/0051329 A1 | 3/2006 | Lee et al. |
| 2006/0078888 A1 | 4/2006 | Griffiths et al. |
| 2006/0078893 A1 | 4/2006 | Griffiths et al. |
| 2006/0094119 A1 | 5/2006 | Ismagilov et al. |
| 2006/0105170 A1* | 5/2006 | Dobson et al. ............... 428/403 |
| 2006/0108012 A1 | 5/2006 | Barrow et al. |
| 2006/0110759 A1 | 5/2006 | Paris et al. |
| 2006/0115821 A1 | 6/2006 | Einstein et al. |
| 2006/0147909 A1 | 7/2006 | Rarbach et al. |
| 2006/0153924 A1 | 7/2006 | Griffiths et al. |
| 2006/0154298 A1 | 7/2006 | Griffiths et al. |
| 2006/0160762 A1 | 7/2006 | Zetter et al. |
| 2006/0163385 A1 | 7/2006 | Link et al. |
| 2006/0169800 A1 | 8/2006 | Rosell et al. |
| 2006/0195269 A1 | 8/2006 | Yeatman et al. |
| 2006/0223127 A1 | 10/2006 | Yip et al. |
| 2006/0234254 A1 | 10/2006 | An et al. |
| 2006/0234259 A1 | 10/2006 | Rubin et al. |
| 2006/0245971 A1* | 11/2006 | Burns ............... G01N 21/6428 422/400 |
| 2006/0252057 A1 | 11/2006 | Raponi et al. |
| 2006/0258841 A1 | 11/2006 | Michl et al. |
| 2006/0263888 A1 | 11/2006 | Fritz et al. |
| 2006/0269558 A1 | 11/2006 | Murphy et al. |
| 2006/0269971 A1 | 11/2006 | Diamandis |
| 2006/0281089 A1 | 12/2006 | Gibson et al. |
| 2007/0003442 A1 | 1/2007 | Link et al. |
| 2007/0026439 A1 | 2/2007 | Faulstich et al. |
| 2007/0053896 A1 | 3/2007 | Ahmed et al. |
| 2007/0054119 A1 | 3/2007 | Garstecki et al. |
| 2007/0056853 A1 | 3/2007 | Aizenberg et al. |
| 2007/0077572 A1 | 4/2007 | Tawfik et al. |
| 2007/0077579 A1 | 4/2007 | Griffiths et al. |
| 2007/0092914 A1 | 4/2007 | Griffiths et al. |
| 2007/0120899 A1 | 5/2007 | Ohnishi et al. |
| 2007/0154889 A1 | 7/2007 | Wang |
| 2007/0166705 A1 | 7/2007 | Milton et al. |
| 2007/0184439 A1 | 8/2007 | Guilford et al. |
| 2007/0184489 A1 | 8/2007 | Griffiths et al. |
| 2007/0195127 A1 | 8/2007 | Ahn et al. |
| 2007/0259351 A1 | 11/2007 | Chinitz et al. |
| 2007/0259368 A1 | 11/2007 | An et al. |
| 2007/0259374 A1 | 11/2007 | Griffiths et al. |
| 2007/0292869 A1 | 12/2007 | Becker et al. |
| 2008/0003142 A1 | 1/2008 | Link et al. |
| 2008/0009005 A1 | 1/2008 | Kruk |
| 2008/0014589 A1 | 1/2008 | Link et al. |
| 2008/0014590 A1 | 1/2008 | Dahary et al. |
| 2008/0020940 A1 | 1/2008 | Stedronsky et al. |
| 2008/0021330 A1 | 1/2008 | Hwang et al. |
| 2008/0023330 A1 | 1/2008 | Viovy et al. |
| 2008/0038754 A1 | 2/2008 | Farias-Eisner et al. |
| 2008/0044828 A1 | 2/2008 | Kwok |
| 2008/0050378 A1 | 2/2008 | Nakamura et al. |
| 2008/0050723 A1 | 2/2008 | Belacel et al. |
| 2008/0053205 A1 | 3/2008 | Pollack et al. |
| 2008/0057514 A1 | 3/2008 | Goldenring |
| 2008/0058432 A1 | 3/2008 | Wang et al. |
| 2008/0063227 A1 | 3/2008 | Rohrseitz |
| 2008/0064047 A1 | 3/2008 | Zetter et al. |
| 2008/0081330 A1 | 4/2008 | Kahvejian |
| 2008/0081333 A1 | 4/2008 | Mori et al. |
| 2008/0092973 A1 | 4/2008 | Lai |
| 2008/0113340 A1 | 5/2008 | Schlegel |
| 2008/0118462 A1 | 5/2008 | Alani et al. |
| 2008/0138806 A1 | 6/2008 | Chow et al. |
| 2008/0166772 A1 | 7/2008 | Hollinger et al. |
| 2008/0171078 A1 | 7/2008 | Gray |
| 2008/0176211 A1 | 7/2008 | Spence et al. |
| 2008/0176236 A1 | 7/2008 | Tsao et al. |
| 2008/0181850 A1 | 7/2008 | Thaxton et al. |
| 2008/0206756 A1 | 8/2008 | Lee et al. |
| 2008/0213377 A1* | 9/2008 | Bhatia et al. ............... 424/489 |
| 2008/0222741 A1 | 9/2008 | Chinnaiyan |
| 2008/0234138 A1 | 9/2008 | Shaughnessy et al. |
| 2008/0234139 A1 | 9/2008 | Shaughnessy et al. |
| 2008/0268473 A1 | 10/2008 | Moses et al. |
| 2008/0269157 A1 | 10/2008 | Srivastava et al. |
| 2008/0274908 A1 | 11/2008 | Chang |
| 2008/0280302 A1 | 11/2008 | Kebebew |
| 2008/0286199 A1 | 11/2008 | Livingston et al. |
| 2008/0286801 A1 | 11/2008 | Arjol et al. |
| 2008/0286811 A1 | 11/2008 | Moses et al. |
| 2008/0293578 A1 | 11/2008 | Shaugnessy et al. |
| 2008/0311570 A1 | 12/2008 | Lai |
| 2008/0311604 A1 | 12/2008 | Elting et al. |
| 2009/0004687 A1 | 1/2009 | Mansfield et al. |
| 2009/0005254 A1 | 1/2009 | Griffiths et al. |
| 2009/0012187 A1 | 1/2009 | Chu et al. |
| 2009/0017463 A1 | 1/2009 | Bhowmick |
| 2009/0021728 A1 | 1/2009 | Heinz et al. |
| 2009/0023137 A1 | 1/2009 | Van Der Zee et al. |
| 2009/0026082 A1 | 1/2009 | Rothberg et al. |
| 2009/0029372 A1 | 1/2009 | Wewer |
| 2009/0042737 A1 | 2/2009 | Katz et al. |
| 2009/0053700 A1 | 2/2009 | Griffiths et al. |
| 2009/0053732 A1 | 2/2009 | Vermesh et al. |
| 2009/0060797 A1 | 3/2009 | Mathies et al. |
| 2009/0062144 A1 | 3/2009 | Guo |
| 2009/0068170 A1 | 3/2009 | Weitz et al. |
| 2009/0075265 A1 | 3/2009 | Budiman et al. |
| 2009/0075307 A1 | 3/2009 | Fischer et al. |
| 2009/0075311 A1 | 3/2009 | Karl |
| 2009/0081237 A1 | 3/2009 | D'Andrea et al. |
| 2009/0081685 A1 | 3/2009 | Beyer et al. |
| 2009/0087849 A1 | 4/2009 | Malinowski et al. |
| 2009/0092973 A1 | 4/2009 | Erlander et al. |
| 2009/0098542 A1 | 4/2009 | Budiman et al. |
| 2009/0098543 A1 | 4/2009 | Budiman et al. |
| 2009/0118128 A1 | 5/2009 | Liu et al. |
| 2009/0124569 A1 | 5/2009 | Bergan et al. |
| 2009/0127454 A1 | 5/2009 | Ritchie et al. |
| 2009/0127589 A1 | 5/2009 | Rothberg et al. |
| 2009/0131353 A1 | 5/2009 | Insel et al. |
| 2009/0131543 A1 | 5/2009 | Weitz et al. |

(56) References Cited

U.S. PATENT DOCUMENTS

| | | | |
|---|---|---|---|
| 2009/0169482 A1* | 7/2009 | Zheng | A61K 49/0032 424/9.6 |
| 2009/0191565 A1 | 7/2009 | Lapidus et al. | |
| 2009/0197248 A1 | 8/2009 | Griffiths et al. | |
| 2009/0197772 A1 | 8/2009 | Griffiths et al. | |
| 2009/0246788 A1 | 10/2009 | Albert et al. | |
| 2009/0325236 A1 | 12/2009 | Griffiths et al. | |
| 2010/0003687 A1 | 1/2010 | Simen et al. | |
| 2010/0009353 A1 | 1/2010 | Barnes et al. | |
| 2010/0022414 A1 | 1/2010 | Link et al. | |
| 2010/0035252 A1 | 2/2010 | Rothberg et al. | |
| 2010/0075436 A1 | 3/2010 | Urdea et al. | |
| 2010/0105112 A1 | 4/2010 | Holtze et al. | |
| 2010/0111768 A1 | 5/2010 | Banerjee et al. | |
| 2010/0124759 A1 | 5/2010 | Wang et al. | |
| 2010/0136544 A1 | 6/2010 | Agresti et al. | |
| 2010/0137143 A1 | 6/2010 | Rothberg et al. | |
| 2010/0137163 A1 | 6/2010 | Link et al. | |
| 2010/0159592 A1 | 6/2010 | Holliger et al. | |
| 2010/0172803 A1 | 7/2010 | Stone et al. | |
| 2010/0183504 A1* | 7/2010 | Chen | A61K 47/48861 424/1.29 |
| 2010/0188073 A1 | 7/2010 | Rothberg et al. | |
| 2010/0197507 A1 | 8/2010 | Rothberg et al. | |
| 2010/0210479 A1 | 8/2010 | Griffiths et al. | |
| 2010/0213628 A1 | 8/2010 | Bausch et al. | |
| 2010/0233026 A1 | 9/2010 | Ismagliov et al. | |
| 2010/0282617 A1 | 11/2010 | Rothberg et al. | |
| 2010/0300559 A1 | 12/2010 | Schultz et al. | |
| 2010/0300895 A1 | 12/2010 | Nobile et al. | |
| 2010/0301398 A1 | 12/2010 | Rothberg et al. | |
| 2010/0304982 A1 | 12/2010 | Hinz et al. | |
| 2011/0000560 A1 | 1/2011 | Miller et al. | |
| 2011/0142734 A1 | 6/2011 | Ismagliov et al. | |
| 2011/0174622 A1 | 7/2011 | Ismagilov et al. | |
| 2011/0176966 A1 | 7/2011 | Ismagilov et al. | |
| 2011/0177494 A1 | 7/2011 | Ismagilov et al. | |
| 2011/0177586 A1 | 7/2011 | Ismagilov et al. | |
| 2011/0177609 A1 | 7/2011 | Ismagilov et al. | |
| 2011/0188717 A1 | 8/2011 | Baudry et al. | |
| 2011/0190146 A1 | 8/2011 | Boehm et al. | |
| 2011/0244455 A1 | 10/2011 | Larson et al. | |
| 2011/0250597 A1 | 10/2011 | Larson et al. | |
| 2011/0275063 A1 | 11/2011 | Weitz et al. | |
| 2012/0010098 A1 | 1/2012 | Griffiths et al. | |
| 2012/0015382 A1 | 1/2012 | Weitz et al. | |
| 2012/0015822 A1 | 1/2012 | Weitz et al. | |

FOREIGN PATENT DOCUMENTS

| | | |
|---|---|---|
| CH | 563807 A5 | 7/1975 |
| DE | 4308839 C2 | 4/1997 |
| EP | 0047130 B1 | 2/1985 |
| EP | 0249007 A3 | 3/1991 |
| EP | 0476178 A1 | 3/1992 |
| EP | 0540281 B1 | 7/1996 |
| EP | 0528580 B1 | 12/1996 |
| EP | 0895120 | 2/1999 |
| EP | 1741482 | 1/2007 |
| EP | 2127736 | 12/2009 |
| GB | 0114854.3 | 4/1969 |
| GB | 1446998 | 8/1976 |
| GB | 2005224 | 4/1979 |
| GB | 2047880 | 12/1980 |
| GB | 2062225 | 5/1981 |
| GB | 2064114 | 6/1981 |
| GB | 2097692 A | 11/1982 |
| GB | 0221053.2 | 6/1989 |
| JP | 3-232525 | 10/1998 |
| JP | 2000271475 | 10/2000 |
| WO | WO-84/02000 | 5/1984 |
| WO | WO-91/05058 A1 | 4/1991 |
| WO | WO-91/07772 | 5/1991 |
| WO | WO-92/03734 | 3/1992 |
| WO | WO-92/21746 | 12/1992 |
| WO | WO-93/03151 | 2/1993 |
| WO | WO-93/08278 | 4/1993 |
| WO | WO-93/22053 | 11/1993 |
| WO | WO-93/22054 | 11/1993 |
| WO | WO-93/22055 | 11/1993 |
| WO | WO-93/22058 | 11/1993 |
| WO | WO-93/22421 | 11/1993 |
| WO | WO-94/16332 | 7/1994 |
| WO | WO-94/23738 | 10/1994 |
| WO | WO-94/24314 | 10/1994 |
| WO | WO-94/26766 | 11/1994 |
| WO | WO-98/00705 | 1/1995 |
| WO | WO-95/11922 | 5/1995 |
| WO | WO-95/19922 | 7/1995 |
| WO | WO-95/24929 | 9/1995 |
| WO | WO-95/33447 | 12/1995 |
| WO | WO-96/34112 | 10/1996 |
| WO | WO-96/38730 | 12/1996 |
| WO | WO-96/40062 | 12/1996 |
| WO | WO-96/40723 | 12/1996 |
| WO | WO-97/00125 | 1/1997 |
| WO | WO-97/00442 | 1/1997 |
| WO | WO-97/04297 | 2/1997 |
| WO | WO-97/04748 | 2/1997 |
| WO | WO-97/23140 | 7/1997 |
| WO | WO-97/28556 | 8/1997 |
| WO | WO-97/39814 | 10/1997 |
| WO | WO-97/40141 | 10/1997 |
| WO | WO-97/45644 | 12/1997 |
| WO | WO-97/47763 | 12/1997 |
| WO | WO-98/00231 | 1/1998 |
| WO | WO-98/02237 | 1/1998 |
| WO | WO-98/10267 | 3/1998 |
| WO | WO-98/13502 | 4/1998 |
| WO | WO-98/23733 | 6/1998 |
| WO | WO-98/31700 | 7/1998 |
| WO | WO-98/33001 | 7/1998 |
| WO | WO-98/34120 | 8/1998 |
| WO | WO-98/37186 | 8/1998 |
| WO | WO-98/41869 | 9/1998 |
| WO | WO-98/52691 | 11/1998 |
| WO | WO-98/58085 | 12/1998 |
| WO | WO-99/02671 | 1/1999 |
| WO | WO-99/22858 | 5/1999 |
| WO | WO-99/28020 | 6/1999 |
| WO | WO-99/31019 | 6/1999 |
| WO | WO-00/04139 | 7/1999 |
| WO | WO-99/54730 | 10/1999 |
| WO | WO-99/61888 | 12/1999 |
| WO | WO-00/47322 | 2/2000 |
| WO | WO-00/52455 | 2/2000 |
| WO | WO-00/40712 | 6/2000 |
| WO | WO-00/61275 | 10/2000 |
| WO | WO-00/70080 | 11/2000 |
| WO | WO-00/76673 | 12/2000 |
| WO | WO-01/12327 | 2/2001 |
| WO | WO-01/14589 | 3/2001 |
| WO | WO-01/18244 | 3/2001 |
| WO | WO-01/64332 | 9/2001 |
| WO | WO-01/68257 | 9/2001 |
| WO | WO-01/69289 | 9/2001 |
| WO | WO-01/72431 | 10/2001 |
| WO | WO-01/80283 | 10/2001 |
| WO | WO-02/18949 | 3/2002 |
| WO | WO-02/22869 | 3/2002 |
| WO | WO-02/022869 | 3/2002 |
| WO | WO-02/23163 | 3/2002 |
| WO | WO-02/31203 | 4/2002 |
| WO | WO-02/031203 | 4/2002 |
| WO | WO-02/047665 | 6/2002 |
| WO | WO-02/47665 | 8/2002 |
| WO | WO-02/060275 | 8/2002 |
| WO | WO-02/078845 | 10/2002 |
| WO | WO-02/103011 | 12/2002 |
| WO | WO-02/103363 | 12/2002 |
| WO | WO-03/011443 | 2/2003 |
| WO | WO-03/037302 | 5/2003 |
| WO | WO-03/044187 | 5/2003 |

(56) References Cited

FOREIGN PATENT DOCUMENTS

| WO | WO-03/078659 | 9/2003 |
|---|---|---|
| WO | WO-03/099843 | 12/2003 |
| WO | WO-2004/002627 | 1/2004 |
| WO | WO-2004/018497 | 3/2004 |
| WO | WO-2004/024917 | 3/2004 |
| WO | WO-2004/038363 | 5/2004 |
| WO | WO-2004/069849 | 8/2004 |
| WO | WO-2004/074504 | 9/2004 |
| WO | WO-2004/083443 | 9/2004 |
| WO | WO-2004/087308 | 10/2004 |
| WO | WO-2004/088314 | 10/2004 |
| WO | WO-2004/091763 | 10/2004 |
| WO | WO-2004/102204 | 11/2004 |
| WO | WO-2004/103565 | 12/2004 |
| WO | WO-2005/000970 | 1/2005 |
| WO | WO-2005/002730 | 1/2005 |
| WO | WO-2005/021151 | 3/2005 |
| WO | WO-2005/103106 | 11/2005 |
| WO | WO-2005/118138 | 12/2005 |
| WO | WO-2006/002641 | 1/2006 |
| WO | WO-2006/009657 | 1/2006 |
| WO | WO-2006/027757 | 3/2006 |
| WO | WO-2006/038035 | 4/2006 |
| WO | WO-2006/040551 | 4/2006 |
| WO | WO-2006/040554 | 4/2006 |
| WO | WO-2006/078841 | 7/2006 |
| WO | WO-2006/096571 | 9/2006 |
| WO | WO-2006/101851 | 9/2006 |
| WO | WO-2007/021343 | 2/2007 |
| WO | WO-2007/030501 | 3/2007 |
| WO | WO-2007/081385 | 7/2007 |
| WO | WO-2007/081387 | 7/2007 |
| WO | WO-2007/089541 | 8/2007 |
| WO | WO-2007/114794 | 10/2007 |
| WO | WO-2007/123744 | 11/2007 |
| WO | WO-2007/133710 | 11/2007 |
| WO | WO-2007/138178 | 12/2007 |
| WO | WO-2008/021123 | 2/2008 |
| WO | WO-2008/063227 | 5/2008 |
| WO | WO-2008/097559 | 8/2008 |
| WO | WO-2008/121342 | 10/2008 |
| WO | WO-2008/130623 | 10/2008 |
| WO | WO-2009/029229 | 3/2009 |
| WO | WO-2010/056728 | 5/2010 |
| WO | WO-2010/040006 | 8/2010 |
| WO | WO-2010/151776 | 12/2010 |
| WO | WO-2011/042564 | 4/2011 |
| WO | WO-2011/079176 | 6/2011 |

OTHER PUBLICATIONS

Ahn et al., Dielectrophoretic manipulation of drops for high-speed microluidic sorting devices, Applied Phys Lett 88, 024104 (2006).
Allen et al., High throughput fluorescence polarization: a homogeneous alternative to radioligand binding for cell surface receptors J Biomol Screen. 5(2):63-9 (2000).
Altman et al., Solid-state laser using a rhodamine-doped silica gel compound, IEEE Photonics technology letters 3(3):189-190 (1991).
Amstutz, P. et al., In vitro display technologies: novel developments and applications. Curr Opin Biotechnol, 12, 400-405 (2001).
Anarbaev et al., Klenow fragment and DNA polymerase alpha-primase fromserva calf thymus in water-in-oil microemulsions, Biochim Biophy Acta 1384:315-324 (1998).
Anderson et al., Preparation of a cell-free protein-synthesizing system from wheat germ, Methods Enzymol 101:635-44 (1983).
Anderson, J.E., Restriction endonucleases and modification methylases, Curr. Op. Struct. Biol., 3:24-30 (1993).
Ando, S. et al., PLGA microspheres containing plasmid DNA: preservation of supercoiled DNA via cryopreparation and carbohydrate stabilization, J Pharm Sci, 88(1):126-130 (1999).
Angell et al., Silicon micromechanical devices, Scientific American 248:44-55 (1983).

Anhuf et al., Determination of SMN1 and SMN2 copy number using TaqMan technology, Hum Mutat 22(1):74-78 (2003).
Anna et al., Formation of dispersions using flow focusing in microchannels, Applied Physics Letters,82(3): 364-366 (2003).
Arkin, M.R. et al., Probing the importance of second sphere residues in an esterolytic antibody by phage display, J Mol Biol 284(4):1083-94 (1998).
Armstrong et al., Multiple-Component Condensation Strategies for Combinatorial Library Synthesis, Acc. Chem. Res. 29(3):123-131 (1996).
Ashkin and Dziedzic, Optical trapping and manipulation of viruses and bacteria, Science 235(4795):1517-20 (1987).
Ashkin et al., Optical trapping and manipulation of single cells using infrared laser beams, Nature 330:769-771 (1987).
Atwell, S. & Wells, J.A., Selection for Improved Subtiligases by Phage Display, PNAS 96: 9497-9502(1999).
Auroux, Pierre-Alain et al., Micro Total Analysis Systems. 2. Analytical Standard Operations and Applications, Analytical Chemistry, vol. 74, No. 12, 2002, pp. 2637-2652.
Baccarani et al., *Escherichia coli* dihydrofolate reductase: isolation and characterization of two isozymes, Biochemistry 16(16):3566-72 (1977).
Baez et al., Glutathione transferases catalyse the detoxication of oxidized metabolites (o-quinones) of catecholamines and may serve as an antioxidant system preventing degenerative cellular processes, Biochem. J 324:25-28 (1997).
Bagwe et al, Improved drug delivery using microemulsions: rationale, recent progress, and new horizons, Crit Rev Ther Drug Carr Sys 18(1):77-140 (2001).
Baker, M., Clever PCR: more genotyping, smaller volumes, Nature Methods 7:351-356 (2010).
Ball and Schwartz, CMATRIX: software for physiologically based pharmacokinetic modeling using a symbolic matrix representation system, Comput Biol Med 24(4):269-76 (1994).
Ballantyne and Nixon, Selective Area Metallization by Electron-Beam Controlled Direct Metallic Deposition, J. Vac. Sci. Technol. 10:1094 (1973).
Barany F., The ligase chain reaction in a PCR World, PCR Methods and Applications 1(1):5-16 (1991).
Barony, F. Genetic disease detection and DNA amplification using cloned thermostable ligase, PNAS 88(1): 189-93 (1991).
Baret et al., Fluorescence-activated droplet sorting (FADS): efficient microfluidic cell sorting based on enzymatic activity, Lab on a Chip 9:1850-1858 (2009).
Baret et al., Kinetic aspects of emulsion stabilization by surfactants: a microfluidic analysis, Langmuir 25:6088-6093 (2009).
Bass et al., Hormone Phage: An Enrichment Method for Variant Proteins With Altered Binding Properties, Proteins 8:309-314(1990).
Bauer, J., Advances in cell separation: recent developments in counterflow centrifugal elutriation and continuous flow cell separation, J Chromatography, 722:55-69 (1999).
Beebe et al., Functional hydrogel structures for autonomous flow control inside microfluidic channels, Nature 404:588-590 (2000).
Beer et al., On-Chip, Real-Time, Single-Copy Polymerase Chain Reaction in Picoliter Droplets, Anal. Chem., 2007, v. 79, pp. 847-8475.
Bein, Thomas, Efficient Assays for Combinatorial methods for the Discovery of Catalysts, Agnew. Chem. Int. Ed. 38:3, 323-26 (1999).
Benichou et al., Double Emulsions Stabilized by New Molecular Recognition Hybrids of Natural Polymers, Polym. Adv. Tehcnol 13:1019-1031 (2002).
Benner, S.A., Expanding the genetic lexicon: incorporating non-standard amino acids into proteins by ribosome-based synthesis, Trends Biotechnol 12:158-63 (1994).
Benning, M.M. et al., The binding of substrate analogs to phosphotriesterase. J Biol Chem, 275, 30556-30560 (2000).
Berman et al., An agarose gel electrophoresis assay for the detection of DNA-binding activities in yeast cell extracts, Methods Enzymol 155:528-37 (1987).
Bernath et al, In Vitro Compartmentalization by Double Emulsions: Sorting and Gene Enrichment by Fluorescence Activated Cell Sorting, Anal. Biochem 325:151-157 (2004).

(56) References Cited

OTHER PUBLICATIONS

Bernath et al., Directed evolution of protein inhibitors of DNA-nucleases by in vitro compartmentalization (IVC) and nano-droplet delivery, J. Mol. Biol 345(5):1015-26 (2005).
Betlach, L. et al., A restriction endonuclease analysis of the bacterial plasmid controlling the EcoRI restriction and modification of DNA. Federation Proceedings, 35, 2037-2043 (1976).
Bibette et al., Emulsions: basic principles, Rep. Prog. Phys. 62: 969-1033 (1999).
Bico, Jose et al., Rise of Liquids and Bubbles in Angular Capillary Tubes, Journal of Colloid and Interface Science, vol. 247, 2002, pp. 162-166.
Bico, Jose et al., Self-Propelling Slugs, J. Fluid Mech., vol. 467, 2002, pp. 101-127.
Blattner and Dahlberg, RNA synthesis startpoints in bacteriophage lambda: are the promoter and operator transcribed, Nature New Biol 237(77):227-32 (1972).
Boder et al., Yeast surface display for screening combinatorial polypeptide libraries, Nat Biotechnol 15(6):553-7 (1997).
Bougueleret, L. et al., Characterization of the gene coding for the EcoRV restriction and modification system of *Escherichia coli*, Nucleic Acids Res, 12(8):3659-76 (1984).
Boyum, A., Separation of leukocytes from blood and bone marrow. Introduction, Scand J Clin Lab Invest Suppl 97:7 (1968).
Branebjerg et al., Fast mixing by lamination, MEMS Proceedings 9th Ann WO rkshop, San Diego, Feb. 11-15, 1996, 9:441-446 (1996).
Braslaysky et al., Sequence information can be obtained from single DNA molecules, PNAS 100(7):3960-3964 (2003).
Bringer et al., Microfluidic Systems for Chemical Kinetics That Rely on Chaotic Mixing in Droplets, Philos Transact A Math Phys Eng Sci 362:1-18 (2004).
Brody et al., A self-assembled microlensing rotational probe, Applied Physics Letters, 74:144-46 (1999).
Brown et al., Chemical synthesis and cloning of a tyrosine tRNA gene, Methods Enzymol 68:109-151 (1979).
Bru, R. et al., Catalytic activity of elastase in reverse micelles, Biochem Mol Bio Int, 31(4):685-92 (1993).
Bru, R. et al., Product inhibition of alpha-chymotrypsin in reverse micelles. Eur J Biochem 199(1): 95-103 (1991).
Brummelkamp et al., A system for stable expression of short interfering RNAs in mammalian cells, Science 296(5567):550-3 (2002).
Buckpitt et al.,Hepatic and pulmonary microsomal metabolism of naphthalene to glutathione adducts: factors affecting the relative rates of conjugate formation, J. Pharmacol. Exp. Ther. 231:291-300 (1984).
Buican et al., Automated single-cell manipulation and sorting by light trapping, Applied Optics 26(24):5311-5316 (1987).
Burbaum, J., Miniaturization technologies in HTS: how fast, how small, how soon Drug Discov Today 3:313-322 (1998).
Burns et al., Microfabricated structures for integrated DNA analysis, Proc. Natl. Acad. Sci. USA, May 1996, vol. 93, pp. 5556-5561.
Burns, J.R. et al., The Intensification of Rapid Reactions in Multiphase Systems Using Slug Flow in Capillaries, Lab on a Chip, vol. 1, 2001 pp. 10-15.
Burns, Mark et al., An Integrated Nanoliter DNA Analysis Device, Science, vol. 282, 1998, pp. 484-487.
Byrnes, P.J. et al., Sensitive fluorogenic substrates for the detection of trypsin-like proteases and pancreatic elastase, Anal Biochem, 126:447 (1982).
Cahill et al., Polymerase chain reaction and Q beta replicase amplification, Clin Chem 37(9):1482-5 (1991).
Caldwell, S.R. et al., Limits of diffusion in the hydrolysis of substrates by the phosphodiesterase from Pseudomonas diminuta, Biochemistry, 30: 7438-7444 (1991).
Calvert, P., Inkjet printing for materials and devices, Chem Mater 13: 3299-3305 (2001).
Caruthers, Gene synthesis machines: DNA chemistry and its uses, Science 230:281-285 (1985).

Chakrabarti, A.C. et al., Production of RNA by a polymerase protein encapsulated within phospholipid vesicles, J Mol Evol, 39(6):555-9 (1994).
Chamberlain and Ring, Characterization of T7-specific ribonucleic acid polymerase. 1. General properties of the enzymatic reaction and the template specificity of the enzyme, J Biol Chem 248:2235-44 (1973).
Chan, Emory M. et al., Size-Controlled Growth of CdSe Nanocrystals in Microfluidic Reactors, Nano Letters, vol. 3, No. 2, 2003, pp. 199-201.
Chang and Su, Controlled double emulsification utilizing 3D PDMS microchannels, Journal of Micromechanics and Microengineering 18:1-8 (2008).
Chang, T.M., Recycling of NAD(P) by multienzyme systems immobilized by microencapsulation in artifical cells, Methods Enzymol, 136(67):67-82 (1987).
Chao et al., Control of Concentration and Volume Gradients in Microfluidic Droplet Arrays for Protein Crystallization Screening, 26th Annual International Conference of the IEEE Engineering in Medicine and Biology Society, San Francisco, California Sep. 1-5, 2004.
Chao et al., Droplet Arrays in Microfluidic Channels for Combinatorial Screening Assays, Hilton Head 2004: A Solid State Sensor, Actuator and Microsystems Workshop, Hilton Head Island, South Carolina, Jun. 6-10, 2004.
Chapman et al., In vitro selection of catalytic RNAs, Curr. op. Struct. Biol., 4:618-22 (1994).
Chayen, Crystallization with oils: a new dimension in macromolecular crystal growth Journal of Crystal Growth 196 (1999), pp. 434-441.
Chen et al., Capturing a Photoexcited Molecular Structure Through Time-Domain X-ray Absorption Fine Structure, Science 292(5515):262-264 (2001).
Chen et al., Microfluidic Switch for Embryo and Cell Sorting the 12th International Conference on Solid State Sensors, Actuators, and Microsystems, Boston, MA Jun. 8-12, 2003 Transducers, 1: 659-662 (2003).
Chen-Goodspeed et al., Structural Determinants of the substrate and stereochemical specificity of phosphotriesterase, Biochemistry, 40(5):1325-31 (2001).
Chen-Goodspeed, M. et al., Enhancement, relaxation, and reversal of the stereoselectivity for phosphotriesterase by rational evolution of active site residues, Biochemistry, 40: 1332-1339 (2001b).
Cheng, Z.,et al, Electro flow focusing inmicrofluidic devices, Microfluidics Poster, presented at DBAS, Frontiers in Nanoscience, presented Apr. 10, 2003.
Chetverin and Spirin, Replicable RNA vectors: prospects for cell-free gene amplification, expression, and cloning, Prog Nucleic Acid Res Mol Biol, 51:225-70 (1995).
Chiang, C.M. et al., Expression and purification of general transcription factors by FLAG epitope-tagging and peptide elution, Pept Res, 6: 62-64 (1993).
Chiba et al., Controlled protein delivery from biodegradable tyrosino-containing poly(anhydride-co-imide) microspheres, Biomaterials, 18(13): 893-901 (1997).
Chiou et al., A closed-cylce capillary polymerase chain reaction machine, Analytical Chemistry, American Chemical Society, 73:2018-21 (2001).
Chiu et al., Chemical transformations in individual ultrasmall biomimetic containers, Science, 283: 1892-1895 (1999).
Chou et al., A mirofabricated device for sizing and sorting DNA molecules 96:11-13(1998).
Clackson, T. et al., In vitro selection from protein and peptide libraries, Trends Biotechnol, 12:173-84 (1994).
Clausell-Tormos et al., Droplet-based microfluidic platforms for the encapsulation and screening of Mammalian cells and multicellular organisms, Chem Biol 15(5):427-437 (2008).
Cohen, S. et al., Controlled delivery systems for proteins based on poly(lactic/glycolic acid) microspheres, Pharm Res, 8(6):713-720 (1991).
Collins et al., Optimization of Shear Driven Droplet Generation in a Microluidic Device, ASME International Mechanical Engineering Congress and R&D Expo, Washington (2003).

(56) References Cited

OTHER PUBLICATIONS

Collins, J. et al., Microfluidic flow transducer based on the measurements of electrical admittance, Lab on a Chip, 4:7-10 (2004).
Compton, J., Nucleic acid sequence-based amplification, Nature, 350(6313):91-2 (1991).
Cormack, B.P. et al., FACS-optimized mutants of the green fluorescent protein (GFP), Gene 173(1):33-38 (1996).
Cortesi et al., Production of lipospheres as carriers for bioactive compounds, Biomateials, 23(11): 2283-2294 (2002).
Courrier et al., Reverse water-in-fluorocarbon emulsions and microemulsions obtained with a fluorinated surfactant, Colloids and Surfaces A: Physicochem. Eng. Aspects 244:141-148 (2004).
Craig, D. et al., Fluorescence-based enzymatic assay by capillary electrophoresis laser-induced fluoresence detection for the determininantion of a few alpha-galactosidase molecules, Anal. Biochem. 226: 147 (1995).
Creagh, A.L. et al., Structural and catalytic properties of enzymes in reverse micelles, Enzyme Microb Technol 15(5): 383-92 (1993).
Crosland-Taylor, A Device for Counting Small Particles suspended in a Fluid through a Tube, Nature 171:37-38 (1953).
Crowley, J. M., Electrical breakdown of bimolecular lipid membranes as an electromechanical instability, Biophys J. 13(7):711-724 (1973).
Cull, M.G. et al., Screening for receptor ligands using large libraries of peptides linked to the C terminus of the lac repressor, PNAS 89:1865-9 (1992).
Curran, D.P., Strategy-level separations in organic synthesis: from planning to practice. Angew Chem Int Ed, 37: 1174-11-96 (1998).
Czarnik, A.W., Encoding methods for combinatorial chemistry, Curr Opin Chem Biol 1:60-66 (1997).
Dankwardt et al., Combinatorial synthesis of small-molecule libraries using 3-amino-5-hydroxybenzoic acid, 1:113-120 (1995).
Davis, J.A. et al., Deterministic hydrodynamics: Taking blood apart, PNAS 103:14779-14784 (2006).
Davis, S.S. et al., Multiple emulsions as targetable delivery systems, Methods in Enzymology, 149: 51-64 (1987).
de Gans, B.J. et al., Inkjet printing of polymers: state of the art and future developments, Advanced materials, 16: 203-213 (2004).
De-Bashan, L. E. et al., Removal of ammonium and phosphorus ions from synthetic wastewater by the microalgae Chlorella vulgaris coimmobilized in alginate beads with the microalgae growth-promoting bacterium Azospirillum brasilense, Water Research 36(2002),pp. 2941-2948.
Delagrave, S. et al., Red-shifted excitation mutants of the green fluorescent protein, Biotechnology 13(2):151-4 (1995).
DelRaso, In vitro methodologies for enhanced toxicity testing, Toxicol. Lett. 68:91-99 (1993).
Demartis et al., A strategy for the isolation of catalytic activities from repertoires of enzymes displayed on phage, J. Mol. Biol 286:617-633 (1999).
Dickinson, E., Emulsions and droplet size control, Wedlock, D.J., Ed., in Controlled Particle Droplet and Bubble Formulation, ButterWO rth-Heine-mann, 191-257 (1994).
DiMatteo, et al., Genetic conversion of an SMN2 gene to SMN1: A novel approach to the treatment of spinal muscular atrophy, Exp Cell Res. 314(4):878-886 (2008).
Dinsmore et al., Colioidosomes: Selectively Permeable Capsules Composed of Colloidal Particles, Science 298(5595):1006-1009. (2002).
Dittrich et al., A new embedded process for compartmentalized cell-free protein expression and on-line detection in microfluidic devices, Chembiochem 6(5):811-814 (2005).
Doi et al., In vitro selection of restriction endonucleases by in vitro compartmentilization, Nucleic Acids Res, 32(12): e95 (2004).
Doi, N. and Yanagawa, H. Stable: protein-DNA fusion system for screening of combinatorial protein libraries in vitro, FEBS Lett., 457: 227-230 (1999).
Doman, T.N. et al., Molecular docking and high-throughput screening for novel inhibitors of protein tyrosine phosphatase-1B, J Med Chem, 45: 2213-2221 (2002).
Domling A., Recent advances in isocyanide-based multicomponent chemistry, Curr Opin Chem Biol, 6(3):306-13 (2002).
Domling and Ugi, Multicomponent Reactions with Isocyanides, Angew Chem Int Ed 39(18):3168-3210 (2000).
Dove et al., In Brief, Nature Biotechnology 20:1213 (2002).
Dower et al., High efficiency transformation of E. coli by high voltage electroporation, Nucleic Acids Res 16:6127-6145 (1988).
Dressman et al., Transforming single DNA molecules into fluorescent magnetic particles for detection and enumeration of genetic variations, PNAS 100:8817-22 (2003).
Dreyfus et al., Ordered and disordered patterns in two phase flows in microchannels, Phys Rev Lett 90(14):144505-1-144505-4 (2003).
Drmanac et al., Sequencing by hybridization: towards an automated sequencing of one million M13 clones arrayed on membranes, Elctrophoresis 13:566-573 (1992).
Dubertret et al., In vivo imaging of quantum dots encapsulated in phospholipid micelles, Science, 298: 1759-1762 (2002).
Duffy et al., Rapid Protyping of Microfluidic Systems and Polydimethylsiloxane, Anal Chem 70:474-480 (1998).
Duggleby, R. G. Enzyme Kinetics and Mechanisms, Pt D. Academic Press 249:61-90 (1995).
Dumas, D.P., Purification and properties of the phosphotriesterase from Psuedomonas diminuta, J Biol Chem 264: 19659-19665 (1989).
Eckert and Kunkel, DNA polymerase fidelity and the polymerase chain reaction, Genome Res 1:17-24 (1991).
Edd et al., Controlled encapsulation of single-cells into monodisperse picolitre drops, Lab Chip 8(8):1262-1264 (2008).
Edel, Joshua B. et al., Microfluidic Routes to the Controlled Production of Nanopaticles, Chemical Communications, 2002 pp. 1136-1137.
Edris et al., Encapsulation of orange oil in a spray dried double emulsion, Nahrung/Food, 45(2):133-137 (2001).
Effenhauser et al., Glass chips for high-speed capillary electrophoresis separations with submicrometer plate heights, Anal Chem 65:2637-2642 (1993).
Eggers, Jens et al., Coalescence of Liquid Drops, J. Fluid Mech., vol. 401, 1999, pp. 293-310.
Ehrig, T. et al., Green-fluorescent protein mutants with altered fluorescence excitation spectra, Febs Lett, 367(2):163-66 (1995).
Eigen et al., hypercycles and compartments: compartments assists— but does not replace—hypercyclic organization of early genetic information, J Theor Biol, 85:407-11 (1980).
Eigen et al., The hypercycle: coupling of RNA and protein biosynthesis in the infection cycle of an RNA bacteriophage, Biochemistry, 30:11005-18 (1991).
Eigen, Wie entsteht information Prinzipien der selbstorganisation in der biologie, Berichte der punsen-gesellschaft fur physikalische chemi, 80:1059-81 (1976).
Ellington and Szostak, In vitro selection of RNA molecules that bind specific ligands, Nature, 346:818-822 (1990).
Ellman et al., Biosynthetic method for introducing unnatural amino acids site-specifically into proteins, Methods Enzymol, 202:301-36 (1991).
Endo et al. Kinetic determination of trace cobalt by visual autocatalytic indication, Talanta 47:349-353 (1998).
Endo et al., Autocatalytic decomposition of cobalt complexes as an indicator system for the determination of trace amounts of cobalt and effectors, Analyst 121:391-394 (1996).
Eow et al., Electrocoalesce-separators for the separation of aqueous drops from a flowing dielectric viscous liquid, Separation and Purification Tech 29:63-77 (2002).
Eow et al., Electrostatic enhancement of coalescence of water droplets in oil: a review of the technology, Chemical Engineeing Journal 85:357-368 (2002).
Eow et al., Motion, deformation and break-up of aqueous drops in oils under high electric field strengths, Chemical Eng Proc 42:259-272 (2003).
Eow et al., The behavior of a liquid-liquid interface and drop-interface coalescence under the influence of an electric field, Colloids and Surfaces A: Physiochem. Eng. Aspects 215:101-123 (2003).

(56) References Cited

OTHER PUBLICATIONS

Eow, et al. Electrostatic and hydrodynamic separation of aqueous drops in a flowing viscous oil, Chemical Eng Proc 41:649-657 (2002).
Extended European Search Report for EP 10181911.8 dated Jun. 1, 2011 (7 pages).
Extended European Search Report for EP 10184514.7 dated Dec. 20, 2010 (5 pages).
Faca et al., A mouse to human search for plasma proteome changes associated with pancreatic tumor development, PLoS Med 5(6):e123 (2008).
Fahy et al., Self-sustained sequence replication (3SR): an isothermal transcription-based amplification system alternative to PCR, PCR Methods Appl 1:25-33 (1991).
Fan and Harrison, Micromachining of capillary electrophoresis injectors and separators on glass chips and evaluation of flow at capillary intersections, Anal Chem 66:177-184 (1994).
Fastrez, J., In vivo versus in vitro screening or selection for catalytic activity in enzymes and abzymes, Mol Biotechnol 7(1):37-55 (1997).
Fettinger et al., Stacked modules for micro flow systems in chemical analysis: concept and studies using an enlarged model, Sens Actuat B. 17:19-25 (1993).
Fiedler et al., Dielectrophoretic sorting of particles and cells in a microsystem, Anal Chem 70(9):1909-1915 (1998).
Field, J. et al., Purification of a RAS-responsive adenylyl cyclase complex from *Saccharomyces cervisiae* by use of an epitope addition method. Mol Cell Biol, 8: 2159-2165 (1988).
Fields, S. and Song, O., A novel genetic system to detect protein-protein interactions, Nature 340(6230): 245-6 (1989).
Filella et al., TAG-72, CA 19.9 and CEA as tumor markers in gastric cancer, Acta Oncol. 33(7):747-751 (1994).
Finch, C.A., Encapsulation and controlled release, Spec Publ R Soc Chem, 138:35 (1993).
Finch, C.A., Industrial Microencapsulation: Polymers for Microcapsule Walls, 1-12 in Encapsulation and Controlled Release, Woodhead Publishing (1993).
Fire & Xu, Rolling replication of short DNA circles, PNAS 92(10):4641-5 (1995).
Firestine, S.M. et al., Using an AraC-based three hybrid system to detect biocatalysts in vivo, Nat Biotechnol 18: 544-547 (2000).
Fisch et al., A strategy of exon shuffling for making large peptide repertoires displayed on filamentous bacteriophage, PNAS 93:7761-6 (1996).
Fisher et al., Cell Encapsulation on a Microfluidic Platform, The Eighth International Conference on Miniaturised Systems for Chemistry and Life Scieces, MicroTAS 2004, Sep. 26-30, Malmo, Sweden.
Fletcher et al., Micro reactors: principles and applications in organic synthesis, Tetrahedron 58:4735-4757 (2002).
Fluri et al., Integrated capillary electrophoresis devices with an efficient postcolumn reactor in planar quartz and glass chips, Anal Chem 68:4285-4290 (1996).
Fornusek, L. et al., Polymeric microspheres as diagnostic tools for cell surface marker tracing, Crit Rev Ther Drug Carrier Syst, 2:137-74 (1986).
Fowler, Enhancement of Mixing by Droplet-Based Microfluidics, Int Conf MEMS 97-100 (2002).
Freese, E., The specific mutagenic effect of base analogues on Phage T4, J Mol Biol, 1: 87 (1959).
Frenz et al., Reliable microfluidic on-chip incubation of droplets in delay-lines, Lab on a Chip 9:1344-1348 (2008).
Fu et al., A microfabricated fluorescence-activated cell sorter, Nature Biotechnology, 17(11):1109-1111 (1999).
Fu et al., An Integrated Microfabricated Cell Sorter, Anal. Chem., 74: 2451-2457 (2002).
Fulton et al., Advanced multiplexed analysis with the FlowMetrix system, Clin Chem 43:1749-1756 (1997).
Fulwyler, Electronic Separation of Biological Cells by Volume, Science 150(3698):910-911 (1965).

Gallarate et al., On the stability of ascorbic acid in emulsified systems for topical and cosmetic use, Int J Pharm 188(2):233-241 (1999).
Ganan-Calvo, A.M., Perfectly Monodisperse Microbubbling by Capillary Flow Focusing, Phys Rev Lett 87(27): 274501-1-4 (2001).
Ganan-Calvo, Generation of Steady Liquid Microthreads and Micron-Sized Monodisperse Sprays and Gas Streams, Phys Rev Lett 80(2):285-288 (1998).
Garcia-Ruiz et al. A super-saturation wave of protein crystallization, J. Crystal Growth, 2001, v232, pp. 149-155.
Garcia-Ruiz et al., Investigation on protein crystal growth by the gel acupuncture method{, Acta, Cryst., 1994, D50, 99. pp. 484-490.
Garstecki, et al., Formation of monodisperse bubbles in a microfluidic flow-focusing device, Appl Phys Lett 85(13):2649-2651 (2004).
Gasperlin et al., The structure elucidation of semisolid w/o emulsion systems containing silicone surfactant, Intl J Pharm, 107:51-6 (1994).
Gasperlin et al., Viscosity prediction of lipophillic semisolid emulsion systems by neural network modeling, Intl J Pharm, 196:37-50 (2000).
Georgiou et al., Display of heterologous proteins on the surface of microorganisms: from the screenign of combinatiorial libraires to live recombinant vaccines. Nat Biotechnol 15(1), 29-34 (1997).
Georgiou, G., Analysis of large libraries of protein mutants using flow cytometry, Adv Protein Chem, 55: 293-315 (2000).
Gerdts et al., A Synthetic Reaction NetWork: Chemical Amplification Using Nonequilibrium Autocatalytic Reactions Coupled in Time, J. Am. Chem. Soc 126:6327-6331 (2004).
Ghadessy et al., Directed Evolution of Polymerase Function by Compartmentalized Self-Replication, PNSAS 98(8): 4552-4557 (2001).
Gibbs et al., Detection of single DNA base differences by competitive oligonucleotide priming, Nucleic Acids Res. 17(7): 2437-48 (1989).
Gilliland, G., Analysis of cytokine mRNA and DNA: Detection and quantitation by competitive polymerase chain reaction, PNAS, 87(7):2725-9 (1990).
Giusti et al., Synthesis and characterization of 5' fluorescent dye labeled oligonucleotides, Genome Res 2:223-227 (1993).
Gold et al., Diversity of Oligonucleotide Functions Annu Rev Biochem, 64: 763-97 (1995).
Goodall, J. L. et al., Operation of Mixed-Culture Immobilized Cell Reactors for the Metabolism of Meta- and Para-Nitrobenzoate by *Comamonas* Sp. JS46 and *Comamonas* Sp. JS47, Biotechnology and Bioengineering, vol. 59, No. 1, Jul. 5, 1998, pp. 21-27.
Gordon and Balasubramanian, Solid phase synthesis—designer linkers for combinatorial chemistry: a review, J. Chem. Technol. Biotechnol., 74(9):835-851 (1999).
Grasland-Mongrain et al., Droplet coalescence in microfluidic devices, 30 pages (Jul. 2003) From internet: http://www.eleves.ens.fr/home/grasland/rapports/stage4.pdf.
Green, R. and Szostak, J.W., Selection of a Ribozyme That Functions as a Superior Template in a Self Copying Reaction, Science, 258: 1910-5 (1992).
Gregoriadis, G., Enzyme entrapment in liposomes, Methods Enzymol 44:218-227 (1976).
Griffiths et al., Directed evolution of an extremely fast phosphotriesterase by in vitro compartmentalization, EMBO J, 22:24-35 (2003).
Griffiths et al., Isolation of high affinity human antibodies directly from large synthetic repertoires, EMBO J 13(14):3245-60 (1994).
Griffiths et al., Man-made enzymes-from design to in vitro compartmentalisation, Curr Opin Biotechnol 11:338-353 (2000).
Griffiths, A., and Tawfik, D., Miniaturising the laboratory in emulsion droplets, Trend Biotech 24(9):395-402 (2006).
Griffiths, A.D. et al., Strategies for selection of antibodies by phage display, Curr Opin Biotechnol, 9:102-8 (1998).
Guatelli, J.C. et al., Isothermal, in vitro amplification of nucleic acids by a multienzyme reaction modeled after retroviral replication, PNAS, 87(5):1874-8 (1990).
Guixe et al., Ligand-Induced Conformational Transitions in *Escherichia coli* Phosphofructokinase 2: Evidence for an Allosteric Site for MgATP2n, Biochem., 37: 13269-12375 (1998).

(56) References Cited

OTHER PUBLICATIONS

Gupta, K.C., et al., A general method for the synthesis of 3'-sulfhydryl and phosphate group containing oligonucleotides, Nucl Acids Res 19 (11): 3019-3026 (1991).

Haber et al., Activity and spectroscopic properties of bovine liver catalase in sodium bis(2-ethylhexyl) sulfosuccinate/isooctane reverse micelles, Eur J Biochem 217(2): 567-73 (1993).

Habig and Jakoby, Assays for differentiation of glutathione S-transferases, Methods in Enzymology, 77: 398-405 (1981).

Hadd et al., Microchip Device for Performing Enzyme Assays, Anal. Chem 69(17): 3407-3412 (1997).

Haddad et al., A methodology for solving physiologically based pharmacokinetic models without the use of simulation software, Toxicol Lett. 85(2): 113-26 (1996).

Hagar and Spitzer, The effect of endotoxemia on concanavalin A induced alterations in cytoplasmic free calcium in rat spleen cells as determined with Fluo-3, Cell Calcium 13:123-130 (1992).

Hai et al., Investigation on the release of fluorescent markers from the w/o/w emulsions by fluorescence-activated cell sorter, J Control Release, 96(3): 393-402 (2004).

Haies et al., Morphometric study of rat lung cells. I. Numerical and dimensional characteristics of parenchymal cell population, Am. Rev. Respir. Dis. 123:533-54 (1981).

Hall, Experimental evolution of Ebg enzyme provides clues about the evolution of catalysis and to evolutionary potential, FEMS Microbiol Lett, 174(1):1-8 (1999).

Hall, The EBG system of E. coli: origin and evolution of a novel beta-galactosidase for the metabolism of lactose, Genetica 118(2-3):143-56 (2003).

Han et al., Quantum-dot-tagged Microbeads for Multiplexed Optical Coding of Biomolecules, Nat Biotech 19(7): 631-635 (2001).

Handen, J.S., High-throughput screening—challenges for the future, Drug Discov World, 47-50 (2002).

Handique, K. et al., On-Chip Thermopneumatic Pressure for Discrete Drop Pumping, Analytical Chemistry, vol. 73, 2001, pp. 1831-1838.

Hanes et al., Degradation of porous poly(anhydide-co-imide) microspheres and implication for controlled macromolecule delivery, Biomaterials, 19(1-3): 163-172(1998).

Hanes et al., In vitro selection and evolution of functional proteins by using ribosome display, PNAS 94:4937-42 (1997).

Hansen et al., A robust and scalable microfluidic metering method that allows protein crystal growth by free interface diffusion, PNAS 99(26):16531-16536 (2002).

Harada et al., Monoclonal antibody G6K12 specific for membrane-associated differentiation marker of human stratified squamous epithelia and squamous cell carcinoma, J. Oral Pathol. Med 22(4):145-152 (1993).

Harder, K.W. et al., Characterization and kinetic analysis of the intracellular domain of human protein tyrosine phosphatase beta (HPTP beta) using synthetic phosphopeptides, Biochem J 298 (Pt 2): 395-401 (1994).

Harries et al., A Numerical Model for Segmented Flow in a Microreactor, Int J of Heat and Mass Transfer, 46:3313-3322 (2006).

Harris et al., Single-molecule DNA sequencing of a viral genome, Science 320(5872):106-109 (2008).

Harrison et al., Micromachining a miniaturized capillary electrophoresis-based chemical analysis system on a chip, Science 261(5123):895-897 (1993).

Hasina et al., Plasminogen activator inhibitor-2: a molecular biomarker for head and neck cancer progression, Cancer Research 63:555-559 (2003).

Haynes Principles of Digital PCR and Measurement IssueOct. 15, 2012.

Hayward et al., Dewetting Instability during the Formation of Polymersomes from BloceCopolymer-Stabilized Double Emulsions, Langmuir, 22(10): 4457-4461 (2006).

He et al., Selective encapsulation of single cells and subcellular organelles into picoliter- and femtoliter—volume droplets, Anal Chem 77(6):1539-1544 (2005).

Heim et al., Engineering Green Fluorescent Protein for Improved Brightness, Longer Wavelengths and Fluorescence Response Energy Transfer, Carr. Biol, 6(2): 178-182 (1996).

Hellman et al., Differential tissue-specific protein markers of vaginal carcinoma, Br J Cancer, 100(8): 1303-131 (2009).

Hergenrother et al., Small-Molecule Microarrays: Covalent Attachment and Screening of Alcohol-Containing Small Molecules on Glass Slides, J. Am. Chem. Soc, 122: 7849-7850 (2000).

Hildebrand et al., Liquid-Liquid Solubility of Perfluoromethylcyclohexane with Benzene, Carbon Tetrachloride, Chlorobenzene, Chloroform and Toluene, J. Am. Chem. Soc, 71: 22-25 (1949).

Hjelmfelt et al, Pattern-Recognition in Coupled Chemical Kinetic Systems, Science, 260(5106):335-337 (1993).

Ho, S.N. et al., Site-directed mutageneiss by overlap extension using the polymerase chain reaction, Gene, 77(1):51-9 (1989).

Hoang, Physiologically based pharmacokinetic models: mathematical fundamentals and simulation implementations, Toxicol Lett 79(1-3):99-106 (1995).

Hochuli et al., New metal chelate adsorbent selective for proteins and peptides containing neighbouring histidine residues, J Chromatogr 411: 177-84 (1987).

Holmes et al., Reagents for Combinatorial Organic Synthesis: Development of a New O-Nitrobenzyl Photolabile Linder for Solid Phase Synthesis, J. OrgChem., 60: 2318-2319(1995).

Hong, S.B. et al., Stereochemical constraints on the substrate specificity of phosphodiesterase, Biochemistry, 38: 1159-1165 (1999).

Hoogenboom et al., Multi-subunit proteins on the surface of filamentous phage: methodologies for displaying antibody (Fab) heavy and light chains, Nucl Acids Res., 91: 4133-4137 (1991).

Hoogenboom, H.R., Designing and optimizing library selection strategies for generating high-affinity antibodies, Trends Biotechnol, 15:62-70 (1997).

Hopfinger & Lasheras, Explosive Breakup of a Liquid Jet by a Swirling Coaxial Jet, Physics of Fluids 8(7):1696-1700 (1996).

Hopman et al., Rapid synthesis of biotin-, digoxigenin-, trinitrophenyl-, and fluorochrome-labeled tyramides and their application for In situ hybridization using CARD amplification, J of Histochem and Cytochem, 46(6):771-77 (1998).

Horton et al., Engineering hybrid genes without the use of restriction enzymes: gene splicing by overlap extension, Gene 77(1), 61-8 (1989).

Hosokawa, Kazuo et al., Handling of Picoliter Liquid Samples in a Poly(dimethylsiloxane)-Based Microfluidic Device, Analytical Chemistry, vol. 71, No. 20, 1999 pp. 4781-4785.

Hsu et al., Comparison of process parameters for microencapsulation of plasmid DNA in poly(D, L-lactic-co-glycolic acid microspheres, J Drug Target, 7:313-23 (1999).

Huang L. R. et al., Continuous particle separation through deterministic lateral displacement, Science 304(5673):987-990 (2004).

Huang, Z. et al., A sensitive competitive ELISA for 2,4-dinitrophenol using 3,6-fluorescein diphosphate as a fluorogenic substrate, J Immunol Meth, 149:261 (1992).

Huang, Z.J., Kinetic assay of fluorescein mono-beta-D-galactosidase hydrolysis by beta-galactosidase: a front-face measurement for strongly absorbing fluorogenic substrates, Biochemistry, 30:8530-4 (1991).

Hubert et al. Data Concordance from a Comparison between Filter Binding and Fluorescence Polarization Assay Formats for Identification of RUOCK-II Inhibitors, J biomol Screen 8(4):399-409 (2003).

Huebner, A. et al., Quantitative detection of protein expression in single cells using droplet microfluidics, Chem Com 12:1218-1220 (2007).

Hung et al., Optimization of Droplet Generation by controlling PDMS Surface Hydrophobicity, 2004 ASME International Mechanical Engineering Congrees and RD&D Expo, Nov. 13-19, Anaheim, CA (2004).

Hung, et al, Controlled Droplet Fusion in Microfluidic Devices, MicroTAS 2004, Sep. 26-30, Malmo, Sweden (2004).

(56) References Cited

OTHER PUBLICATIONS

Hutchison et al., Cell-free cloning using Phi29 polymerase, PNAS 102(48):17332-17336 (2005).
Ibrahim, S.F. et al., High-speed cell sorting: fundamentals and recent advances, Curr Opin Biotchnol, 14(1):5-12 (2003).
Ikeda et al., Bioactivation of tegafur to 5-fluorouracil is catalyzed by cytochrome P-450 2A6 in human liver microsomes in vitro, Clin Cancer Res 6(11):4409-4415 (2000).
Inai et al., Immunohistochemical detection of an enamel protein-related epitope in rat bone at an early stage of osteogenesis, Histochemistry 99(5):335-362 (1993).
International Preliminary Report of Patentability for PCTUS2010061741 dated Sep. 16, 2011(4 pages).
International Preliminary Report on Patentability dated Sep. 20, 2007, for PCT/US2006/007772.
International Search Report and Written Opinion for PCT/US2009/050931 dated Nov. 26, 2009 (3 pages).
International Search Report and Written Opinion for PCTUS1154353 dated Apr. 20, 2012 (34 pages).
International Search Report and Written Opinion for PCTUS12024745 dated May 11, 2012 (21 pages).
International Search Report and Written Opinion for PCTUS1224741 dated Jun. 12, 2012 (12 pages).
International Search Report and Written Opinion for PCTUS125499 dated May 29, 2012 (10 pages).
International Search Report and Written Opinion in PCT/EP2010/065188 dated Jan. 12, 2011 (7 pages).
International Search Report and Written Opinion in PCT/US11/24615 dated Jul. 25, 2011 (37 pages).
International Search Report and Written Opinion in PCT/US2004/010903 dated Dec. 20, 2004 (16 pages).
International Search Report and Written Opinion in PCT/US2006/021286 dated Sep. 14, 2007 (16 pages).
International Search Report and Written Opinion in PCT/US2007/002063 dated Nov. 15, 2007 (20 pages).
International Search Report in PCT/US01/18400 dated Jan. 28, 2005 ( 37 pages).
Ismagilov, Integrated Microfluidic Systems, Angew. Chem. Int. Ed 42:4130-4132 (2003).
Janda, et al, Chemical selection for catalysis in combinatorial antibody libraries, Science, 275:945-948 (1997).
Jang et al., Controllable delivery of non-viral DNA from porous scaffold, J Controlled Release 86(1):157-168 (2003).
Japanese Office Action for JP 2006-509830 dated Jun. 1, 2011 (4 pages).
Jermutus et al., Recent advances in producing and selecting functional proteins by using cell-free translation, Curr Opin Biotechnol 9(5): 534-48 (1998).
Jestin et al., A Method for the Selection of Catalytic Activity Using Phage Display and Proximity Coupling, Agnew. Chem. Int. Ed. Engi. 38(8):1124-1127 (1999).
Jo, et al, Encapsulation of Bovine Serum Albumin in Temperature-Programmed Shell-in-Shell Structures, Macromol. Rapid Comm 24:957-962 (2003).
Joerger et al., Analyte detection with DNA-labeled antibodies and polymerase chain reaction, Clin. Chem. 41(9):1371-7 (1995).
Johannsson et al., Amplification by Second Enzymes, in ELISA and Other Solid Phase Immunoassays, Kemeny et al (ed.), Chapter 4, pp. 85-106 John Wiley (1988).
Johannsson, A., Heterogeneous Enzyme Immunoassays, in Principles and Practice of Immunoassay, pp. 295-325 Stockton Press (1991).
Johnson, T.O. et al., Protein tyrosine phosphatase 1B inhibitors for diabetes, Nature Review Drug Discovery 1, 696-709 (2002).
Jones et al. Glowing jellyfish, luminescence and a molecule called coelenterazine, Trends Biotechnol. 17(12):477-81 (1999).
Jones, L.J. et al., Quenched BODIPY dye-labeled casein substrates for the assay of protease activity by direct fluorescence measurement, Anal Biochem, 251:144 (1997).
Joo et al., Laboratory evolution of peroxide-mediated cytochrome P450 hydroxylaion, Nature 399:670 (1999).
Joos et al., Covalent attachment of hybridizable oligonucleotides to glass supports, Analytical Biochemistry 247:96-101 (1997).
Joyce, G.F., In vitro Evolution of Nucleic Acids, Curr. Opp. Structural Biol, 4: 331-336 (1994).
Kadir and Moore, Haem binding to horse spleen ferritin, Febs Lett, 276: 81-4 (1990).
Kallen, R.G. et al., The mechanism of the condensation of formaldehyde with tetrahydrofolic acid, J. Biol. Chem., 241:5851-63 (1966).
Kambara et al., Optimization of Parameters in a DNA Sequenator Using Fluorescence Detection, Nature Biotechnology 6:816-821 (1988).
Kamensky et al., Spectrophotometer: new instrument for ultrarapid cell analysis, Science 150(3696):630-631 (1965).
Kanouni et al., Preparation of a stable double emulsion (W1/0/W2): role of the interfacial films on the stability of the system, Adv. Collid. lnterf. Sci., 99(3): 229-254 (2002).
Katanaev et al., Viral Q beta RNA as a high expression vector for mRNA translation in a cell-free system, Febs Lett, 359:89-92 (1995).
Katsura et al., Indirect micromanipulation of single molecules in water-in-oil emulsion, Electrophoresis, 22:289-93 (2001).
Kawakatsu et al., Regular-sized cell creation in microchannel emulsification by visual microprocessing method, Journal of the American Oil ChemistS Society, 74:317-21 (1997).
Keana J. & Cai, S. X., New reagents for photoaffinity labeling: synthesis and photolysis of functionalized perfluorophenyl azides, J. Org. Chem.55(11):3640-3647 (1990).
Keefe, A.D. et al., Functional proteins from a random-sequence library, Nature, 410: 715-718 (2001).
Keij et al., High-Speed Photodamage Cell Selection Using a Frequency-Doubled Argon Ion Laser, Cytometry, 19(3): 209-216 (1995).
Keij, J.F., et al., High-speed photodamage cell sorting: An evaluation of the Zapper prototype, Methods in cell biology, 42: 371-358 (1994).
Kelly et al., Miniaturizing chemistry and biology in microdroplets, Chem Commun 18:1773-1788 (2007).
Kerker, M., Elastic and inelastic light scattering in flow cytometry, Cytometry, 4:1-10 (1983).
Khandjian, UV crosslinking of RNA to nylon membrane enhances hybridization signals, Mol. Bio. Rep. 11: 107-115 (1986).
Kim et al., Comparative study on sustained release of human growth hormone from semi-crystalline poly(L-lactic acid) and amorphous poly(D,L-lactic-co-glycolic acid) microspheres: morphological effect on protein release, Journal of Controlled Release, 98(1):115-125 (2004).
Kim S. et al, Type II quantum dots: CdTe/CdSe (core/shell) and CdSe/ZnTe (core/shell) heterostructures, J. Am Chem Soc. 125:11466-11467 (2003).
Kircher et al., High-throughput DNA sequencing-concepts and limitations, Bioessays 32(6):524-536 (2010).
Kiss et al., High-throughput quantitative polymerase chain reaction in picoliter droplets, Anal. Chem 80:8975-8981 (2008).
Kitagawa et al., Manipulation of a single cell with microcapillary tubing based on its electrophoretic mobility, Electrophoresis 16:1364-1368 (1995).
Klug and Famulok, All you wanted to know about selex, Molecular Biology Reports, 20:97-107 (1994).
Klug and Schwabe, Protein motifs 5. Zinc fingers, FASEB J 9(8):597-604 (1995).
Klug, A., Gene Regulatory Proteins and Their Interaction with DNA, Ann NY Acad Sci, 758:143-60 (1995).
Knaak et al., Development of partition coefficients, Vmax and Km values, and allometric relationships, Toxicol Lett. 79(I-3):87-98 (1995).
Knight, James B., Hydrodynamic Focusing on a Silicon Chip: Mixing Nanoliters in Microseconds, Physical Review Lett 80(17):3863-3866 (1998).

(56) References Cited

OTHER PUBLICATIONS

Kojima et al. PCR amplification from single DNA molecules on magnetic beads in emulsion: application for high-throughput screening of transcription factor targets. Nucleic Acids Res. 33:e150 (2005).
Kolb et al., Cotranslational folding of proteins, Biochem Cell Biol, 73:1217-20 (1995).
Komatsu et al., Roles of cytochromes P450 1A2, 2A6, and 2C8 in 5-fluorouracil formation rom tegafur, an anticancer prodrug, in human liver microsomes. Drug Met. Disp., 28:1457-1463 (2001).
Kopp et al., Chemical amplification: continuous flow PCR on a chip, Science, 280:1046-48 (1998).
Koster et al., Drop-based microfluidic devices for encapsulation of single cells, Lab on a Chip 8:1110-1115 (2008).
Kowalczykowski et al., Biochemistry of homologous recombination in *Escherichia coli*, Microbiol Rev 58(3):401-65 (1994).
Krafft et al., Emulsions and microemulsions with a fluorocarbon phase, Colloid and Interface Science 8(3):251-258 (2003).
Krafft, Fluorocarbons and fluorinated amphiphiles in drug delivery and biomedical research, Adv Rev Drug Disc 47:209-228 (2001).
Krafft et al., Synthesis and preliminary data on the biocompatibility and emulsifying properties of perfluoroalkylated phosphoramidates as injectable surfactants, Eur. J. Med. Chem., 26:545-550 (1991).
Kralj et al., Surfactant-enhanced liquid-liquid extraction in microfluidic channels with inline electric-field enhanced coalescence, Lab Chip 5:531-535 (2005).
Kricka and Wilding, Microchip PCR, Anal Bioanal Chem 377(5):820-825 (2003).
Kricka and Wilding, Micromachining: a new direction for clinical analyzers, Pure and Applied Chemistry 68(10):1831-1836 (1996).
Krumdiek, C.L. et al., Solid-phase synthesis of pteroylpolyglutamates, Methods Enzymol, 524-29 (1980).
Kumar, A. et al., Activity and kinetic characteristics of glutathione reductase in vitro in reverse micellar waterpool, Biochem Biophys Acta, 996(1-2):1-6 (1989).
Lage et al., Whole genome analysis of genetic alterations in small DNA samples using hyperbranched strand displacement amplification and array-CGH. Genome Res. 13: 294-307 (2003).
Lamprecht et al., pH-sensitive microsphere delivery increases oral bioavailability of calcitonin, Journal of Controlled Release, 98(1):1-9(2004).
Lancet, D. et al., Probability model for molecular recognition in biuological receptor repertoirs: significance to the olfactory system, PNAS, 90(8):3715-9 (1993).
Landergren et al., A ligase mediated gene detection technique. Science 241(4869):1077-80 (1988).
Lasheras, et al., Breakup and Atomization of a Round Water Jet by a High Speed Annular Air Jet, J Fluid Mechanics 357:351-379 (1998).
Leary et al., Application of Advanced Cytometric and Molecular Technologies to Minimal Residual Disease Monitoring, Proceedings of SPIE 3913:36-44 (2000).
Lee et al, Investigating the target recognition of DNA cytosine-5 methyltransferase HhaI by library selection using in vitro compartmentalisation (IVC), Nucleic Acids Res 30:4937-4944 (2002).
Lee et al., Circulating flows inside a drop under time-periodic non-uniform electric fields, Phys Fuilds 12(8):1899-1910 (2000).
Lee, et al, Effective Formation of Silicone-in-Fluorocarbon-in-Water Double Emulsions: Studies on Droplet Morphology and Stability, Journal of Dispersion Sci Tech 23(4):491-497(2002).
Lee, et al, Preparation of Silica Paticles Encapsulating Retinol Using O/W/O Multiple Emulsions, Journal of Colloid and Interface Science, 240(1): 83-89 (2001).
Lemof, et al, An AC Magnetohydrodynamic Microfluidic Switch for Micro Total Analysis Systems, Biomedical Microdevices, 5(I):55-60 (2003).
Lesley et al., Use of in vitro protein synthesis from PCR-generated templates to study interaction of E coli transcription factors with core RNA polymerase, J Biol Chem 266(4):2632-8 (1991).
Lesley, S.A., Preparation and use of E. coli S-30 extracts, Methods Mol Biol, 37:265-78 (1995).
Leung et al., A method for random mutagenesis of a defined DNA segment using a modified polymerase chain reaction. Technique 1:11-15 (1989).
Li and Harrison, Transport, Manipulation, and Reaction of Biological Cells On-Chip Using Electrokinetic Effects, Analytical Chemistry 69(8):1564-1568 (1997).
Li et al., Nanoliter microfluidic hybrid method for simultaneous screening and optimization validated with crystallization of membrane proteins, PNAS 103: 19243-19248 (2006).
Li et al., Single-step procedure for labeling DNA strand breaks with fllourescein-or Bodipy-conjugated deoxynucleotides: detection of apoptosis and bromodeoxyuridine incorporation. Cytometry 20:172-180 (1995).
Liao et al., Isolation of a thermostable enzyme variant by cloning and selection in a thermophile, PNAS 83:576-80 (1986).
Lim et al., Microencapsulated islets as bioartificial endocrine pancreas, Science 210(4472):908-10 (1980).
Link et al, Geometrically Mediated Breakup of Drops in Microfluidic Devices, Phys. Rev. Lett., 92(5): 054503-1 thru 054503-4 (2004).
Link et al., Electric control droplets in microfluidic devices, Angew Chem Int Ed 45:2556-2560 (2006).
Lipinski et al., Experimental and Computational Approaches to Estimate Solubility and Permeability in Drug Discovery and Development Settings ,Adv. Drug Deliv. Rev., 46:3-26 (2001).
Lipkin et al., Biomarkers of increased susceptibility to gastreointestinal cancer: new application to studies of cancer prevention in human subjects, Cancer Research 48:235-245 (1988).
Liu et al., Fabrication and characterization of hydrogel-based microvalves, Mecoelectromech. Syst.11:45-53 (2002).
Liu et al., Passive Mixing in a Three-Dimensional Serpentine MicroChannel, J MEMS 9(2):190-197 (2000).
Lizardi et al., Mutation detection and single-molecule counting using isothermal rolling-circle amplification. Nat Genet 19(3):225-32 (1998).
Loakes and Brown, 5-Nitroindole as a universal base analogue. Nucleic Acids Res 22: 4039-4043 (1994).
Loakes et al., Stability and structure of DNA oligonucleotides containing non-specific base analogues. J. Mol. Biol 270:426-435 (1997).
Loeker et al., Colloids and Surfaces A: Physicochem. Eng. Aspects 214: 143-150, 2003).
Lopez-Herrera, et al, Coaxial jets generated from electrified Taylor cones. Scaling laws., Aerosol Science, 34 :535-552 (2003).
Lopez-Herrera, et al, One-Dimensional Simulation of the Breakup of Capillary Jets of Conducting Liquids Application to E.H.D. Spraying, Aerosol. Set, 30 (7): 895-912 (1999).
Lopez-Herrera, et al, {The electrospraying of viscous and non-viscous semi-insulating liquids. Scalilng laws,{ Bulletin of the American Physical Society, vol. 40, No. 12, pp. 2041 (1995).
Lorenceau et al, Generation of Polymerosomes from Double-Emulsions, Langmuir, 21(20): 9183-9186 (2005).
Lorenz et al, Isolation and expression of a cDNA encoding Renilla reniformis luciferase, PNAS 88(10):4438-42 (1991).
Loscertales, et al, Micro/Nano Encapsulation via Electrified Coaxial Liquid Jets, Science, 295(5560): 1695-1698 (2002).
Low N.M. et al., Mimicking somatic hypermutaion: affinity maturation of antibodies displayed on bacteriophage using a bacterila mutator strain. J Mol Biol 260(3), 359-68 (1996).
Lowe, K.C., Perfluorochemical respiratory gas carriers: benefits to cell culture systems, J Fluorine Chem 118:19-26 (2002).
Lowman et al., Selecting high affinity binding proteins by monovalent phage display, Biochemistry 30(45):10832-8 (1991).
Lu et al., Robust fluorescein-doped silica nanoparticles via dense-liquid treatment, Colloids and Surfaces A Physicachemical and Engineering Aspects, 303(3):207-210 (2007).
Luisi et al, Activity and Conformation of Enzymes in Reverse Micellar Solutions, Meth. Enzymol 136:188-216 (1987).
Lund et al., Assesment of methods for covalent binding of nucleic acids to magnetic beads, Dynabeads, and the characteristics of the bound nucleic acids in hybridization reactions, Nucleic Acids Research, Oxford University Press, 16(22) (1998).

(56) References Cited

OTHER PUBLICATIONS

Lunderberg et al., Solid-phase technology: magnetic beads to improve nucleic acid detection and analysis, Biotechnology Annual Review, 1:373-401 (1995).
Lundstrom, et al, Breakthrough in cancer therapy: Encapsulation of drugs and viruses, www.currentdrugdiscovery.com, Nov. 19-23, 2002.
Lyne, P.D., Structure-Based Virtual Screening: An Overview, Drug Discov. Today, 7(20):1047-1055 (2002).
Ma, C. et al., In vitro protein engineering using synthetic tRNA(Ala) with different anticodons, Biochemistry 32(31):7939-45 (1993).
Mackenzie et al., The application of flow microfluorimetry to biomedical research and diagnosis: a review, Dev Biol Stand 64:181-193 (1986).
Mackenzie, IABS Symposium on Reduction of Animal Usage in the Development and Control of Biological Products, London, UK, 1985.
Maclean, D. et al., Glossary of terms used in combinatorial chemistry, Pure Appl. Chem. 71(12):2349-2365 (1999).
Magdassi et al., Multiple Emulsions: HLB Shift Caused by Emulsifier Migration to External Interface, J. Colloid Interface Sci 97:374-379 (1984).
Mahajan et al., Bcl-2 and Bax Interactions in Mitochondria Probed with Green Florescent Protein and Fluorescence Resonance Energy Transfer, Nat. Biotechnol. 16(6): 547-552 (1998).
Manley et al., In vitro transcription: whole cell extract, Methods Enzymol, 101:568-82 (1983).
Manz et al., Micromachining of monocrystalline silicon and glass for chemical analysis systems A look into next century's technology or just a fashionable craze, Trends in Analytical Chemistry 10(5):144-149 (1991).
Mao et al., Kinetic behaviour of alpha-chymotrypsin in reverse micelles: a stopped-flow study, Eur J Biochem 208(1):165-70 (1992).
Mao, Q. et al., Substrate effects on the enzymatic activity of alphachymotrypsin in reverse micelles, Biochem Biophys Res Commun, 178(3):1105-12 (1991).
Mardis, E.R., The impact of next-generation sequencing technology on genetics, Trends Genet 24:133-141 (2008).
Margulies, M et al., Genome sequencing in microfabricated high-density picolitre reactors, Nature 437(7057):376-380 (2005).
Marques et al., Porous Flow within Concentric Cylinders, Bull Am Phys Soc Div Fluid Dyn 41:1768 (1996).
Mason, T.J. and Bibette, J. Shear Rupturing of Droplets in Complex Fluids, Langmuir, 13(17):4600-4613 (1997).
Mastrobattista et al., High-throughput screening of enzyme libraries: in vitro evolution of a beta-galactosidase by fluorescence-activated sorting of double emulsions, Chem. Biol. 12(12): 1291-1300 (2005).
Masui et ai., Probing of DNA-Binding Sites of *Escherichia coli* RecA Protein Utilizing 1-anilinonaphthalene-8-Sulfonic Acid, Biochem 37(35):12133-12143 (1998).
Matayoshi, E.D. et al., Novel fluorogenic substrates for assaying retroviral proteases by resonance energy transfer, Science 247:954 (1990).
Mattheakis et al., An in vitro polysome display system for identifying ligands from very large peptide libraries, PNAS 91:9022-6 (1994).
Mayr, L.M., and Fuerst, P., The Future of High-Throughput Screening, JBiomol Screen 13:443-448 (2008).
Mazutis et al., Droplet-Based Microfluidic Systems for High-Throughput Single DNA Molecule Isothermal Amplification and Analysis, Anal Chem 81(12):4813-4821 (2009).
Mazutis et al., Multi-step microfluidic droplet processing: kinetic analysis of an in vitro translated enzyme, Lab Chip 9:2902-2908 (2009).
McCafferty et al., Phage antibodies: filamentous phage displaying antibody variable domains,Nature, 348: 552-4 (1990).
McDonald and Whitesides, Poly(dimethylsiloxane) as a material for fabricating microfluidic devices, Account Chem. Res. 35:491-499 (2002).
McDonald et al. Fabrication of microfluidic systems in poly(dimethylsiloxane), Electrophoresis 21(1):27-40 (2000).
Melton et al., Efficient in vitro synthesis of biologically active RNA and RNA hybridization probes from plasmids containing a bacteriophage SP6 promoter, Nucl. Acids Res. 12(18):7035-7056 (1984).
Mendel, D. et al., Site-Directed Mutagenesis with an Expanded Genetic Code, Annu Rev Biophys Biomol Struct, 24:435-62 (1995).
Menger and Yamada, Enzyme catalysis in water pools, J. Am. Chem. Soc., 101:6731-4 (1979).
Meylan and Howard, Atom/fragment contribution method for estimating octanol-water partition coefficients, J Pharm Sci. 84(1):83-92 (1995).
Miele et al., Autocatalytic replication of a recombinant RNA, J Mol Biol, 171:281-95 (1983).
Minshuil, J. and Stemmer, W.P., Protein evolution by molecular breeding, Curr Opin Chem Biol 3(3): 284-90 (1999).
Miroux and Walker, Over-production of proteins in *Escherichia coli*: mutant hosts that allow synthesis of some membrane proteins and globular proteins at high levels, J of Mol Biol 260(3):289-98 (1996).
Miyawaki et at., Fluorescent Indicators for Ca2+ Based on Green Fluorescent Proteins and Calmodulin, Nature, 388: 882-887 (1997).
Mize et al., Dual-enzyme cascade—an amplified method for the detection of alkaline phosphatase, Anal Biochem 179(2): 229-35 (1989).
Mock et al., A fluorometric assay for the biotin-avidin interaction based on displacement of the fluorescent probe 2-anilinonaphthalene-6-sulfonic acid, Anal Biochem, 151:178-81 (1985).
Moldavan, A., Photo-electric technique for the counting of microscopical cells, Science 80:188-189 (1934).
Montigiani, S. et al., Alanine substitutions in calmodulin-binding peptides result in unexpected affinity enhancement, J Mol Biol, 258:6-13 (1996).
Moore, M.J., Exploration by lamp light, Nature, 374:766-7 (1995).
Moudrianakis and Beer, Base sequence determination in nucelic acids with the electron microscope 3. Chemistry and microscopy of guanine-labeled DNA, PNAS 53:564-71 (1965).
Mueth et al., Origin of stratification in creaming emulsions, Physical Review Letters 77(3):578-581 (1996).
Mulbry, W.W. et al., Parathion hydrolase specified by the Flavobacterium opd gene: relationshio between the gene and protein. J Bacteriol, 171: 6740-6746 (1989).
Mulder et al., Characterization of two human monoclonal antibodies reactive with HLA-B12 and HLA-B60, respectively, raised by in vitro secondary immunization of peripheral blood lymphocytes, Hum. Immunol 36(3):186-192 (1993).
Nakano et al., High speed polymerase chain reaction in constant flow, Biosci Biotech and Biochem, 58:349-52 (1994).
Nakano et al., Single-molecule PCR using water-in-oil emulsion, J Biotech, 102:117-24 (2003).
Nakano et al., Single-molecule reverse transcription polymerase chain reaction using water-in-oil emulsion, J Biosci Bioeng 99:293-295 (2005).
Nametkin, S.N. et al., Cell-free translation in reversed micelles, FEB Letters, 309(3):330-32.
Narang et al, Improved phosphotriester method for the synthesis of gene fragments, Methods Enzymol, 68:90-98 (1979).
Nelson, P. S., et al., Bifunctional oligonucleotide probes synthesized using a novel CPG support are able to detect single base pair mutations, Nucl Acids Res 17(18): 7187-7194 (1989).
Nemoto et al., In vitro virus: bonding of mRNA bearing puromycin at the 3 terminal end to the C-terminal end of its encoded protein on the ribosome in vitro, Federation of European Biochemical Societies, 414:405-8 (1997).
Ness, J.E. et al., Molecular Breeding: the natural approach to protein design. Adv Protein Chem, 55: 261-292 (2000).
Ng et al., Protein crystallization by capillary counter-diffusion for applied crystallographic structure determination, J. Struct. Biol. 2003, v142, pp. 218-231.

(56) References Cited

OTHER PUBLICATIONS

Ng, B.L. et al., Factors affecting flow karyotype resolution, Cytometry, Part A 69A: 1028-1036 (2006).
Nguyen et al., Optical detection for droplet size control in microfluidic droplet-based analysis systems, Sensors and Actuators B 117(2):431-436 (2006).
Nihant et al., Polylactide Microparticles Prepared by Double Emulsion/ Evaporation Technique. I. Effect of Primary Emulsion Stability, Pharmaceutical Research, 11(10):1479-1484 (1994).
Nisisako et al., Controlled formulation of monodisperse double emulsions in a multiple-phase microluidic system, Sot Matter, 1:23-27 (2005).
Nisisako et al., Formation of droplets using branch channels in a microfluidic circuit, Proceedings of the SICE Annual Conference. International Session Papers 1262-1264 (2002).
Nisisako et al., Microstructured Devices for Preparing Controlled Multiple Emulsions. Chem. Eng. Technol 31(8):1091-1098 (2008).
Nisisako, Takasi et al., Droplet Formation in a MicroChannel NetWO rk, Lab on a Chip, vol. 2, 2002, pp. 24-26.
Nissim, A. et al., Antibody fragments from a single pot phage display library as immunochemical reagents, Embo J, 13:692-8 (1994).
Nof and Shea, Drug-releasing scaffolds fabricated from drug-loaded microspheres, J. Biomed Mater Res 59:349-356 (2002).
Norman, A., Flow Cytometry, Med. Phys., 7(6):609-615 (1980).
Oberholzer et al., Enzymatic RNA replication in self-reproducing vesicles: an approach to a minimal cell, Biochem Biophys Res Commun 207(1):250-7 (1995).
Oberholzer et al., Polymerase chain reaction in liposomes, Chem. Biol. 2(10):677-82 (1995).
Obukowicz, M.G. et al., Secretion and export of IGF-1 in *Escerichia coli* strain JM101, Mol Gen Genet, 215:19-25 (1988).
Office Action for U.S. Appl. No. 11/246,911 dated Feb. 8, 2011.
Office Action for U.S. Appl. No. 11/360,845 dated Apr. 26, 2011.
Office Action for U.S. Appl. No. 11/360,845 dated Aug. 4, 2010.
Office Action for U.S. Appl. No. 11/698,298, dated Jun. 29, 2011.
Ogura, Y., Catalase activity at high concentrations of hydrogen peroxide, Archs Biochem Biophys, 57: 288-300 (1955).
Oh et al., Distribution of Macropores in Silica Particles Prepared by Using Multiple Emulsions, Journal of Colloid and Interface Science, 254(1): 79-86 (2002).
Okushima et al. Controlled production of monodisperse double emulsions by two-step droplet breakup in microfluidic devices, Langmuir 20(23): 9905-8 (2004).
Olsen et ai., Function-based isolation of novel enzymes from a large library, Nat Bioteoltnol 13(10):1071-4 (2000).
Omburo, G.A. et al., Characterization of the zinc binding site of bacterial phosphotriesterase, J of Biological Chem, 267:13278-83 (1992).
Oroskar et al., Detection of immobilized amplicons by ELISA-like techniques, Clin. Chem. 42:1547-1555 (1996).
Ostermeier, M. et al., A combinatorial approach to hybrid enzymes independent of DNA homology, Nat Biotechnol, 17(12):1205-9 (1999).
Ouelette, A new wave of microfluidic devices, Indust Physicist pp. 14-17 (2003).
Pabit et al., Laminar-Flow Fluid Mixer for Fast Fluorescence Kinetics Studies, Biophys J 83:2872-2878 (2002).
Paddison et al., Stable suppression of gene expression by RNAi in mammalian cells, PNAS 99(3):1443-1448 (2002).
Pannacci et al., Equilibrium and Nonequilibrium States in Microluidic Double Emulsions Physical Review Leters, 101(16):164502 (2008).
Park et al., Cylindrical compact thermal-cycling device for continuoflow polymeras chain reaction, Anal Chem, ACS, 75:6029-33 (2003).
Park et al., Model of Formation of Monodispersed Colloids, J. Phys. Chem. B 105:11630-11635 (2001).
Parker et al., Development of high throughput screening assays using fluorescence polarization: nuclear receptor-ligand-binding and kinase/phosphatase assays, J Biomol Screen, 5(2): 77-88 (2000).

Parmley et al., Antibody-selectable filamentous fd phage vectors: affinity purification of target genes. Gene 73(2):305-18 (1988).
Pedersen et al., A method for directed evolution and functional cloning of enzymes, PNAS 95(18):10523-8 (1998).
Pelham and Jackson, An efficient mRNA-dependent translation system from reticulocyte lysates, Eur J Biochem 67:247-56 (1976).
Pelletier et al., An in vivo library-verslibrary selection of optimized protein-protein interactions, Nature Biotechnology, 17:683-90 (1999).
Peng et al., Controlled Production of Emulsions Using a Crossflow Membrane, Particle & Particle Systems Characterization 15:21-25 (1998).
Perelson et al., Theoretical studies of clonal selection: minimal antibody repertoire size and relaibility of self-non-self discrimination. J Theor Biol 81(4):645-70 (1979).
Perez-Gilabert et al., Application of active-phase plot to the kinetic analysis of lipoxygenase in reverse micelles, Biochemistry J. 288:1011-1015 (1992).
Perrin, J., Polarisation de la lumiere de fluorescence vie moyenne des molecules dans letat excite, J. Phys. Rad. 1:390-401 (1926).
Petrounia, I.P. et al., Designed evolution of enzymatic properties, Curr Opin Biotechnol, 11:325-330 (2000).
Piemi et al., Transdermal delivery of glucose through hairless rat skin in vitro: effect of multiple and simple emulsions, Int J Pharm, 171:207-215 (1998).
Pirrung et al., A General Method for the Spatially Defined Immobilization of Biomolecules on Glass Surfaces Using 'Caged' Biotin, Bioconjug Chem 7: 317-321 (1996).
Ploem, in Fluorescent and Luminescent Probes for Biological Activity Mason, T. G. Ed., Academic Press, Landon, pp. 1-11, 1993.
Pluckthun, A. et al., In vitro selection and evolution of proteins, Adv Protein Chem, 55: 367-403 (2000).
Pollack et al., Electrowetting-based actuation of droplets for integrated microfluidics, Lab Chip 2:96-101 (2002).
Pollack et al., Selective chemical catalysis by an antibody, Science 234(4783):1570-3 (1986).
Pons et al, Synthesis of Near-Infrared-Emitting, Water-Soluble CdTeSe/CdZnS Core/Shell Quantum Dots, Chemistry of Materials 21(8):1418-1424 (2009).
Posner et al., Engineering specificity for folate into dihydrofolate reductase from *Escherichia coli*, Biochemistry, 35: 1653-63 (1996).
Poulin and Theil, "A priori" prediction of tissue: plasma partition coefficients of drugs to facilitate the use of physiologically-based pharmokinetic models in drug discovery, J Pharm Sci 89(1):16-35 (2000).
Priest, et al. Generation of Monodisperse Gel Emulsions in a Microfluidic Device, Applied Physics Letters, 88:024106 (2006).
Qi et al., Acid Beta-Glucosidase: Intrinsic Fluorescence and Conformational Changes Induced by Phospholipids and Saposin C, Biochem., 37(33): 11544-11554 (1998).
Raghuraman et al., Emulston Liquid Membranes for Wastewater Treatment: Equillibrium Models for Some Typical Metal-Extractant Systems,Environ. Sci. Technol 28:1090-1098 (1994).
Ralhan, Discovery and Verification of Head-and-neck Cancer Biomarkers by Differential Protein Expression Analysis Using iTRAQ Labeling, Multidimensional Liquid Chromatography, and Tandem Mass Spectrometry, Mol Cell Proteomics 7(6):1162-1173 (2008).
Ramsey, J.M., The burgeoning power of the shrinking laboratory, Nat Biotechnol 17(11):1061-2 (1999).
Ramstrom and Lehn, Drug discovery by dynamic combinatorial libraries, Nat Rev Drug Discov 1:26-36 (2002).
Raushel, F.M. et al., Phosphotriesterase: an enzyme in search of its natural substrate, Adv Enzymol Relat Areas Mol Biol, 74: 51-93 (2000).
Rech et al., Introduction of a yeast artificial chromosome vector into *Sarrachomyeces cervesia* by electroporation, Nucleic Acids Res 18:1313 (1990).
Reyes et al., Micro Total Analysis Systems. 1. Introduction, Theory and Technology, Anal Chem 74(12):2623-2636 (2002).
Riess, J.S., Fluorous micro- and nanophases with a biomedical perspective, Tetrahedron 58(20):4113-4131 (2002).
Roach et al., Controlling nonspecific protein adsorption in a plug-based microfluidic system by controlling inteifacial chemistry using fluorophase surfactants, Anal. Chem. 77:785-796 (2005).

(56) References Cited

OTHER PUBLICATIONS

Roberts & Ja, In vitro selection of nucleic acids and proteins: What are we learning, Curr Opin Struct Biol 9(4): 521-9 (1999).
Roberts et al., Simian virus 40 DNA directs synthesis of authentic viral polypeptides in a linked transcription-translation cell-free system 72(5):1922-1926 (1975).
Roberts, et al., RNA-peptide fusion for the in vitro selection of peptides and proteins, PNAS 94:12297-302 (1997).
Roberts, J.W.,Termination factor for RNA synthesis, Nature, 224: 1168-74 (1969).
Roberts, R.W. Totally in vitro protein selection using mRNA-protein fusions and ribosome display. Curr Opin Chem Biol 3(3), 268-73 (1999).
Rodriguez-Antona et al., Quantitative RT-PCR measurement of human cytochrome P-450s: application to drug induction studies. Arch. Biochem. Biophys., 376:109-116 (2000).
Rolland et al., Fluorescence Polarization Assay by Flow Cytometry, J. Immunol. Meth., 76(1): 1-10 (1985).
Rosenberg et al.,Termination of transcription in bacteriophage lambda, J Biol Chem, 250: 4755-64 (1975).
Rosenberry, T.L., Acetylcholinesterase, Adv Enzymol Relat Areas Mol Biol, 43: 103-218 (1975).
Rotman, Measurement of activities of single molecules of beta-galactosidase, PNAS, 47:1981-91 (1961).
Russon et al., Single-nucleotide polymorphism analysis by allele-specific extension of fluorescently labeled nucleotides in a microfluidic flow-through device, Electrophoresis, 24:158-61 (2003).
Sadtler et al., Achieving stable, reverse water-in-fluorocarbon emulsions. Angew Chem Int Ed 35:1976-1978 (1996).
Saiki, R.K, et al, Primer directed enzymatic amplification of DNA with a thermostable DNA polymerase. Science 239(4839):487-91 (1988).
Sakamoto, Rapid and simple quantification of bacterial cells by using a microfluidic device, Appl Env Microb. 71:2 (2005).
Sanchez et al., Breakup of Charged Capillary Jets, Bulletin of the American Physical Society Division of Fluid Dynamics 41:1768-1768 (1996).
Sano, T. et al., Immuno-PCR-Very sensitive antigen-detection by means of sepcific antibody-DNA conjugates. Science 258(5079), 120-122 (1992).
SantaLucia, A unified view of polymer, dumbbell, and oligonucleotide DNA nearest-neighbor thermodynamics, PNAS 95(4):1460-5 (1998).
Santra et al., Fluorescence lifetime measurements to determine the core-shell nanostructure of FITC-doped silica nanoparticles: An optical approach to evaluate nanoparticle photostability, J Luminescence 117(1):75-82 (2006).
Schatz et al., Screening of peptide libraries linked to lac repressor, Methods Enzymol 267: 171-91 (1996).
Schneegass et al., Miniaturized flow-through PCR with different template types in a silicone chip thermocycler, Lab on a Chip, Royal Soc of Chem, 1:42-9 (2001).
Schubert et al., Designer Capsules, Nat Med 8:1362 (2002).
Schweitzer et al., Immunoassays with rolling circle DNA amplification: A versatile platform for ultrasensitive antigen detection, PNAS 97(18), 10113-10119 (2000).
Schweitzer, B. et al., Combining nucleic acid amplification and detection. Curr Opin Biotechnol 12(1):21-7 (2001).
Scott, R.L., The Solubility of Fluorocarbons, J. Am. Chem. Soc, 70: 4090-4093 (1948).
Seethala and Menzel, Homogeneous, Fluorescence Polarization Assay for Src-Family Tyrosine Kinases, Anal Biochem 253(2):210-218 (1997).
Seiler et al., Planar glass chips for capillary electrophoresis: repetitive sample injection, quantitation, and separation efficiency, Anal Chem 65(10):1481-1488 (1993).
Selwyn M. J., A simple test for inactivation of an enzyme during assay, Biochim Biophys Acta 105:193-195 (1965).
Seo et al., Microfluidic consecutive flow-focusing droplet generators, Soft Matter, 3:986-992 (2007).

Seong and Crooks, Efficient Mixing and Reactions Within Microfluidic Channels Using Microbead-Supported Catalysts, J Am Chem Soc 124(45):13360-1 (2002).
Seong et al., Fabrication of Microchambers Defined by Photopolymerized Hydrogels and Weirs Within Microfluidic Systems: Application to DNA Hybridization, Analytical Chem 74(14):3372-3377 (2002).
Sepp et al., Microbead display by in vitro compartmentalisation: selection for binding using flow cytometry, FEBS Letters 532:455-58 (2002).
Serpersu et al., Reversible and irreversible modification of erythrocyte membranse permeability by electric field, Biochim Biophys Acta 812(3):779-785 (1985).
Shapiro, H.M., Multistation multiparameter flow cytometry: a critical review and rationale, Cytometry 3: 227-243 (1983).
Shestopalov et al., Multi-Step Synthesis of Nanoparticles Performed on Millisecond Time Scale in a Microfluidic Droplet-Based System, The Royal Society of Chemistry 4:316-321, 2004.
Shtern V, and Hussain F., Hysteresis in swirling jets, J. Fluid Mech. 309:1-44 (1996).
Sia &Whitesides, Microfluidic devices fabricated in poly(dimethylsiloxane) for biological studies, Electrophoresis 24(21):3563-3576 (2003).
Sidhu, S.S., Phage display in pharmaceutical biotechnology, Curr Opin Biotech 11:610-616 (2000).
Siemering et al., Mutations that suppress the thermosensitivity of green fluorescent protein, Current Biology 6:1653-1663 (1996).
Silva-Cunha et al., W/O/W multiple emulsions of insulin containing a protease inhibitor and an absorption enhancer: biological activity after oral administration to normal and diabetic rats, Int J Pharm 169:33-44 (1998).
Sims et al., Immunopolymerase chain reaction using real-time polymerase chain reaction for detection, Anal. Biochem. 281(2):230-2 (2000).
Slappendel et al., Normal cations and abnormal membrane lipids in the red blood cells of dogs with familial stomatocytosis hypertrophic gastritis, Blood 84:904-909 (1994).
Slob et al., Structural identifiability of PBPK models: practical consequences for modeling strategies and study designs, Crit Rev Toxicol. 27(3):261-72 (1997).
Smith et al., Direct mechanical measurements of the elasticity of single DNA molecules by using magnetic beads, Science 258(5085):1122-1126 (1992).
Smith et al., Fluorescence detection in automated DNA sequence analysis, Nature 321 :674-679 (1986).
Smith et al., Phage display, Chemical Reviews 97(2), 391-410 (1997).
Smith et al., The synthesis of oligonucleotides containing an aliphatic amino group at the 5' terminus: synthesis of fluorescent DNA primers for use in DNA sequence analysis, Nucl. Acid Res. 13:2399-2412 (1985).
Smith G.P., Filamentous fusion phage: novel expression vectors that display cloned antigens on the virion surface, Science 228(4705): 1315-7(1985).
Smyth et al., Markers of apoptosis: methods for elucidating the mechanism of apoptotic cell death from the nervous system, Biotechniques 32:648-665 (2000).
Sohn, et al, Capacitance cytometry: Measuring biological cells one by one, PNAS 97(20):10687-10690 (2000).
Somasundaram and Ramalingam, Gain studies of Rhodamine 6G dye doped polymer laser, J Photochem Photobiol 125(1-3):93-98 (1999).
Song et al., A microfluidic system for controlling reaction networks in time, Angew. Chem. Int. Ed. 42(7):768-772 (2003).
Song et al., Experimental Test of Scaling of Mixing by Chaotic Advection in Droplets Moving Through Microfluidic Channels, App Phy Lett 83(22):4664-4666 (2003).
Song, H. and Ismagilov, R.F., Millisecond kinetics on a microluidic chip using nanoliters of reagents, J Am Chem Soc. 125: 14613-14619 (2003).
Soni and Meller, Progress toward ultrafast DNA sequencing using solid-state nanopores, Clin Chem 53:1996-2001 (2007).
Soumillion et al., Novel concepts for the selection of catalytic activity. Curr Opin Biotechnol 12:387-394 (2001).

(56) References Cited

OTHER PUBLICATIONS

Soumillion et al., Selection of B-lactomase on filamentous bacteriophage by catalytic activity, J Mol Biol, 237:415-22 (1994).
Sproat et al., The synthesis of protected 5'-mercapto-2',5'-dideoxyribonucleoside-3'-0-phosphorainidites, uses of 5'-mercapto-oligodeoxyribonucleotides, Nucleic Acids Res 15:4837-4848 (1987).
Stauber, et a., Rapid generation of monoclonal antibody-secreting hybridomas against African horse sickness virus by in vitro immunization and the fusion/cloning technique, J. Immunol. Meth 161(2):157-168 (1993).
Stemmer, W.P., DNA shuffling by random fragmentation and reassembly: in vitro recombination for molecular evolution. PNAS 91(22):10747-51(1994).
Stemmer, W.P., Rapid evolution of a protein in vitro by DNA shuffling, Nature 370(6488):389-91 (1994).
Stober et al., Controlled growth of monodisperse silica spheres in the micron size range, J Colloid and Interface Sci 26(1):62-69 (1968).
Stofko, H.R. et al., A single step purification for recombinant proteins. Characterization of microtube associated protein (MAP2) fragment which associates with the type II cAMP-dependent protein kinase, Febs Lett 302: 274-278 (1992).
Stone et al., Engineering flows in small devices: Microfluidics toward a lab-on-a-chip, Ann. Rev. Fluid Mech. 36:381-441 (2004).
Strizhkov et al., PCR amplification on a microarray of gel-immobilized oligonucleotides: Detection of bacterial toxin- and drug-resistant genes and their mutations, BioTechniques 29(4):844-857 (2000).
Stroock et al., Chaotic mixer for microchannels, Science 295(5555):647-651 (2002).
Studer et al., Fluorous Synthesis: A FluoroPhase Strategy for Improving Separation Efficiency in Organic Synthesis, Science 275: 823-826 (1997).
Sugiura et al., Effect of Channel Structure on MicroChannel Emuisification, Langmuir 18:5708-5712 (2002).
Sugiura et al., Interfacial tension driven monodispersed droplet formation from mtcrofabricated channel array Langmuir, 17: 5562-5566 (2001).
Sundberg et al., Spatially-Addressable Immobilisation of Macromolecules on Solid Supports, J. Am. Chem. Soc, 117:12050-12057 (1995).
Sung et al. Chip-based microfluidic devices coupled with electrospray ionization-mass spectrometry, Electrophoresis 26:1783-1791 (2005).
Suzuki et al., Random mutagenesis of thermus aquaticus DNA polmerase I: concordance of immutable sites in vivo with the crystal structure, PNAS USA, 93:96701-9675 (1996).
Tabatabai and Faghri, A New Two-Phase Flow Map and Transition Boundary Accounting for Surface Tension Effects in Horizontal Miniature and Micro Tubes, J Heat Transfer 123:958-968 (2001).
Tabatabai et al, Economic feasability study of polyelectrolyte-enhanced ultrafiltration (PEUF) for water softening, J Membrane Science 100(3):193-207 (1995).
Tabatabai et al., Reducing Surfactant Adsorption on Carbonate Reservoirs, SPE Resenroir Engineering 8(2):117-122 (1993).
Tabatabai, Water Softening Using polyelectrolyte-enhanced ultrafiltration, Separation Science Technology 30(2):211-224 (1995).
Takayama et al., Patterning Cells and Their Environments Using Multiple Laminar Fluid Flows in Capillary NetWO rks, PNAS 96:5545-5548 (1999).
Takeuchi et al., An Axisymmetric Flow-Focusing Microfluidic Device, Adv. Mater 17(8):1067-1072 (2005).
Taly et al., Droplets as Microreactors for High-Throughput Biology, Chembiochem 8(3):263-272 (2007).
Tan et al., Controlled Fission of Droplet Emulsions in Bifurcating Microfluidic Channels, Transducers Boston (2003).
Tan et al., Design of microluidic channel geometries for the control of droplet volume, chemical concentration, and sorting, Lab Chip, 4(4): 292-298 (2004).
Tan et al., Monodispersed microfluidic droplet generation by shear focusing microfluidic device, Sensors and Actuators 114:350-356 (2006).
Tan, Y.C., Microfluidic Liposome Generation from Monodisperse Droplet Emulsion—Towards the Realization of Artificial Cells, Summer Bioengineering Conference, Florida (2003).
Tan, Y.C., Monodisperse Droplet Emulsions in Co-Flow Microfluidic Channels, Micro TAS, Lake Tahoe (2003).
Tanaka et al., Ethanol Production from Starch by a Coimmobilized Mixed Culture System of Aspergillus awamori and Zymomonas mobilis, Biotechnol Bioeng XXVII:1761-1768 (1986).
Tang et al., A multi-color fast-switching microfluidic droplet dye laser, Lab Chip 9:2767-2771 (2009).
Taniguchi et al., Chemical Reactions in Microdroplets by Electrostatic Manipulation of Droplets in Liquid Media, Lab on a Chip 2:19-23 (2002).
Tawfik et al., catELISA: a facile general route to catalytic antibodies, PNAS 90(2):373-7 (1993).
Tawfik et al., Efficient and selective p-nitrophenyl-ester= hydrolyzing antibodies elicited by a p-nitrobenzyl phosphonate hapten, Eur J Biochem, 244:619-26 (1997).
Tawfik et al., Man-made cell-like compartments for molecular evolution, Nature Biotechnology, 7(16):652-56 (1998).
Tawfik, D.S. et al., 1,8-diabycyclo[5.4.0]undecane mediated transesterification of p-nitrophenyl phosphonates—a novel route to phosphono esters, Synthesis-Stuttgart, 10: 968-972 (1993).
Taylor et al., Characterization of chemisorbed monolayers by surface potential measurments, J. Phys. D. Appl. Phys. 24:1443 (1991).
Taylor, The formation of emulsions in definable field of flow, Proc R Soc London A 146(858):501-523 (1934).
Tchagang et al., Early detection of ovarian cancer using group biomarkers, Mol Cancer Ther 7:27-37 (2008).
Tencza et al., Development of a Fluorescence Polarization-Based Diagnostic Assay for Equine Infectious Anemia Virus, J Clinical Microbiol 38(5):1854-185 (2000).
Terray et al., Microfluidic Control Using Colloidal Devices,Science, 296(5574):1841-1844 (2002).
Terray, et al, Fabrication of linear colloidal structures for microfluidic applications, Applied Phys Lett 81(9):1555-1557 (2002).
Tewhey et al., Microdroplet-based PCR amplification for large scale targeted sequencing, Nat Biotechnol 27(11):1025-1031 (2009).
Theberge et al., Microdroplets in Microfluidics: An Evolving Platform for Discoveries in Chemistry and Biology, Angew. Chem. Int. Ed 49(34):5846-5868 (2010).
Thompson, L.F., Introduction to Lithography, ACS Symposium Series 219:1-13, (1983).
Thorsen et al., Dynamic pattern formation in a vesicle-generating microfluidic device, Phys Rev Lett 86(18):4163-4166 (2001).
Thorsen et al., Microfluidic Large-Scale Integration, Science 298:580-584 (2002).
Tice et al., Effects of viscosity on droplet formation and mixing in microfluidic channels, Analytica Chimica Acta 507:73-77 (2004).
Tice et al., Formation of droplets and mixing in multiphase microfluidics at low values of the reynolds and the capillary numbers, Langmuir 19:9127-9133 (2003).
Titomanlio et al., Capillary experiments of flow induced crystallization of HOPE, AlChe Journal, 1990, v36, No. 1, pp. 13-18.
Tleugabulova et al., Evaluating formation and growth mechanisms of silica particles using fluorescence anisotropy decay analysis, Langmuir 20(14):5924-5932 (2004).
Tokatlidis et al., Nascent chains: folding and chaperone intraction during elongation on ribosomes, Philos Trans R Soc Lond B Biol Sci, 348:89-95 (1995).
Tokeshi et al., ContinuoFlow Chemical Processing on a Microchip by Combining Microunit Operations and a Multiphase Flow NetWO rk, Anal Chem 74(7):1565-1571 (2002).
Tokumitsu, H. et al., Preparation of gadopentetic acid-loaded chitosan microparticles for gadolinium neutron-capture therapy of cancer by a novel emulsion-droplet coalescence technique, Chem and Pharm Bull 47(6):838-842 (1999).
Tramontano, A., Catalytic antibodies, Science 234(4783):1566-70 (1986).

(56) References Cited

OTHER PUBLICATIONS

Trindade, T., Nanocrystalline semiconductors: synthesis, properties, and perspectives, Chem. Mat. 13:3843-3858 (2001).

Tripet, B. et al., Engineering a de novo-designed coiled-coil heterodimerization domain off the rapid detection, purification and characterization of recombinantly expressed peptides and proteins, Protein Engng., 9:1029-42 (1996).

Tuerk, C. and Gold, L., Systematic Evolution of Ligands by Exponentid Enrichment: RNA Ligands to Bacteriophage T4 DNA Polymerase, Science, 249:505-10 (1990).

Umbanhowar et al., Monodisperse Emulsion Generation via Drop Break Off in a Coflowing Stream, Langmuir 16(2):347-351 (2000).

Unger et al., Monolithic microfabricated valves and pumps by multylayer soft lithography, Science 288(5463):113-116 (2000).

Utada, A. et al., Monodisperse double emulsions generated from a microcapillary device, Science, 308:537-541 (2005).

Vainshtein et al., Peptide rescue of an N-terminal truncation of the stoffel fragment of Taq DNA polymerase, Protein Science, 5:1785-92 (1996).

Van Bockstaele et al., Prognostic markers in chronic lymphocytic leukemia: a comprehensive review, Blood Rev 23(1):25-47 (2009).

Van Dilla et al., Cell Microfluorometry: A Method for Rapid Fluorescence Measurement, Science 163(3872):1213-1214 (1969).

Van Dilla et al., The fluorescent cell photometer: a new method for the rapid measurement of biological cells stained with fluorescent dyes, Annual Report of the Los Alamos Scientific Laboratory of the University of California (Los Alamos, NM), Biological and Medical Research Groupp (H-4) of the Health Division, Compiled by D. G. Ott, pp. 100-105, distributed Jan. 23, 1968.

Vanhooke et al., Three-dimensional structure of the zinc-containing phosphotrieesterase with the bound substrate analog diethy 4-methylbenzylphosphonate, Biochemistry 35:6020-6025 (1996).

Varga, J.M. et al., Mechanism of allergic cross-reactions-I. Multispecific binding of ligands to a mouse monoclonal anti-DNP IgE antibody. Mol Immunol 28(6), 641-54 (1991).

Vary, A homogeneous nucleic acid hybridization assay based on strand displacement, Nucl Acids Res 15(17):6883-6897 (1987).

Venkateswaran et al., Production of Anti-Fibroblast Growth Factor Receptor Monoclonal Antibodies by In Vitro Immunization, Hybirdoma, 11(6):729-739 (1992).

Venter et al., The sequence of the human genome, Science 291(5507):1304-51 (2001).

Vogelstein et al., Digital PCR, PNAS 96(16):9236-9241 (1999).

Voss, E.W., Kinetic measurements of molecular interactions by spectrofluorometry, J Mol Recognit, 6:51-58 (1993).

Wahler, D. et al., Novel methods for biocatalyst screening. Curr Opin Chem Biol, 5: 152-158 (2001).

Walde, P. et al., Oparin's reactions revisited: enzymatic synthesis of poly(adenylic acid) in micelles and self-reproducing vesicles. J Am Chem Soc, 116: 7541-7547 (1994).

Walde, P. et al., Spectroscopic and kinetic studies of lipases solubilized in reverse micelles, Biochemistry, 32(15):4029-34 (1993).

Walde, P. et al., Structure and activity of trypsin in reverse micelles, Eur J Biochem, 173(2):401-9 (1988).

Walker et al., Isothermal in vitro amplification of DNA by a restriction enzyme/DNA polymerase system, PNAS 89(1):392-6 (1992).

Walker et al., Strand displacement amplification—an isothermal, in vitro DNA amplification technique, Nucleic Acid Res, 20(7):1691-6 (1992).

Wang et al., DEP actuated nanoliter droplet dispensing using feedback control, Lab on a Chip 9:901-909 (2008).

Wang et al., Preparation of Titania Particles Utilizing the Insoluble Phase Interface in a MicroChannel Reactor, Chemical Communications 14:1462-1463 (2002).

Wang, A.M. et al., Quantitation of mRNA by the polymerase chain reaction. Proc natl Acad Sci USA 86(24), 9717-21 (1989).

Wang, G.T. et al., Design and synthesis of new fluorogenic HIV protease substrates based on resonance energy transfer, Tetrahedron Lett., 31:6493 (1990).

Warburton, B., Microcapsules for Multiple Emulsions, Encapsulation and Controlled Release, Spec Publ R Soc Chem, 35-51 (1993).

Wasserman et al., Structure and reactivity of allyl-siloxane monolayers formed by reaction of allcyltrichlorosilanes on silicon substrates, Langmuir 5:1074-1087 (1989).

Weil. et al., Selective and accurate initiation of transcription at the Ad2 major late promotor in a soluble system dependent on purified RNA polymerase II and DNA, Cell, 18(2):469-84 (1979).

Werle et al., Convenient single-step, one tube purification of PCR products for direct sequencing, Nucl Acids Res 22(20):4354-4355 (1994).

Wetmur et al., Molecular haplotyping by linking emulsion PCR: analysis of paraoxonase 1 haplotypes and phenotypes, Nucleic Acids Res 33(8):2615-2619 (2005).

Wick et al., Enzyme-containing liposomes can endogenously produce membrane-constituting lipids, Chem Biol 3(4):277-85 (1996).

Widersten and Mannervik, Glutathione Transferases with Novel Active Sites Isolated by Phage Display from a Library of Random Mutants, J Mol Biol 250(2):115-22 (1995).

Wiggins et al., Foundations of chaotic mixing, Philos Transact A Math Phys Eng Sci 362(1818):937-70 (2004).

Williams et al., Amplification of complex gene libraries by emulsion PCR, Nature Methods 3(7):545-550 (2006).

Williams et al., Methotrexate, a high-affinity pseudosubstrate of dihydrofolate reductase, Biochemistry, 18(12):2567-73 (1979).

Wilson, D.S. and Szostak, J.W., In vitro selection of functional nucleic acids, Ann. Rev. Biochem. 68: 611-647 (1999).

Winter et al., Making antibodies by phage display technology, Annu Rev Immunol 12:433-55 (1994).

Wittrup, K.D., Protein engineering by cell-surface display. Curr Opin Biotechnology, 12: 395-399 (2001).

Wolff et al., Integrating advanced functionality in a microfabricated high-throughput fluorescent-activated cell sorter, Lab Chip, 3(1): 22-27 (2003).

Wronski et al., Two-color, fluorescence-based microplate assay for apoptosis detection. Biotechniques, 32:666-668 (2002).

Wu et al., The ligation amplification reaction (LAR)-amplification of specific DNA sequences using sequential rounds of template-dependent ligation, Genomics 4(4):560-9 (1989).

Wyatt et al., Synthesis and purification of large amounts of RNA oligonucleotides, Biotechniques 11(6):764-9 (1991).

Xia and Whitesides, Soft Lithography, Angew. Chem. Int. Ed. 37:550-575 (1998).

Xia and Whitesides, Soft Lithography, Ann. Rev. Mat. Sci. 28:153-184 (1998).

Xu, S. et al., Generation of monodisperse particles by using microfluidics: control over size, shape, and composition, Angew. Chem. Int. Ed. 44:724-728 (2005).

Yamagishi, J. et al., Mutational analysis of structure-activity relationships in human tumor necrosis factor-alpha, Protein Eng, 3:713-9 (1990).

Yamaguchi et al., Insulin-loaded biodegradable PLGA microcapsules: initial burst release controlled by hydrophilic additives, Journal of Controlled Release, 81(3): 235-249 (2002).

Yelamos, J. et al., Targeting of non-Ig sequences in place of the V segment by somatic hypermutation. Nature 376(6537):225-9 (1995).

Yershov et al., DNA analysis and diagnostics on oligonucleotide microchips, PNAS 93(10):4913-4918 (1996).

Yonezawa et al., DNA display for in vitro selection of diverse peptide libraries, Nucleic Acids Research, 31(19): e118 (2203).

Yu et al. Responsive biomimetic hydrogel valve for microfluidics. Appl. Phys. Lett 78:2589-2591 (2001).

Yu et al., Quantum dot and silica nanoparticle doped polymer optical fibers, Optics Express 15(16):9989-9994 (2007).

Yu et al., Specifc inhibition of PCR by non-extendable oligonucleotides using a 5{ to 3{ exonuclease-deficient DNA polymerase, Biotechniques 23(4):714-6, 718-20 (1997).

Zaccolo, M. et al., An approach to random mutagenesis of DNA using mixtures of triphosphate derivatives of nucleoside analogues. J Mol Biol 255(4):589-603 (1996).

Zakrzewski, S.F., Preparation of tritiated dihydrofolic acid of high specific activity, Methods Enzymol, 539 (1980).

(56) References Cited

OTHER PUBLICATIONS

Zaug and Cech, The intervening sequence RNA of Tetrahymena is an enzyme, Science 231(4737):470-5 (1986).
Zaug and Cech, The Tetrahymena intervening sequence ribonucleic acid enzyme is a phosphotransferase and an acid phosphatase, Biochemistry 25(16):4478-82 (1986).
Zaug et al., The Tetrahymena ribozyme acts like an RNA restriction endonuclease, Nature 324(6096):429-33 (1986).
Zhang et al., A Simple Statistical Parameter for Use in Evaluation and Validation of High Throughput Screening Assays, Journal of Biomolecular Screening, 4(2): 67-73 (1999).
Zhang, Z.Y., Substrate specificity of the protein tyrosine phosphatases, PNAS 90: 4446-4450 (1993).
Zhao, B. et al., Control and Applications of Immiscible Liquids in Microchannels, J. Am. Chem. Soc, vol. 124:5284-5285 (2002).
Zhao, H. et al., Molecular evolution by staggered extension process (StEP) in vitro recombination. Nat Biotechnol 16(3):258-61 (1998).
Zheng et al., A Droplet-Based, Composite PDMS/Glass Capillary Microfluidic System for Evaluating Protein Crystallization Conditions by Microbatch and Vapor-Diffusion Methods with On-Chip X-Ray Diffraction, Angew. Chem., pp. 1-4, 2004.
Zheng et al., A Microiuidic Approach for Screening Submicroliter Volumes against Multiple Reagents by Using Performed Arrays of Nanoliter Plugs in a Three-Phase Liquid/Liquid/Gas Flow, Angew. Chem. Int. Ed., 44(17): 2520-2523 (2005).
Zheng et al., Formation of Droplets of Alternating Composition in Microfluidic Channels and Applications to Indexing of Concentrations in Droplet-Based /Assays, Anal. Chem.,76: 4977-4982 (2004).
Zheng et al., Screening of Protein Crystallization Conditions on a Microfluidic Chip Using Nanoliter-Size Droplets, J Am Chem Soc 125(37):11170-11171 (2003).
Zimmermann et al., Dielectric Breakdown of Cell Membranes, Biophys J 14(11):881-889 (1974).
Zimmermann et al., Microscale Production of Hybridomas by Hypo-Osmolar Electrofusion, Hum. Antibod. Hybridomas, 3(1): 14-18 (1992).
Zubay, G., In vitro synthesis of protein in microbial systems, Annu Rev Genet, 7: 267-87 (1973).
Zubay, G., The isolation and properties of CAP, the catabolite gene activator, Methods Enzymol, 65: 856-77 (1980).
Zuckermann, R. et al., Efficient Methods for Attachment of Thiol-Specific Probes to the 3{-end of Synthetic Oligodeoxyribonucleotides, Nucleic Acids Res. 15:5305-5321 (1987).

* cited by examiner

| particles radius (nm) | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| particles volume (nm^3) | 4 | 34 | 113 | 268 | 524 | 905 | 1437 | 2145 | 3054 | 4189 | 5575 | 7238 | 9203 | 11494 | 14137 |
| Nb of dyes per particule | | | | | | | | estimated mean distance between dyes in nm | | | | | | | |
| 2 | 1,28 | 2,56 | 3,84 | 5,12 | 6,40 | 7,68 | 8,96 | 10,24 | 11,51 | 12,79 | 14,07 | 15,35 | 16,63 | 17,91 | 19,19 |
| 3 | 1,12 | 2,24 | 3,35 | 4,47 | 5,59 | 6,71 | 7,82 | 8,94 | 10,06 | 11,18 | 12,29 | 13,41 | 14,53 | 15,65 | 16,77 |
| 4 | 1,02 | 2,03 | 3,05 | 4,06 | 5,08 | 6,09 | 7,11 | 8,12 | 9,14 | 10,15 | 11,17 | 12,19 | 13,20 | 14,22 | 15,23 |
| 5 | 0,94 | 1,89 | 2,83 | 3,77 | 4,71 | 5,66 | 6,60 | 7,54 | 8,48 | 9,43 | 10,37 | 11,31 | 12,26 | 13,20 | 14,14 |
| 6 | 0,89 | 1,77 | 2,66 | 3,55 | 4,44 | 5,32 | 6,21 | 7,10 | 7,98 | 8,87 | 9,76 | 10,65 | 11,53 | 12,42 | 13,31 |
| 7 | 0,84 | 1,69 | 2,53 | 3,37 | 4,21 | 5,06 | 5,90 | 6,74 | 7,58 | 8,43 | 9,27 | 10,11 | 10,95 | 11,80 | 12,64 |
| 8 | 0,81 | 1,61 | 2,42 | 3,22 | 4,03 | 4,84 | 5,64 | 6,45 | 7,25 | 8,06 | 8,87 | 9,67 | 10,48 | 11,28 | 12,09 |
| 9 | 0,77 | 1,55 | 2,32 | 3,10 | 3,87 | 4,65 | 5,42 | 6,20 | 6,97 | 7,75 | 8,52 | 9,30 | 10,07 | 10,85 | 11,62 |
| 10 | 0,75 | 1,50 | 2,24 | 2,99 | 3,74 | 4,49 | 5,24 | 5,99 | 6,73 | 7,48 | 8,23 | 8,98 | 9,73 | 10,48 | 11,22 |
| 11 | 0,72 | 1,45 | 2,17 | 2,90 | 3,62 | 4,35 | 5,07 | 5,80 | 6,52 | 7,25 | 7,97 | 8,70 | 9,42 | 10,15 | 10,87 |
| 12 | 0,70 | 1,41 | 2,11 | 2,82 | 3,52 | 4,22 | 4,93 | 5,63 | 6,34 | 7,04 | 7,75 | 8,45 | 9,15 | 9,86 | 10,56 |
| 13 | 0,69 | 1,37 | 2,06 | 2,74 | 3,43 | 4,11 | 4,80 | 5,48 | 6,17 | 6,86 | 7,54 | 8,23 | 8,91 | 9,60 | 10,28 |
| 14 | 0,67 | 1,34 | 2,01 | 2,68 | 3,34 | 4,01 | 4,68 | 5,35 | 6,02 | 6,69 | 7,36 | 8,03 | 8,69 | 9,36 | 10,03 |
| 15 | 0,66 | 1,31 | 1,96 | 2,61 | 3,27 | 3,92 | 4,57 | 5,23 | 5,88 | 6,53 | 7,19 | 7,84 | 8,50 | 9,15 | 9,80 |
| 16 | 0,64 | 1,28 | 1,92 | 2,56 | 3,20 | 3,84 | 4,48 | 5,12 | 5,76 | 6,40 | 7,04 | 7,68 | 8,32 | 8,96 | 9,60 |
| 17 | 0,63 | 1,25 | 1,88 | 2,51 | 3,13 | 3,76 | 4,39 | 5,02 | 5,64 | 6,27 | 6,90 | 7,52 | 8,15 | 8,78 | 9,40 |
| 18 | 0,62 | 1,23 | 1,85 | 2,46 | 3,08 | 3,69 | 4,31 | 4,92 | 5,54 | 6,15 | 6,77 | 7,38 | 8,00 | 8,61 | 9,23 |
| 19 | 0,60 | 1,21 | 1,81 | 2,42 | 3,02 | 3,62 | 4,23 | 4,83 | 5,44 | 6,04 | 6,66 | 7,25 | 7,85 | 8,46 | 9,06 |
| 20 | 0,59 | 1,19 | 1,78 | 2,38 | 2,97 | 3,56 | 4,16 | 4,75 | 5,34 | 5,94 | 6,53 | 7,13 | 7,72 | 8,31 | 8,91 |
| 21 | 0,58 | 1,17 | 1,75 | 2,34 | 2,92 | 3,51 | 4,09 | 4,67 | 5,26 | 5,84 | 6,43 | 7,01 | 7,60 | 8,18 | 8,76 |
| 22 | 0,58 | 1,15 | 1,73 | 2,30 | 2,88 | 3,45 | 4,03 | 4,60 | 5,18 | 5,75 | 6,33 | 6,90 | 7,48 | 8,05 | 8,63 |
| 23 | 0,57 | 1,13 | 1,70 | 2,27 | 2,83 | 3,40 | 3,97 | 4,53 | 5,10 | 5,67 | 6,24 | 6,80 | 7,37 | 7,94 | 8,50 |
| 24 | 0,56 | 1,12 | 1,68 | 2,24 | 2,79 | 3,35 | 3,91 | 4,47 | 5,03 | 5,59 | 6,15 | 6,71 | 7,27 | 7,82 | 8,38 |
| 25 | 0,55 | 1,10 | 1,65 | 2,21 | 2,76 | 3,31 | 3,86 | 4,41 | 4,96 | 5,51 | 6,06 | 6,62 | 7,17 | 7,72 | 8,27 |
| 26 | 0,54 | 1,09 | 1,63 | 2,18 | 2,72 | 3,26 | 3,81 | 4,35 | 4,90 | 5,44 | 5,99 | 6,53 | 7,07 | 7,62 | 8,16 |
| 27 | 0,54 | 1,07 | 1,61 | 2,15 | 2,69 | 3,22 | 3,76 | 4,30 | 4,84 | 5,37 | 5,91 | 6,45 | 6,99 | 7,52 | 8,06 |
| 28 | 0,53 | 1,06 | 1,59 | 2,12 | 2,66 | 3,19 | 3,72 | 4,25 | 4,78 | 5,31 | 5,84 | 6,37 | 6,90 | 7,43 | 7,96 |
| 29 | 0,52 | 1,05 | 1,57 | 2,10 | 2,62 | 3,15 | 3,67 | 4,20 | 4,72 | 5,25 | 5,77 | 6,30 | 6,82 | 7,35 | 7,87 |
| 30 | 0,52 | 1,04 | 1,56 | 2,08 | 2,59 | 3,11 | 3,63 | 4,15 | 4,67 | 5,19 | 5,71 | 6,23 | 6,74 | 7,26 | 7,78 |

FIGURE 5

Dylight® 680-NHS  Dylight® 800-NHS

DY-782

LABELLED SILICA-BASED NANOMATERIAL WITH ENHANCED PROPERTIES AND USES THEREOF

RELATED APPLICATION

The present application is a U.S. national stage application under 35 USC § 371 of PCT/EP2010/065188, filed Oct. 11, 2010, which claims the benefit of and priority to U.S. Ser. No. 61/250,247, filed Oct. 9, 2009, the contents of both of which are hereby incorporated by reference herein in their entireties.

FIELD OF INVENTION

The present invention is oriented to a novel labelled silica-based nanomaterial, in particular a novel fluorescent silica-based nanomaterial with enhanced properties.

BACKGROUND OF THE INVENTION

The ideas developed in this patent are in the field of the fluorescent materials developed these last years for many applications. The luminescent properties of different materials were developed in many application fields like laser dyes, chemicals stains or biological labeling. Photo-luminescent properties like life time, FRET, polarization fluorescence, multiphotons excitation, phosphorescence or quenching were studied and lead to specific developments that enlarged the number of applications especially in biochemistry, in physics and telecom.

A non exhaustive list of the materials available for the different applications can be: organic dyes, organo-metallic molecules, metallic nanoparticles, rare earth complexes, lanthanides or metallic alloys, used as free molecules or as colloidal dispersions.

Each kind of material has its specificities, its properties and its limitations. Usually the choice of material is conditioned by the application requirements.

The idea here is to propose the most versatile material that should combine most of the advantages coming from the different materials, and that will considerably reduce the known disadvantages, like photostability, chemical stability or no expected biological interactions. In this application, the proposed labelled material, in particular fluorescent material, is based on silica nanoparticles. A lot of literature references are already describing fluorescent silica nanoparticles, but as they used the TEOS (tetraethyl orthosilicate) route, the nanoparticles are porous, which affect the chemical stability and the physical properties. In addition, the TEOS route will never allow the synthesis of particles with less than 15 nm diameter.

Silica nanoparticles were described for the first time by Stöber in 1968, and different patents followed (Unger and al in 1988, Border and al in 1991) to improve the particles synthesis, using the TEOS route. The main improvement was the reduction of porosity (but not fully eliminated), and the reduction of polydispersity. The method was extensively used to encapsulate different materials like organic dyes, inorganic dyes, metallic nanoparticles (iron oxide, ZnO . . . ), and the silica porosity was used as an advantage in silver (or iron oxide) core-silica shell structures, to dissolve the core and obtain hollow silica shells. In our case, this porosity is a real issue for the long term stability of the materials we target.

More recently, new silica based nanoparticles using silicate route were optimized by Persello (1994, then 1999). In this work, Persello demonstrated the capability to produce highly dense nanoparticles of different sizes from 1 nm to few tenths of nm in diameter. The particles are then non porous, and very well defined; the author claims applications in catalysis, and solid support chemistry. In his whole work, the functionalization was done on the surface of the particles, and never in the core. Moreover, he never functionalized his particles with fluorophores.

SUMMARY OF INVENTION

We claim the invention of silica nanoparticles with a labelled core, in particular fluorescent core, using the silicate route for the particles synthesis, the process for preparing them and the uses thereof.

The present invention relates to a method for making a nanoparticle comprising a core and a first label, comprising the steps of:
(a) providing a first label bound to a first molecule comprising silane thereby forming a silane functionalized label;
(b) providing a first solution comprising free silicon-containing molecules;
(c) mixing the silane functionalized label and the first solution to form a first mixed solution;
(d) reducing the pH of the first mixed solution thereby allowing conditions for the formation of covalent bonds among the silicon-containing molecules to form silica within which the first label is covalently bound, thereby nucleating the core;
(e) allowing sufficient time for the core to grow until stopped.

Preferably, step (d) includes adding an ion-exchange resin to the first mixed solution, thereby to reduce the pH.

Preferably the silane comprises APTES, APTMS, MPTMS, and/or MPTES.

The method may further comprise several steps:
(f) mixing the grown core with a second solution comprising free silicon-containing molecules and preferably comprising a second label to form a second mixed solution;
(g) reducing the pH of the second mixed solution thereby growing a shell;
(h) allowing sufficient time for the shell to grow until stopped.

Optionally, the second solution may further comprise a second label.

Steps (f) through (h) may be repeated one or more times, and the second solution may comprise a label different than the first or preceding labels during each repeat.

The method may further comprise the steps of
(i) optionally adding a functionalizing agent surrounding the shell to form a functionalized shell, the functionalizing agent preferably comprising silanes, maleimides, thiols, and/or amines, and
(j) tuning one or more properties of the nanoparticle by grafting one or more surface molecules, preferably comprising a polymer, protein, antibody, antigen, sugar, PEG, organic molecule, and/or enzyme, to the shell or, if present to the functionalized shell.

The free silicon-containing molecules may comprise sodium trisilicate, sodium orthosilicate, sodium pyrosilicate, or hydrates thereof.

The growth of the core and/or the shell may be stopped by depletion of a constituent, addition of a quenching reagent, changing temperature, and/or changing pH.

The present invention further relates to a nanoparticle obtainable or obtained by the method above. The nanoparticle may have a diameter of 500 nanometers or less, 400 nanometers or less, 300 nanometers or less, 200 nanometers or less, 100 nanometers or less, 50 nanometers or less, 25 nanometers or less, 15 nanometers or less, 10 nanometers or less, or 5 nanometers or less, 2.5 nanometers or less, or less than 1 nanometer.

The first label, and more generally the label, may comprise an organic molecule, an organic dye, an inorganic dye, an inorganic molecule, a magnetic particle and/or a radioactive compound. In an embodiment, the first label is a fluorescent dye, or phosphorescent dye, preferably a fluorescent dye.

The core of the nanoparticle may further comprise a second label bound to silica and/or the shell, if present, may further comprises a third label and/or, optionally, a fourth label or no label. The first label, second label, third label, and fourth label each differ from one or more of the other. Alternatively, any two or more of the first label, second label, third label, and fourth label are the same.

The first label, and more generally the label, may be a fluorescent label having a tunable fluorescence polarization, in particular (a) by controlling a density of, or distances between, the fluorophores; (b) by adding a metal to the core and/or the shell; (c) based on the diameter; and/or (d) by controlling a ratio of the first label and a second label that is bound to the silica in the core, in the shell, and/or on a surface of the shell.

The first label, and more generally the label, may be covalently bound to the silica, for instance via a precursor made by the reaction between an aminopropylsilane and dye-NHS or dye-ITC or a precursor made by the reaction between a mercaptopropylsilane and dye-maleimide. Alternatively, the first label, and more generally the label, may be non-covalently bound to the silica, for instance via an electrostatic interaction.

The core, the shell, or both may be non-porous.

The nanoparticle preferably has a diameter of between 2 nanometers and 15 nanometers.

The nanoparticle may comprise an additional layer of functionalizing molecules, for instance selected from the group consisting of silanes, maleimides, thiols, amines functions, polymers, proteins, antibodies, antigens, sugars, PEGs, organic molecules, and enzymes, or be grafted with functionalizing molecules.

The present invention further relates to a method, comprising the steps of:
(a) attaching the nanoparticle according to the invention to a biological entity, preferably comprising tissue, tumor, eukaryotic, archaea or prokaryotic cell—such as bacterium—protein, antigen, DNA, RNA, or virus, via the surface functionalizing molecules; and
(b) detecting the label.

The present invention further relates to a method, comprising the steps of:
(a) providing a microfluidic device;
(b) providing at least a first nanoparticle as described above having the first label within a first droplet within the device and a second nanoparticle as described above having a second label within a second droplet within the device;
(c) detecting the first label and second label within the device, the detection being preferably done within the device.

The first and the second labels, and more generally the labels, may have a different property, such as intensity; excitation and/or emission wavelength; and/or fluorescence polarization, absorption, and/or fluorescence lifetime.

The present invention further relates to a microfluidic droplet comprising nanoparticles according to the invention. The droplet may be disposed within a microfluidic device.

The present invention further relates to a composition comprising nanoparticles according to the invention.

The nanoparticles or compositions according to the invention may be used for sample coding (in particular microfluidic droplets coding), for material doping, for labelling a molecular probe or tagging a molecule or compound of interest.

The present invention further relates to a nanoparticle, wherein the nanoparticle comprises a core comprising silica and a first label bound to silica and has a diameter of 15 nanometers or less. The nanoparticle may further comprise a shell, preferably comprising, in particular consisting of, silica, surrounding the core. The core may further comprise a second label bound to silica and/or the shell, if present, may further comprise a third label and/or, optionally, a fourth label, or no label.

The first label may be a fluorescent label having a tunable fluorescence polarization, in particular (a) by controlling a density of, or distances between, the fluorophores; (b) by adding a metal to the core and/or the shell; (c) based on the diameter; and/or (d) by controlling a ratio of the first label and a second label that is bound to the silica in the core, in the shell, and/or on a surface of the shell.

The core, the shell if present, or both are non-porous.

BRIEF DESCRIPTION OF THE DRAWINGS

FIG. 5: Calculation of the mean distance between fluorophores in nanoparticles as a function of the particles size and the number of fluorescent molecules.

DETAILED DESCRIPTION OF INVENTION

Figure 1:
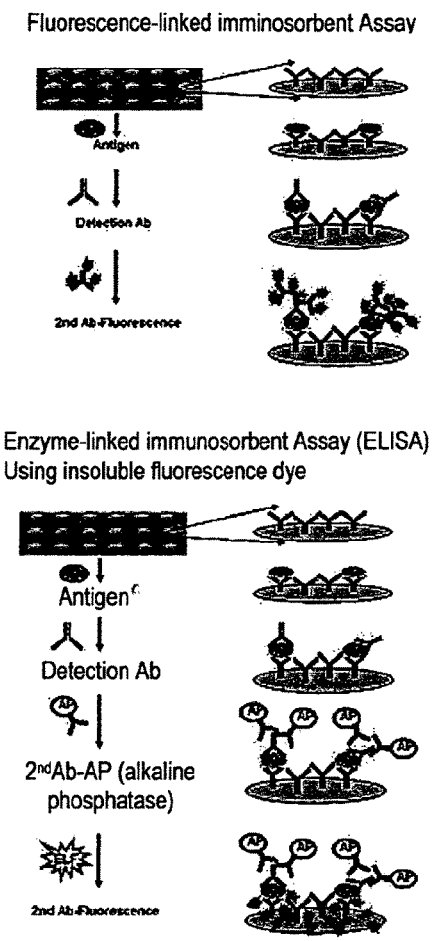
FIG. 1: Illustration of uses of fluorescent marker for microarrays
Figure 1:
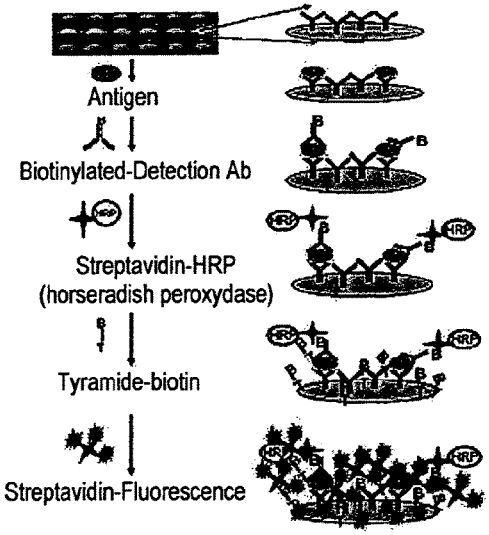
Figure 1:
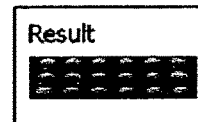

In a particular embodiment, we propose in the following description a silicate route to prepare dense nanoparticles between 2 and 15 nm in diameter that embed labels or dyes, such as fluorescent molecules. The resulting materials get an incomparable photostability and chemical stability. The silica surface gives the flexibility to tune the properties of the material by improving its colloidal stability in buffer solutions by grafting polymers like PEG (polyethylene glycol), or in organic solvents by grafting short hydrophobic chains. In polymer-based fiber applications, the nanoparticles could be used as doping materials, the contents and the surface treatment can be easily tunable to improve properties.

Therefore, the present invention relates to a nanoparticle, wherein the nanoparticle comprises a core comprising silica and a first label bound to silica, and has a diameter of 25 nanometers or less. The nanoparticle may also comprise a core comprising other label(s) bound to silica.

In a particular embodiment, the core of the nanoparticle is made of silica and labels.

In a particular embodiment, the nanoparticle may comprise more than one label in its core.

For instance, the invention also contemplates nanoparticles comprising two, three, four or five distinct labels. The core may comprise a second label bound to silica and/or the shell may comprise a third label and/or, optionally, a fourth label, or no label. The first label, second label, third label, and fourth label may each differ from one or more of the other or be the same.

Preferably, the different labels included in a nanoparticle can be distinctly detectable. For instance, for two distinct fluorescent labels, their emission wavelengths are sufficiently distinct to be simultaneously detected without significant optical crosstalk. The rules to select such different labels are well-known by the one skilled in the art. For example, a combination of FITC (fluoresceine-ITC), Rhodamine B ITC, Dylight 680-NHS and one dye among Dylight 800-NHS, CF770 NHS, DY-782-NHS may be used.

In an alternative embodiment, the present invention relates to a set of several nanoparticles, the set including nanoparticles comprising different labels. For instance, such a set may include a first group of nanoparticles comprising a first label, a second group of nanoparticles comprising a second label, etc. The set may include from two to ten distinct groups of nanoparticles, preferably from two to seven distinct groups of nanoparticles, more preferably from two to five distinct groups of nanoparticles. More preferably, the labels are fluorescent dyes or molecules. The fluorescent dyes or molecules may be chosen so as to be distinctly detectable. For instance, their emission wavelengths are sufficiently distinct to be simultaneously detected. The rules to select such different labels are well-known by the one skilled in the art. For example, a combination of FITC, Rhodamine B ITC, Dylight 680-NHS and one dye among Dylight 800-NHS, CF770 NHS, DY-782-NHS may be used.

In another embodiment, the present invention relates to a set of several nanoparticles, the set including nanoparticles comprising different interacting labels. For instance, such a set may include a first group of nanoparticles comprising a first fluorescent label and a second group of nanoparticles comprising a second label capable of quenching the first fluorescent label. Alternatively, such a set may include a first group of nanoparticles comprising a first fluorescent label and a second group of nanoparticles comprising a second fluorescent label having its absorption wavelength overlapping with the emission wavelength of the first fluorescent label, thereby allowing fluorescent transfer (FRET technology). For example, a combination of Dylight 680 and Dylight 750 may be used, as well as a combination of FITC and RhBITC (Rhodamine B-ITC).

The label comprises an organic molecule, an organic dye, an inorganic dye, an inorganic molecule, a magnetic particle and/or a radioactive compound.

Among the dyes or label that may be used in the present application, may be cited organic dyes, organo-metallic molecules, inorganic dyes, magnetic particles, radioactive compounds, metallic nanoparticles, rare earth complexes, lanthanides or metallic alloys. In the present invention, the terms "dye" and "label" may be indifferentially used to qualify these molecules.

These terms are intended to refer to detectable molecules.

Figure 18:
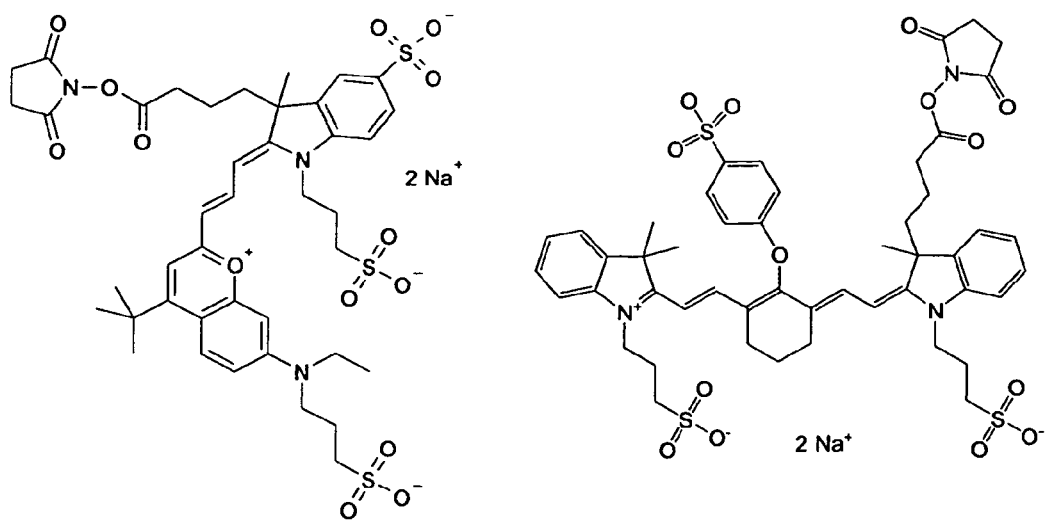
FIG. 18: Chemical structures of Dylight® 680-NHS, Dylight® 800-NHS and DY-782.
Figure 18:
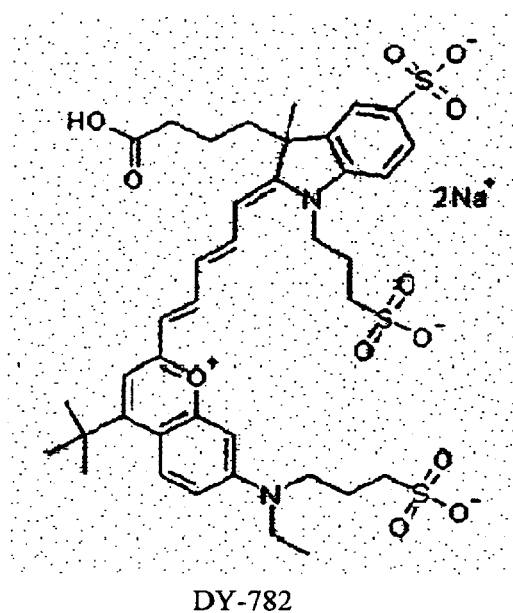

Preferably, the label is a fluorescent molecule or dye. In particular, the organic and/or inorganic dyes or molecules may be chosen among fluorescent dyes such as rhodamine B ITC, fluorescein ITC, biphotonic fluorophores such as fluorenyl based dyes and amine-reactive dyes such as dyes of the Dylight® and Alexa® series. Specific dyes that may be used are Dylight 680 NHS, Dylight 800 NHS, IRDye 800CW NHS, CF 770 NHS, DY-782, IRDye 800RS NHS, CF 790 NHS, and mixtures thereof. The chemical structures of Dylight® 680-NHS, Dylight® 800-NHS and DY-782 are provided on FIG. 18.

Preferably, the dye is chosen among rhodamine B ITC, Dylight 680 NHS, DY-782-NHS and CF 770-NHS.

The dye may alternatively be chosen among amine or maleimide derivatives of ATTO488 (Sigma-Aldrich Co, Missouri, USA), BODIPY FL (Invitrogen Corp. California, USA), DyLight 488 (Pierce Biotechnology, Inc. Illinois, USA), Sodium fluorescein, DY-682 (Dyomics GmbH, Jena, Germany), green fluorescent protein (GFP) and derivatives such as EGFP, blue fluorescent proteins (EBFP, EBFP2, Azurite, mKalama1), cyan fluorescent proteins (ECFP, Cerulean, CyPet) and yellow fluorescent proteins (YFP, Citrine, Venus, YPet), DsRed and derivatives thereof, Keima and derivatives thereof.

The dye may alternatively be chosen among fluorescent dyes based on xanthene, benzo[a]xanthene, benzo[b]xanthene, benzo[c]xanthene, coumarin, benzocoumarin, alizarin, azo, phenoxazine, benzo[a]phenoxazine, benzo[b]phenoxazine, benzo[c]phenoxazine, naphthalimide, naphtholactam, azolactone, methyne, oxazine, thiazine, diketopyrrolopyrrole, quinacridone, thioepindo line, lactamimide, diphenylmaleimide, acetoacetamide, imidazothiazine, benzanthrone, phthalimide, benzotriazole, pyrimidine, pyrazine, triazine, acridin, oxazine, cyanine, thiazol, anthraquinone, azamethine, polyene, oxonol, benzimidazol or indolenine.

Another preferred label is also a fluorescence quencher, for example belonging to the following families: Dabcyl, QXL, IRDye QC or QSY.

The label may alternatively be chosen among phosphorescent dyes or molecules such as Rhodamine 6G, eosin, platinum porphyrins, organometallic complexes containing osmium, ruthenium, iridium or platinum.

In a first embodiment, the nanoparticle's label may be covalently bound to the silica. More preferably, the label is covalently bound to the silica via an aminopropylsilane+dye-NHS or dye-ITC precursor or a mercaptopropylsilane+dye-maleimide precursor. In an alternative embodiment, the nanoparticle's label may be non-covalently bound to the silica. Preferably, the label is non-covalently bound to the silica via an electrostatic interaction.

More specifically, fluorescent properties may be obtained by including fluorescent organic or inorganic dyes. The dyes may be bound to the silica:

With a covalent bound, for instance via an (aminopropylsilane+dye-NHS (N-hydroxysuccinimide) or dye-ITC (isothiocyanate)) precursor or a (mercaptopropylsilane+dye-maleimide) precursor, Or with a non covalent bound, for instance via electrostatic interactions (silica is minus charged, the embedded molecule can be plus charged).

By (X+Y) precursor is designed a precursor made by the reaction between X and Y entities.

For instance, X may be aminopropylsilane and Y dye-NHS (N-hydroxysuccinimide) or dye-ITC (isothiocyanate). Alternatively, X may be mercaptopropylsilane and Y dye-maleimide.

Different strategies are described in the literature to produce fluorescent materials using organic or inorganic dyes. Some of them used big particles, for instance with a diameter superior to 25 nanometers, others used nanoparticles based on metals, rare earth, organometallic, or organic dyes.

The quantity of dye or label to be used in the core of the nanoparticle can vary in a wide range depending on the desired nanoparticles properties. For instance, the [dye]/[silane] molar ratio may be comprised between 1/160 and 1/10, in particular around 1/20.

Preferably, for a better quality of the nanoparticles, the label or dye of the nanoparticle core is homogenously dispersed within the silica.

In a preferred embodiment, the nanoparticle further comprises a shell surrounding the core.

By a shell is intended at least a first layer covering the silica core. Preferably, the shell comprises or consists in silica. Alternatively, the shell comprises or consists in a polymer.

Optionally, the polymer may be functionalized. Such a polymer may be, for instance, an acrylic polymer or a copolymer including acrylic monomers, poly-L-lysin, polystyrene, PMMA (polymethyl methacrylate), polybutadiene, biopolymers.

In a first embodiment, the shell is devoid of label or dye. In particular, when the core label is a fluorescent molecule or label, the shell does not include a fluorescent label.

In an alternative embodiment, the shell may include a label, distinct or not from the core label.

Preferably, the label is homogenously dispersed in the shell. In particular, the nanoparticles may have a shell comprising several successive layers (i.e., silica layer), each layer including a label (preferably, a fluorescecent label or dye) distinct or not from the labels included into the nanoparticles core and into the other shell layers. The rules for selecting the shell label are the same than those used for selecting several labels to be included in the core. The nanoparticles may also have a shell comprising several successive layers (i.e., silica layer), some including a label and other(s) not.

Optionally, the nanoparticle comprises an additional layer of functionalizing molecules or is grafted with functionalizing molecules. The functionalizing molecules may be selected from the group consisting of silanes, maleimides, thiols, amines functions, polymers, proteins, peptides, aptamers, folic acid, antibodies, antigens, sugars, PEGs, organic molecules, enzymes, mixtures thereof and derivatives thereof.

In particular, the shell may be treated for functionalizing its surface. Then, the shell surface may be functionalized with molecules to increase the nanoparticles solubility in a solvent (e.g., water or organic solvents), their colloidal stability (e.g., in a buffer solution), or for providing them to a binding ability to molecules of interest. For increasing the solubility in organic solvents, the nanoparticles may be functionalized with short hydrophobic chains. For increasing the colloidal stability, the nanoparticles may be functionalized with polyethylene glycol (PEG) chains. The short hydrophobic chains or PEG chains may be themselves functionalized for providing them to a binding ability to molecules of interest. Molecules for providing a binding ability to molecules of interest may be selected from the group, but are not limited thereto, consisting of a protein, an antibody, a fragment or a variant thereof (i.e., having a binding specificity to molecules of interest), a nucleic acid (e.g., single or double chains, RNA, DNA, RNA/DNA hybrid, analogs thereof; a probe or primer), an antigen (e.g., tumor antigen, viral antigen, bacterial antigen, and the like), an enzyme (e.g., luciferase, $\beta$-galactosidase, phosphatase), an enzyme substrate, a reporter molecule, a ligand (e.g., cell ligand, receptor ligand), streptavidin, avidin, biotin and the like, a drug and a sugar (e.g., polysaccharide).

Accordingly, the nanoparticles of the invention are preferably formed of:
  a core obtained by including at least one label in silica,
  a first cover layer of silica, also designated as a shell, and
  optionally an additional layer of functionalizing molecules.

Figure 2:
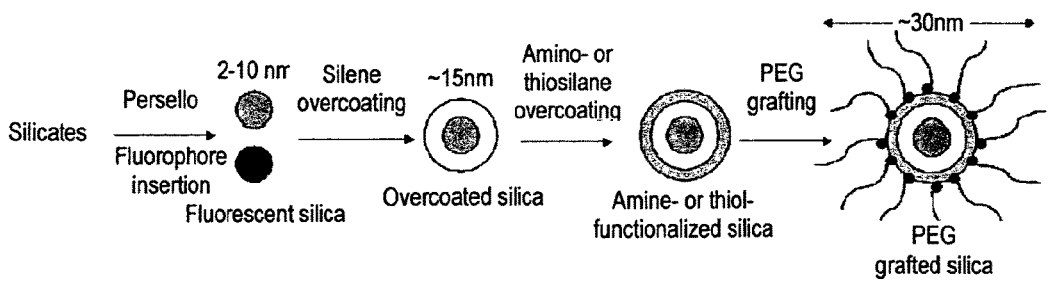
FIG. 2: Synthesis strategy overview to produce stable, fluorescent silica nanoparticles.

The structure of particles is detailed on FIG. 2.

In an embodiment, the diameter of the nanoparticles (including the core+silica shell) is 25 nm or less. For instance, the diameter of the nanoparticles is of 20 nanometers or less, 15 nanometers or less, 10 nanometers or less, 5 nanometers or less, 2.5 nanometers or less, or less than 1 nanometer. In particular, the diameter of the nanoparticles is comprised between 2 and 15 nm, preferably between 2 and 10 nm, in particular between 2.5 and 4.5 nm. The diameter can be modulated by modulating the number of silica overcoatings (OC) or the thickness of the shell.

In another embodiment, the diameter of the nanoparticles is 500 nm or less, 400 nm or less, 300 nm or less, 200 nm or less, 100 nm or less, 50 nm or less, 25 nm or less, 15 nm or less, 10 nm or less, 5 nm or less, 2.5 nm or less, or less than 1 nm.

Preferably, the nanoparticles of the invention have a core or a shell which is non-porous.

More preferably, the nanoparticle core is non-porous silica. Alternatively, the shell may be non-porous, in particular non-porous silica. Still more preferably, both the core and the shell of the nanoparticle are non-porous, in particular non-porous silica.

Preferably, the nanoparticles are essentially spherical.

The nanoparticles of the invention are obtainable, or obtained, by the synthesis process described in the "synthesis protocol" section below.

When the dye is fluorescent, the main application of this kind of material uses its enhanced fluorescence properties.

The nanoparticle of the invention may be used in a large number of applications. In particular, all the applications involving the detection of a label, in particular a fluorescent label or dye, are relevant for the nanoparticles. Briefly, the nanoparticles of the invention may be used for sample coding (in particular coding of microfluidic droplets), for material doping, for labelling a molecular probe or tagging a molecule or compound of interest. Examples of applications are detailed below. The nanoparticules may be used as marker, in particular biomarker, for in-vivo imaging, in microscopy (in particular fluorescence microscopy), as biosensor, in FRET, ELISA, quenching, fluorescence polarization, immunofluorescence, immunohistochemistry experiments, as optical probes, as diagnostic tools or for bioanalytical applications, as luminescent signal amplifiers, for mechanical reinforcement, in LED lighting, in LASERs, displays and the like. Those applications are well-known by the one skilled in the art.

More particularly, the present invention relates to a composition comprising nanoparticles of the invention, or a set of nanoparticles as disclosed above. The composition may be a diagnostic composition. It also relates to micro fluidic droplets including nanoparticles of the invention, or a set of nanoparticles as disclosed above.

In particular, the present invention relates to a method, comprising the steps of:
(a) attaching the nanoparticle of the invention to a biological entity via the surface functionalizing molecules, or creating an interaction between both; and
(b) detecting the label.

Similarly, the present invention relates to a method for detecting a biological entity in a sample, comprising
(a) providing a nanoparticle of the invention functionalized with a moiety capable of binding the biological entity to be detected;
(b) contacting the nanoparticle with the sample; and
(c) detecting the binding of the nanoparticle to the biological entity in the sample.

The biological entity may comprise tissue, tumor, eukaryotic, archaea or prokaryotic cell (such as bacterium), protein, peptide, antibody, receptor, antigen, antibody, enzyme, nucleic acid (such as DNA or RNA) or virus. The moiety is preferably capable of specifically binding the biological entity. The sample may be immobilized on a solid support. Typical pairs of binding moiety/biological entity can be streptavidin/biotin, antigen/antibody, ligand/receptor, enzyme/substrate, nucleic acid/nucleic acid, nucleic acid/DNA or RNA binding protein, and the like.

Enhanced Fluorescence Emission

Fluorescent dye encapsulation in this non porous silica beads induce an enhancement of the emission rate, which was never previously observed in a bead that small, as small as the beads of the present invention. Indeed, a decrease of the fluorescence lifetime ($\tau=1/(K_{rad}+K_{non-rad})$) increases the quantum yield of the dye embedded in the nanoparticles ($Q=K_{rad}/(K_{rad}+K_{non-rad})$).

FIGS. 14 to 17 present the absorbance and fluorescence spectra obtained for different dyes both free and embedded in silica nanoparticles according to the invention. These spectra clearly evidence the fluorescence of the embedded dye is enhanced.

High FP

The fluorescence polarization (FP) properties of nanoparticles of the invention are also an interesting feature.

The principle of FP in fluorescent SNPs (silica nanoparticles) has been previously reported in specific literature. Without wishing to be bound to any theory, the immobilization of the fluorophore in a very dense particle decreases its mobility drastically, which leads to the increase of the steady state fluorescence polarization. Furthermore, the tiny size of the nanoparticles and the NIR emission greatly reduces uncontrolled depolarization induced by the light scattering.

FP Tunability by FRET

The fluorescence polarization can be tuned by playing on Förster Resonance Energy Transfer (FRET) within 2 fluorophores A and B, the emission spectrum of A overlapping the absorption spectrum of B. Thus, chromophore A (donor) may transfer energy to chromophore B (acceptor) with another orientation, which contributes to depolarize the signal. Note than A and B can be the same fluorophore if its absorption and emission spectra overlap: in this case the phenomenon is called Homo-FRET.

The theoretical calculation of the depolarization fluorescence by HomoFRET properties was described in the literature by L. W. Runnels and S. F. Scarlata. The calculation takes into account the spectral properties of the fluorophore, the random orientation of the dyes, the refractive index of the dispersant media, and the number of molecules pairs (clusters) interacting by FRET.

A full description of this FRET phenomena in nanoparticles was already described these last years, but the particles used were always prepared by TEOS route. That means that the long term storage properties of this kind of porous material cannot be guaranteed, and the porosity can induce long term photodestabilization of the dyes encapsulated in the nanoparticles. In addition, in the literature, authors who tried to observe the fluorescence polarization decrease with tiny particles (<10 nm in diameter) never managed to achieve it.

Based on the theoretical simulation (see details in the examples), we can estimate the minimum number of fluorescent molecules per bead of a certain size necessary to drop down the FP signal around 50 mP.

Via the silicate route for particles of 2.5 nm diameter, the FP can be decreased from 410 mP to 350 mP, by increasing the dye concentration. Additionally, increasing the size of nanoparticles up to 15 nm affords a decrease in FP to 50 mP. This allows filling more fluorescent molecules per particle.

The theoretical calculations estimate the best conditions to maximize the HomoFRET in each particle, and lower the FP value to 50 mP: a good working range appears to be 20 dye molecules in 15 nm diameter nanoparticles. 15 nm size particles are accessible by the silicate route synthesis. And including 20 molecules in the beads means that we will get enough clusters (>4) for all the beads, especially if we consider the distribution of molecules through the particles as following the Poisson distribution. And the mean the distance between clusters will be in average around 4.4 nm, which is around $0.8 \times R_0$ (the best compromise between FRET and self quenching).

Accordingly, the present invention relates to a method for detecting binding or short distance between two elements in a sample, comprising:
- providing a first nanoparticle of the invention with a first fluorescent label, said nanoparticle being functionalized with a first moiety capable of binding to one of the two elements;
- providing a second nanoparticle of the invention with a second fluorescent label, said nanoparticle being functionalized with a second moiety capable of binding to the other of the two elements, wherein the emission spectrum of the first fluorescent label overlaps the absorption spectrum of the second fluorescent label;
- contacting the sample with the first and second nanoparticles; and,
- detecting the fluorescence of the second fluorescent label after an excitation of the first fluorescent label, the fluorescence detection being indicative of the short distance between two elements.

The invention further relates to a kit for detecting the distance between two elements, the kit comprising first nanoparticle of the invention with a first fluorescent label, said nanoparticle being functionalized with a first moiety capable of binding to one of the two elements; and a second nanoparticle of the invention with a second fluorescent label, said nanoparticle being functionalized with a second moiety capable of binding to the other of the two elements, wherein the emission spectrum of the first fluorescent label overlaps the absorption spectrum of the second fluorescent label.

Hetero FRET Assays

The previous description described only the HomoFRET phenomenon, that can be used to reduce the FP value of the particles. But as the seeds particles diameter (around 2.5 nm) is smaller than Förster distance (5 to 10 nm), the nanoparticles of the invention may be used for any FRET application usually used in biosensor, and bio-analytical applications. A non exhaustive list of applications is proposed in the "applications" section of this document.

Synthesis Protocol

The same protocol is used to produce the full variety of silica nanoparticles materials needed to target the multiples filed applications, such as multidimensional encoding, using fluorescence intensity and fluorescence polarization, biosensor, fiber doping, or bio-analytical applications.

The synthesis protocol followed in this work is innovative by the flexibility and the accuracy of the beads that are produced. The synthesis is split in two parts: the silica seed creation, followed or not by a shell growing on the particles, preferably using an automated system.

The seeds or cores already contain labels, preferably fluorescent molecules, (1 to 10 per seed) by including in the silicate solution the right concentration of dye or label pre-bound to a silane, in particular an alkoxysilane, such as a trimethoxysilane or a triethoxysilane, in particular APTES, APTMS, MPTMS and/or MPTES. The label or dye may be bound to the silane by a covalent bond or a non-covalent bond. Preferably, the label or dye is bound to the silane by a covalent bond. The silane is consecutively covalently bound to the silicate during the polycondensation process. Any positively charged molecule can be embedded as a label in the nanoparticles, as well as any succinimidyl ester, maleimide or silane functionalized molecule. Additional molecules that are not labels, chosen among positively charged molecules, succinimidyl esters, maleimides and silane functionalized molecules may also be embedded in the nanoparticles. The silicate may be chosen in particular among sodium trisilicate, sodium orthosilicate, sodium pyrosilicate, and hydrates thereof.

During the growing process, preferably the automated growing process, the same silane-dye molecule can be added gradually to be uniformly embedded in the whole bead core. To get a perfect sealing of the bead, the growth will be then continued during few more nm, without silane-dye addition, to create a bare shell that prevents any long-term leakage issue.

This work is distinguished from the previous ones by the quality of the particles produced, which are functionalized in the core, and the porosity of the nanoparticles is drastically reduced, which improves the chemical and optical stability for long term storage.

The produced nanoparticles are denser than those previously described and produced via the TEOS route. The density can be characterized by measuring the volume fraction of particles in solution. For instance, the density of nanoparticles synthesised via the Stöber route may be between 1.5 and 2 $g/cm^3$, in particular 1.8 $g/cm^3$. The density of nanoparticles of the invention is generally more than 2 $g/cm^3$, in particular around 2.2 $g/cm^3$.

In addition, the synthesis protocol is easy to implement since only a rough filtration is required to purify the nanoparticles produced, instead of a full dialysis or ultrafiltration for Stöber protocol.

Accordingly, the present invention relates to a method for making the nanoparticle of the invention, comprising the steps of:
- (a) providing a first label bound to a first molecule comprising silane, thereby forming a silane functionalized label;
- (b) providing a first solution comprising free silicon-containing molecules;
- (c) mixing the silane functionalized label and the first solution to form a first mixed solution;
- (d) reducing the pH of the first mixed solution thereby allowing conditions for the formation of covalent bonds among the silicon-containing molecules to form silica within which the first label is covalently bound, thereby nucleating the core;
- (e) allowing sufficient time for the core to grow until stopped.

In a particular embodiment of the method, in step (a), more than one first label bound to a first molecule comprising silane is provided. Indeed, two, three, four or five distinct labels bound to a first molecule comprising silane may be provided. Preferably, the different labels included in a nanoparticle can be distinctly detectable. For instance, for two distinct fluorescent labels, their emission wavelengths are sufficiently distinct to be simultaneously detected. The rules to select such different labels are well-known by the one skilled in the art. Preferably, the label comprises an organic molecule, an organic dye, an inorganic dye, an inorganic molecule, a magnetic particle and/or a radioactive compound. More preferably, the label is a phosphorescent or fluorescent molecule or dye, still more preferably a fluorescent molecule or dye.

Preferably, step (d) includes adding an ion-exchange resin to the first mixed solution, thereby to reduce the pH. For instance, the an ion-exchange resin is an acidic exchange resin such as Amberlite® IR-120 (Aldrich), Amberlite IRN77, Dowex HCR-W2, Dowex Marathon. Preferably, the silane is as detailed above and may be selected from the group consisting of APTES, APTMS, MPTMS, and/or MPTES.

Preferably, the free silicon-containing molecules may comprise all common types of silicates, such as metasilicates, disilicates, and favourably alkali metal silicates such as sodium silicate or potassium silicate. This includes sodium trisilicate, sodium orthosilicate, sodium pyrosilicate, or hydrates thereof. If sodium silicates are used, the $SiO_2$/$Na_2O$ weight ratio is preferably between 2 and 4.

Preferably, in step (c), the quantity of label can vary in a wide range depending on the desired nanoparticles properties. For instance, the [dye]/[silane] molar ratio may be comprised between 1/160 and 1/10, in particular around 1/20.

When the nanoparticle comprises a silica shell, the method further comprises
(f) mixing the grown core with a second solution comprising free silicon-containing molecules to form a second mixed solution;
(g) reducing the pH of the second mixed solution thereby growing a shell;
(h) allowing sufficient time for the shell to grow until stopped.

In a particular embodiment, the second solution is devoid of label, in particular fluorescent label. In an alternative embodiment, the second solution further comprises a second label. In particular, steps (f) through (h) may be repeated one or more times, and the second solution may comprise a label different than the first or preceding labels during each repeat. Preferably, the different labels included in a nanoparticle can be distinctly detectable. For instance, for two distinct fluorescent labels, their emission wavelengths are sufficiently distinct to be simultaneously detected. The rules to select such different labels are well-known by the one skilled in the art.

When the nanoparticle is functionalized, the method further comprises the steps of (i) optionally adding a functionalizing agent surrounding the shell (or core when the shell is absent) to form a functionalized shell (or core), and (j) tuning one or more properties of the nanoparticle by grafting one or more surface molecules to the shell or core when the shell is absent) or, if present to the functionalized shell. Functionalization is disclosed in details above. For instance, the functionalizing agent comprises silanes, maleimides, thiols, and/or amines. The surface molecules may be any molecule of interest and comprise molecules for increasing the solubility of the nanoparticles in a solvent (e.g., organic solvents), their colloidal stability (e.g., in a buffer solution), or for providing them with the ability to bind molecules of interest. For instance, the surface molecules may be a short hydrophobic chain optionally functionalized to be able to bind molecules of interest, a polyethylene glycol (PEG) chain optionally functionalized to be able to bind molecules of interest, a protein, an antibody, a fragment or a variant thereof (i.e., having a binding specificity to molecules of interest), a nucleic acid (e.g., single or double chains, RNA, DNA, RNA/DNA hybrid, analogs thereof; a probe or primer), an antigen (e.g., tumor antigen, viral antigen, bacterial antigen, and the like), an enzyme (e.g., luciferase, βgalactosidase), an enzyme substrate, a reporter molecule, a ligand (e.g., cell ligand, receptor ligand), streptavidin, avidin, biotin and the like, a drug and a sugar (e.g., polysaccharide). In particular, the surface molecules comprise a polymer, protein, antibody, antigen, sugar, PEG, organic molecule, and/or enzyme.

Preferably, growth of the core and/or the shell is stopped by depletion of a constituent, addition of a quenching reagent, changing temperature, and/or changing pH.

One object of the present invention is particles obtainable or obtained by the synthesis process described above.

Colloidal Stabilization

The nanoparticles produced (core+silica shell) are stable in deionized water by electrostatic repulsion. But the screening length decreases in buffer solutions due to the presence of salts. To improve the nanoparticles stability in buffered solution, the nanoparticles are stabilized via steric repulsion, using functionalizing molecules such as polymers. The best biocompatible and water soluble polymer being polyethylene glycol (PEG), different strategies are proposed for the nanoparticles surface functionalization.

The first way is by functionalization of the silica surface using APTES or MPTES (silanes) to get primary amines or thiol functions. Those functions react specifically and respectively with PEG-NHS and PEG-maleimides. It is also possible to directly graft PEG alcoxysilanes on the silanol groups at the surface. The particles become crowned with PEG, which doesn't affect the water solubility but improves the stability in buffer solution. In addition by using bifunctional PEG-polymers, the nanoparticles surfaces can be modulate to meet the application requirements, by keeping good binding properties to IGg, proteins, or cells (using NHS, maleimide, lysine, avidin functions . . . ).

The second way, is by growing the acrylic polymer, with PEG in side chain, using the radical polymerization (controlled or not), that allows the grafting of longer chains. This dense core (silica)/shell (polymer) structure is probably the most stable for long term storage. As previously described the end chain can be also functionalized to keep the same reactivity.

In order to favour their solubility in organic solvents, the NPs may be alternatively functionalized with hydrophobic molecules, in particular short hydrophobic chains. Among short hydrophobic chains that may be used to functionalize the nanoparticles may be cited short chains of triethoxy-functionalized polyethylene, polypropylene, polypropylene oxide, polyvinyl chloride, polyvinyl acetal. One of ordinary skill in the art will chose the appropriate hydrophobic chain to use in function of the properties of the solvent wherein the particles are dispersed or solubilised.

Other functionalizing molecules may be molecules containing silanes, maleimides, thiols, and amines functions, polymers, proteins, antibodies, antigens, sugars, PEGs, organic molecules, and enzymes.

Other Advantages

By varying the fluorescent molecule structure, the excitation and emission wavelengths can be tuned. By adjusting the concentration of dye molecules par particles the polarization fluorescence properties can be modulated.

Accordingly, the nanoparticles of the invention may comprise a fluorescent label having a tunable fluorescence polarization. The fluorescence polarization can be tuned though different ways, in particular (a) by controlling a density of, or distances between, the fluorophores; (b) by adding a metal to the core and/or the shell; (c) based on the diameter; and/or (d) by controlling a ratio of a first label and a second label that is bound to the silica in the core, in the shell, and/or on a surface of the shell.

Figure 26:
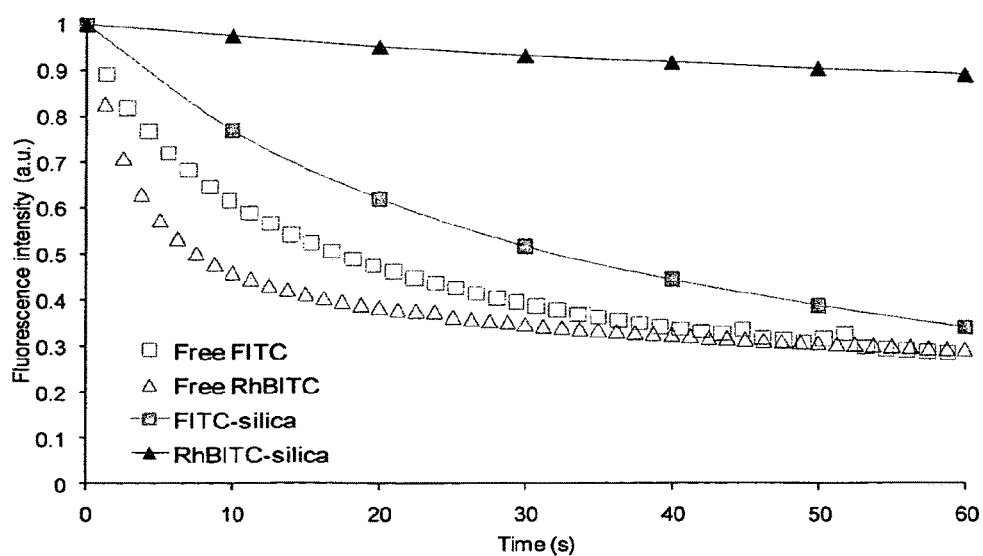
FIG. 26: Influence of silica encapsulation on the photobleaching of FITC and rhodamine B ITC.

In addition, encapsulating the dye or label in silica has two positive consequences: photobleaching is considerably reduced and quantum efficiency is enhanced. FIG. 26 compares the photobleaching of free rhodamine B ITC with that of the same dye encapsulated in silica according to the invention. The photobleaching time constant is significantly increased.

As far as barcoding in droplets, silica nanoparticles prove to be compatible with droplets, as showed on FIGS. 19 to 24: the barcodes remain stable in time.

SUMMARY OF THE ADVANTAGES

To summarize the specifications for this innovative material the following arguments are advanced:

The synthesis protocol is very easy

The dyes available for this kind of applications are very diverse

The particles size is very small, and can be tuned to reach specific needs

As they are small, the number of objects per volume units is higher

As the particles are small, they are less heavy for their guest

The particles are non-porous

The surface functionality is adjustable

The particles can be used for FRET characterization

The excitation time and the response time are in less than microsecond time scale Stability of the material in any chemical media (different pH buffers between 2 and 12, organic solvent like dimethylsulfoxide (DMSO), dimethylformamide (DMF), methanol, ethanol, acetonitrile . . . )

Inert material that will not affect the media in which they are immersed

Stability over short and long term storage (no chemical degradation, no colloidal destabilization)

High chemical resistance

The material are well dispersed in the media, resulting in a homogenous signal in sub-µm dimensions They are compatible with the biology The interactions with the biological systems is limited, and do not affect the kinetics or the mechanisms The fluorescence signal is strong Photo-stability over short and long term storage for the coding.

Applications

Application 1: Barcodes for HTS of Drug Candidates in Droplet Microfluidics

Droplet-based micro fluidics is the most promising technology to increase the sampling rate and the throughput for drug screening, diagnostics or multi-component reactions. Unfortunately, it is impossible to spatially or temporally encode the information contained within the droplets once the droplets are collected out of the chip and mixed all together.

To extend the capability of this technology, fluorescent nanoparticles according to the invention can be used as a labelling system of each reacting volume to identify the drug candidate species it contains. Assuming this volume is confined in liquid droplets mixed with millions of other droplets, it is important to identify the droplets containing the same drug candidate, and distinguish the different compositions.

For that, a digital coding system can be proposed, using fluorescent intensity. The number of codes generated by this kind of strategy is proportional to the number of discrete intensity levels that can be used, multiplied by the number of colors. Since the main applications targeted are biological systems that will be studied in the droplets, it is important to leave the whole UV-visible part of spectrum for the application. Thus the fluorescent coding systems have to be shifted as much as possible in the Near IR part.

As the window becomes very restrictive, the number of colors becomes limited. To increase the coding capability it is possible to add one more freedom axis (variable), by using the fluorescence polarization in addition to the fluorescence intensity.

The application constraints, that are the use of biological and chemical systems in high throughput droplets-based microfluidics, dictate the specifications of the nanoparticles to be developed.

An example of nanoparticles according to the invention that would be suitable for such application combines the following properties:

The excitation time and the response time are less than microsecond scale to not affect the throughput targeted;

2-10 nm particles are well dispersed in their media, giving an homogenous signal in sub-µm dimensions;

The fluorescence signal is strong enough to cover at least 20 discrete intensity levels;

For each labeling color, at least two polarizations states can be produced to create polarization levels used in the multidimensional encoding;

Silica exhibits high chemical resistance to harsh conditions (pH, temperature);

nanoparticles of the invention are inert and will not affect the chemical/biological reactions occurring in the droplet;

Once functionalized, the nanoparticles exhibit long-term colloidal stability in a broad range of chemical media (different pH buffers between 2 and 12, organic solvents like DMSO (dimethylsulfoxide), Methanol . . . );

The covalent binding of dyes in small nanoparticles enables short and long term storages in bulk and in the droplets (no exchange between droplets, no chemical degradation);

Nanoparticles of the invention show good photostability at short term (illumination by laser in droplets) and long term (storage): the coding is not degraded.

Therefore, the present invention relates to the use of nanoparticles of the invention for coding microfluidic droplets. In particular, it relates to the use of a set of nanoparticles of the invention for barcoding micro fluidic droplets.

The present invention further relates to a method, comprising the steps of:

(a) providing a micro fluidic device;

(b) providing at least a first nanoparticle of the invention having the first label within a first droplet within the device and a second nanoparticle of the invention having a second label within a second droplet within the device;

(c) detecting the first label and second label within the device.

Preferably, the first and second labels are fluorescent dyes or molecules. In particular, for the two distinct fluorescent labels, their emission wavelengths are sufficiently distinct to be simultaneously detected. The rules to select such different labels are well-known by the one skilled in the art. Of course, the method is not limited to two different labels. The system may be incremented to three, four, five or more droplets with the corresponding labels.

In an embodiment, the first and second labels, and more generally the labels, have a different property, for instance comprising intensity; excitation and/or emission wavelength; and/or fluorescence polarization, absorption, and/or fluorescence lifetime.

Preferably, detection step (c) is performed within the device.

Another object of the invention is a microfluidic droplet comprising a nanoparticle according to the invention, that may be disposed within a microfluidic device.

Application 2: Optical Probes for Fluorescent Polarization Microscopy

Nanoparticles with different FP levels but same diameter and same maximum emission wavelength may be synthesised by a process according to the invention.

Particles of each FP level can be functionalized differently (with more or less hydrophobic surfactants, or distinct antibodies, or different DNA strands for instance), then mixed and be all be injected into cells or whole organisms.

Each type of particle will go to its different target, and FP microscopy will allow differentiated visualization of each of them, using only 1 excitation wavelength.

Given that nanoparticles of the invention can be spherical and of uniform size, they are more reliable than using mixed quantum rods of different FP levels (varying their aspect ratio) whose different geometries induce different diffusion and rotation properties.

Application 3: Immunology Tests by FRET Signal Variation

Nanoparticles of the invention may be used in immunology tests.

For instance, specific antibodies may be bound to 2 nm diameter particles encapsulating 1 fluorophore A (ex: fluorescein), and all antigens may be bound to other 2 nm diameter particles containing fluorophore B (ex: rhodamine B) whose absorption spectrum overlaps the emission spectrum of fluorophore A. The other necessary condition is that fluorophore B must not be excited by the wavelength used to excite fluorophore A (ex: 488 nm).

The antigen corresponding to the chosen antibody will bind to it, the distance between both will go under FRET distance, and fluorophore energy transfer will take place, enabling fluorescence emission from fluorophore B.

Using a filter centered around fluorophore B maximum emission wavelength, the bright regions will locate the antigen specific to the chosen antibody. Moreover, the variation in fluorescence intensity will be dependent on the antibody-antigen distance.

Nanoparticles of the invention are especially suitable for this application, because once close to each other, their center-to-center distance is around 2 nm, which is below FRET distance (contrary to commercial 30 nm radius core-shell nanoparticles which could not be used). In addition, their brightness is higher and they are less sensitive to photobleaching than the free fluorophore, which is a real asset during long observations.

Application 4: Molecular Tagging to Follow Dynamic Phenomena by Fluorescence Microscopy A 2-nm fluorescent nanoparticle according to the invention may be functionalized with a marker specific to the moving target that is aimed to be observed. It binds to the target and enables the observation of its movement.

Given its small size, the fluorescent nanoparticle will have a reduced impact on the target motion, minimizing the bias. Moreover, its small size enables use of fluorescent microscopes with high-resolution in X, Y and Z axes. Finally, it will be brighter and more photostable than the corresponding free dye, and will not blink like the majority of quantum dots.

Application 5: Fluorescent ELISA Tests

Fluorescent nanoparticles of the inventionmay be functionalized with NHS endgroups, and then added to the blood plasma sample investigated. The nanoparticles bind to all the antigens. The mixture is added into wells functionalized with the antibody specific to the antigen that is being sorted. Antibody-antigen binding takes place; the well is then washed to remove all non-specific antigens, then a fluorescence measurement is performed. The fluorescence intensity will be proportional to the number of fluorescent-labeled bound antibodies.

Application 6: Fluorescent Marker for Microarrays

Fluorescent nanoparticles according to the invention may be used as fluorescent markers for microarrays. Nanoparticles covering antibodies or streptavidin or any other specific marker can be for instance used (see example on FIG. 1, from en.wikipedia.org/wiki/Antibody_microarray).

Using 2 nm particles will enable to bind more particles by antibody than with classically used 30 nm particles of the same brightness for each (containing the same number of fluorophores): the fluorescence intensity will consequently be increased, as well as the assay sensitivity.

Application 7: Near-infrared (NIR) Emitting Probe for in-vivo Imaging 2-5 nm nanoparticles containing covalently bound NIR fluorophores are potential powerful fluorescent markers for in vivo imaging: once properly functionalized, their small size will enable them to cross all types of membranes that would be impassable by particles of d>50 nm.

Moreover, NIR organic fluorophores commonly have FWHM (full-width half-maximum) values around 80 nm at 800 nm maximum emission, which is better than the ~120 nm FWHM obtained with CdTeSe/CdZnS core-shell QD at the same wavelength (ref Pons T. et al, CHEMISTRY OF MATERIALS, 21, 8, 1418-1424, 2009), enabling more multiplexing. Otherwise, CdSe/CdTe QDs with similar FWHM (ref Kim S. et al, J. AM. CHEM. SOC. 2003, 125, 11466-11467) are not biofriendly because of Cd, contrary to biocompatible silica.

Application 8: Enzymatic Assays Using FRET or Quenching.

Enzymatic assays can be performed using nanoparticles of the invention by 2 ways:

using FRET: one set of nanoparticles encapsulating fluorophore A and another set encapsulating fluorophore B (same absorption/emission spectra properties as in application 3), are functionalized separately with chemical functions so that they can later be bound 1 by 1 (ex: first set functionalized by alcohol and the second one functionalized by an activated acid, bonding of nanoparticles 1 by 1 will happen via formation of ester bonds).

Once coupled, FRET can be observed between the 2 particles: B dye is emitting fluorescence. Then, enzymatic activities of several enzymes (for instance esterases) can be monitored by measuring the decrease of fluorescence by B upon ester function cleavage, the separation of the 2 FRET moieties.

using a quencher: with the same principle, nanoparticles encapsulating quencher dyes can be covalently bound to nanoparticles encapsulating the corresponding fluorophore: fluorescence emission is measured and is indicative of the cleavage of the chemical functions. Upon enzymatic cleavage, the quencher will be released and emission from the fluorophore will increase.

Applications 9 and 10: Doped Polymeric Fibers and Doped Dye Laser

Very tiny fluorescent silica nanoparticles according to the invention are promising candidates for doped materials based on new low cost polymers or sol-gel, in optical amplification phenomenon.

Indeed, fluorescence emission is largely used to induced amplified spontaneous emission or light amplification by stimulated emission of radiation (LASER) in Liquid Dyes Laser. But recently, the interest for low cost solid polymers components (Somasundaram et al. Journal of photochemistry and photobiology, 1999, vol. 125, no, 1-3, pp. 93-98 (10 ref.), Yu et al. Optics Express 2007, Vol. 15, No. 16, p. 9989), instead of silica gels (Altman et al. IEEE Photonics technology letters 1991, vol. 3, no. 3, pp. 189-190 (5 ref.)) (as the host media) for dye lasers or optical amplification grows up. For this kind of application it is important to get read of the common issues associated to the liquid solution of free dyes, such as: concentration variation, useless solvents or photobleaching. The tiny silica nanoparticles can address the cited problems since they are water soluble, can be used at very high concentration, and the photo-bleaching is very limited. Using very tiny silica nanoparticles the scattering effect is considerably reduced. In addition, the silica surface can be easily functionalized to make it compatible with the polymeric matrix or another sol-gel thin film.

The doping with silica fluorescent nanoparticles application can be useful in the following applications, among others:

Doped Polymer Optical fiber component for optical amplification in telecommunication or in new low cost polymer LASER fiber.

New generation of Active optical waveguide or integrated components based on Sol-Gel technology for optical amplification or integrated low cost LASER.

The other very useful application field is liquid Laser. The fluorescent silica nanoparticles are one of the most promising candidates for stable dye laser. The microelectronic expansion opens the access to the droplets based microfluidic, which can generate the new generation of dye LASER. Indeed, droplets can be used like optical micro cavity if there is a high contrast index (0.2 to 0.3) between the droplets and the media, which induced whispering modes that can produce the amplification emission signal (Tang et al. Lab Chip 2009, 9, 2767-2771). The concentration variation reduction, confirmed by a better photo-stability and a reduction transport effect between droplets encapsulating the silica fluorescent nanoparticles will allow better stability in micro fluidic droplets using the dyes laser phenomenon.

EXAMPLES

Example 1

Experimental Methods—Protocols

Protocol 1:
Synthesis Strategy Overview

The synthesis optimizations were done with inexpensive fluorophores like Fluorescein isothiocyanate, or Rhodamine B isothiocyanate. Then, the protocols were transferred to the Dylight® NIR dyes.

Silane-dye Precursor Synthesis

A stock solution of dye (Fluorescein isothiocyanate or Rhodamine B isothiocyante, both Sigma Aldrich, or Dylight® 680-NHS and Dylight® 800-NHS, Thermo Scientific) functionalized with isothiocyanate, NHS or maleimide, in 99.9% anhydrous ethanol (Merck) or DMSO was prepared under nitrogen in a dry 1.7 mL microcentrifuge tube (Axygen); the final concentration was in the range of $5.10^{-4}$-$10^{-2}$ M. Between each use, the vial was stored at 4° C. away from light and moisture. If necessary, this stock solution was diluted to $5.10^{-4}$ M with anhydrous ethanol under nitrogen before use.

A sample of this diluted dye solution (in the range of 0.1 to 1 mL) was mixed under nitrogen with 3-aminopropyltriethoxysilane or 3-thiopropyltriethoxysilane, in the $10^{-5}$ to $10^{-4}$ mol/L range, keeping a ratio [dye]/[silane]=0.05. The reaction mixture was kept closed hermetically in the dark at 50° C. for 30 min.

Fluorescent Seed Particles Synthesis

A pH meter (pH 211, Hanna Instruments) was used to monitor the pH all along the reaction steps. In an opaque plastic beaker, a sodium trisilicate solution (Sigma-Aldrich) was diluted to 10% w/w with MiliQ water (Millipore SAS, Molsheim, France) under stirring: the pH reached 11.65. Then, the silane-dye reaction mixture was added: the pH did not change. 12.5 g of Amberlite® IR-120 acidic exchange resin (Aldrich) were added: the pH started dropping continuously. When pH reached 9.00, the mixture was filtered on cotton pad and the filtrate was kept under stirring in the dark overnight. After 16 hours of reaction, the pH had raised to ~10, so 0.7 g Amberlite® were added to lower the pH back to 9.00. Once this value was reached, the mixture was filtered on cotton and the filtrate kept away from light.

Dialysis

To get rid of the ungrafted dye molecules, the seed particles were dialysed in ~30 times their volume of miliQ water with a MWCO=4000 (molecular weight cutoff) cellulose dialysis membrane (Carl Roth). During dialysis, samples were stirred in the dark. This step is not compulsory for the process but was performed to check if any ungrafted dye molecules remained.

Layer-by-layer Fluorescent Cores Particles Growth

The particles growth had to be performed quickly after seed dialysis, to prevent long term loss of fluorophores from the seeds. It was performed using the same principle as the seed synthesis (condensation of silicates by acidification), adding one equivalent of silicate and silane+dye, then the appropriate amount of Amberlite® to reach pH 9. The mixture was filtered and left to react during 15 minutes, then the same operation was repeated. After adding 6 equivalents, particles had grown from 2.5 nm radius to 4.5 nm.

Continuous Fluorescent Cores Particles Growth

The previous protocol being quite time-consuming if used for particles with a greater diameter, such as 15 nm diameter particles, to the growth reaction was automated and improved by continuously adding both reagents on the seed particles solution, keeping the pH constant around 9.00 to avoid secondary nucleation or precipitation.

Figure 3:
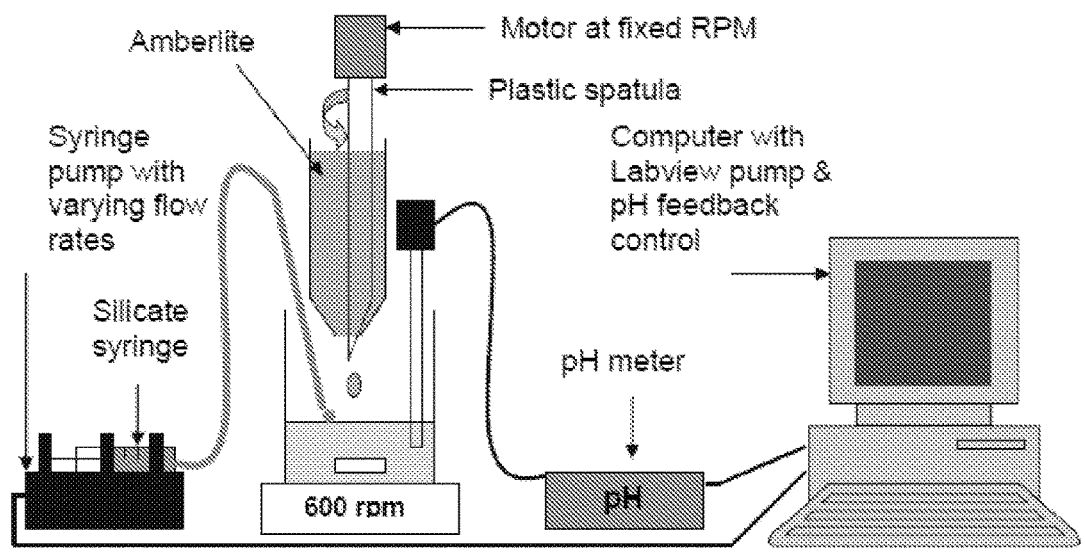
FIG. 3: Continuous synthesis setup.

The setup used is drawn on FIG. 3: Amberlite® is continuously pushed through a pierced 50 mL centrifuge tube (Corning) by a plastic spatula rotated at a fixed speed with a motor. The silicate is dispensed through a syringe and a PTFE 0.7 mm tubing pushed by a OEM syringe pump (Harvard Apparatus, Holliston, Mass.). The flow is regulated automatically to keep the pH around 9.00. To do so, a pH control program was written in Labview (National Instruments, Austin Tex.).

Protocol 2: Synthesis of Fluorescent SNPs in 4 Colors
First Step: Dissolution of the Fluorophore in Solvent For each fluorophore, a certain amount of powder was weighed in a 1.7 mL tube (Axygen) or taken as packaged (see table below); an appropriate volume of anhydrous ethanol (Merck) was added to it, to make a 5 mM stock solution. Between each use, the tubes were kept in the dark at 4° C., away from light and moisture.

|  | Provider | m (×10⁻³ g) | M (g/mol) | $V_{solv}$ (mL) |
|---|---|---|---|---|
| FITC | Sigma | 4.5 | 389.4 | 2.32 |
| RhBITC | Aldrich | 8.7 | 536.1 | 3.24 |
| Dylight 680 NHS | Thermo Scientific | 1.0 | 927.0 | 0.214 |
| Dylight 800 NHS | Thermo Scientific | 1.0 | 1027 | 0.195 |

Second Step: Coupling with Aminosilane

The ratio $n_{APTES}/n_{dye}$ used was 20/1. 2.28 μL (=9.7×10⁻⁶ mol) of aminopropyltriethoxysilane (further referred as APTES, Aldrich) were added to 97.0 μL, of fluorophore stock solution (=4.85×10⁻⁷ mol of fluorophore) and vortexed. Then, this mixture was incubated at 50° C. for 30 min in the dark.

Third Step: Synthesize the Fluorescent SNP Cores

A pH meter (pH 211, Hanna Instruments) was used to monitor the pH all along the reaction steps.

In an opaque small glass vial, 1.00 g of a sodium trisilicate solution (Sigma-Aldrich) was diluted to 10% w/w by adding it dropwise to 9.0 mL of MilliQ water (Millipore SAS, Molsheim, France) under stirring at 600 rpm: the pH reached 11.65. Then, the APTES-dye reaction mixture was added, still under stirring: the pH did not change. The final fluorophore concentration of this solution was 50 μM.

1.25 g of Amberlite IR-120 acidic exchange resin (Aldrich) was added: the pH started dropping continuously. When pH reached 9.00, the mixture was filtered on cotton pad and the filtrate was kept under stirring at 400 rpm in the dark overnight.

After 16 hours of reaction, the pH had raised to ~10, so 0.07 g Amberlite were added to lower the pH back to 9.00. Once this value was reached, the mixture was filtered on cotton and the filtrate kept away from light.

Fourth Step: Growth of the Bare Silica Shell

To the previous fluorescent cores mixture, 720 μL of sodium silicate were added to the reaction vial under stirring at 600 rpm. pH increased to about 11.35. Then, 1.25 g Amberlite IR 120 acidic exchange resin was added to lower the pH. Once it reached 9.00, the mixture was filtered on cotton and the filtrate stirred at 400 rpm during 30' in the dark. Finally, the particle diameter was measured by Dynamic Light Scattering (LB550, Horiba), giving a value of 4 nm. In this synthesis, this step was only performed once, but it is possible to repeat it several times to grow a thicker shell.

Fifth Step: PEG Grafting

First, a solution of borate buffer pH 9.2 and ionic strength 0.01M was prepared. To do so, a 0.1M solution of HCl was prepared by diluting a 1.0M stock solution (Sigma), and a 0.01M solution of sodium tetraborate was prepared by dissolving 1.006 g of anhydrous sodium tetraborate (Sigma) in 500 mL milliQ water. Then, the 0.1M HCl solution was added dropwise under pH monitoring, until pH reached a value of 9.20 (about 5.5 mL of HCl solution were needed). Finally, water was added to reach a total volume of 1.00 L.

Then, each solution of fluorescent core-shell SNPs was diluted to 0.48% w/w of silica by mixing 2.0 mL of it to 18.0 mL of borate buffer pH 9.2 in a 50 mL round bottom flask (Chemglass).

The appropriate quantity of PEG700 triethoxysilane (Gelest) to add was calculated, based on the mean surface of the core-shell nanoparticles, the volume of the solution and the surface coverage desired (here, we chose to have a coverage of 0.5 PEG chain/nm²). The final calculated weight of PEG700 silane to add was 0.128 g. This quantity was added to the diluted core-shell nanoparticles under stirring.

Finally, the round bottom flask was connected to a Dimroth condenser (Chemglass) and the mixture was stirred at 500 rpm and heated under reflux at 120° C. during 2 hours in the dark.

Finally, the reaction mixture was allowed to cool down to room temperature.

The global synthesis scheme according to protocol 2 is provided on FIG. 2.

Protocol 3: Synthesis of Fluorescent Silica Nanoparticles with Successive Overcoatings A stock solution of 10 mM FITC was prepared by dissolving 15.0 mg of FITC in 3.85 mL anhydrous DMSO (Merck). Then, this stock solution was further diluted in anhydrous ethanol to a concentration of 5×10⁻⁴ M. Then, 2.36 μL, of APTES was added to 1 mL of this solution, giving a $n_{APTES}/n_{dye}$ ratio of 20/1. The tube was vortexed and left to incubate in the dark at 50° C. for 30 min to complete the coupling reaction.

A pH meter (pH 211, Hanna Instruments) was used to monitor the pH all along the following reaction steps.

In an opaque 250 mL plastic bottle, 10.0 g (7.20 mL) of a sodium trisilicate solution (Sigma-Aldrich) were diluted to 10% w/w by adding it dropwise to 90.0 mL of MilliQ water (Millipore SAS, Molsheim, France) under stirring at 600 rpm: the pH reached 11.65. Then, the APTES-dye reaction mixture was added, still under stirring: the pH did not change.

12.5 g of Amberlite IR-120 acidic exchange resin (Aldrich) were added: the pH started dropping continuously. When pH reached 9.00, the mixture was filtered on cotton pad and the filtrate was kept under stirring at 400 rpm in the dark overnight to enable growth of the fluorescent silica cores.

After 16 hours of reaction, the pH had raised to ~10, so 0.7 g Amberlite IR 120 were added to lower the pH back to 9.00. Once this value was reached, the fluorescent cores mixture was filtered on cotton and the filtrate kept away from light.

To the previous mixture, 7.20 mL of sodium silicate were added to the reaction vial under stirring at 600 rpm. pH increased to about 11.35. Then, 1.25 g Amberlite IR 120 acidic exchange resin was added to lower the pH. Once it reached 9.00, the mixture was filtered on cotton and the filtrate stirred at 400 rpm during 30' in the dark to complete the shell growth. Finally, the particle diameter was measured by Dynamic Light Scattering (Nanosizer ZS, Malvern).

The previous shell growth/overcoating step was successively repeated again 5 times, and particle diameter was measured after each step 3 times by DLS after previously filtering samples with 0.45 μm PVDF syringe filters (Millipore).

Protocol 4: Synthesis of Silica Nanoparticles with Several Wt % of Silicate

A pH meter (pH 211, Hanna Instruments) was used to monitor the pH all along the following reaction steps. Three syntheses were performed simultaneously.

In three 250 mL plastic bottles, x grams (see table below) of a sodium trisilicate solution (Sigma-Aldrich) were diluted to x % w/w (see table below) by adding them dropwise to (100-x) mL of MilliQ water (Millipore SAS, Molsheim, France) under stirring at 600 rpm: the pH reached 11.65.

y grams (see table below) of Amberlite IR-120 acidic exchange resin (Aldrich) were added in each bottle: the pH started dropping continuously. When pH reached 9.00, the mixture was filtered on cotton pad and the filtrate was kept under stirring at 400 rpm overnight to enable growth of the silica cores.

| Sample | A | B | C |
|---|---|---|---|
| x | 10.0 | 15.0 | 20.0 |
| y | 11.92 | 17.88 | 23.84 |

After 16 hours of reaction, the pH had raised to ~10, so 0.7 g Amberlite IR 120 were added to lower the pH back to 9.00. Once this value was reached, the fluorescent cores mixture was filtered on cotton.

The particle diameter was measured by Dynamic Light Scattering (Nanosizer ZS, Malvern) on the three samples previously filtered with 0.45 μm PVDF syringe filters (Millipore).

Protocol 5: Synthesis of Fluorescent Silica Nanoparticles Containing Several Amounts of Fluorophore Stock solutions of 10 mM FITC and RhBITC were prepared by dissolving 15.0 mg FITC or 12.0 mg RhBITC in respectively 3.85 mL and 2.23 mL anhydrous DMSO. Then, these stock solutions were further diluted in anhydrous ethanol to a concentration of $5 \times 10^{-4}$ M. Then, x μL of APTES (see table below) were added to y mL (see table below) of these solutions, keeping a $n_{APTES}/n_{dye}$ ratio of 20/1. The tube was vortexed and left to incubate in the dark at 50° C. for 30 min to complete the coupling reaction.

A pH meter (pH 211, Hanna Instruments) was used to monitor the pH all along the following reaction steps. Three syntheses were performed simultaneously.

In eight opaque 100 mL plastic bottles, 5 grams of a sodium trisilicate solution (Sigma-Aldrich) were diluted to 10% w/w (see table below) by adding them dropwise to 45 mL of MilliQ water (Millipore SAS, Molsheim, France) under stirring at 600 rpm: the pH reached 11.65. Then, the APTES-dye reaction mixtures were added to each vial, still under stirring: the pH did not change.

11.92 grams (see table below) of Amberlite IR-120 acidic exchange resin (Aldrich) were added: the pH started dropping continuously. When pH reached 9.00, the mixture was filtered on cotton pad and the filtrate was kept under stirring at 400 rpm overnight to enable growth of the silica cores.

| Sample | A1 (FITC), A2 (RhBITC) | B1 (FITC), B2 (RhBITC) | C1 (FITC), C2 (RhBITC) | D1 (FITC), D2 (RhBITC) |
|---|---|---|---|---|
| x | 1.05 | 2.11 | 10.55 | 21.10 |
| y | 0.072 | 0.143 | 0.716 | 1.432 |

After 16 hours of reaction, the pH had raised to ~10, so 0.35 g Amberlite IR 120 were added to lower the pH back to 9.00. Once this value was reached, the fluorescent cores mixture was filtered on cotton.

Protocol 6: Silanization Reaction between APTES and Several Infrared Fluorophores Stock solutions of 5 mM Dylight 800-NHS, DY-782 NHS, DY 800-NHS, CF 770-NHS and IRDye 800 CW-NHS were prepared in anhydrous DMSO. Then, 1 μL of APTES was added to 21.44 of these solutions, keeping a $n_{APTES}/n_{dye}$ ratio of 20/1. The tubes were vortexed and left to incubate in the dark at 50° C. for 30 min to complete the coupling reaction.

Figure 25:
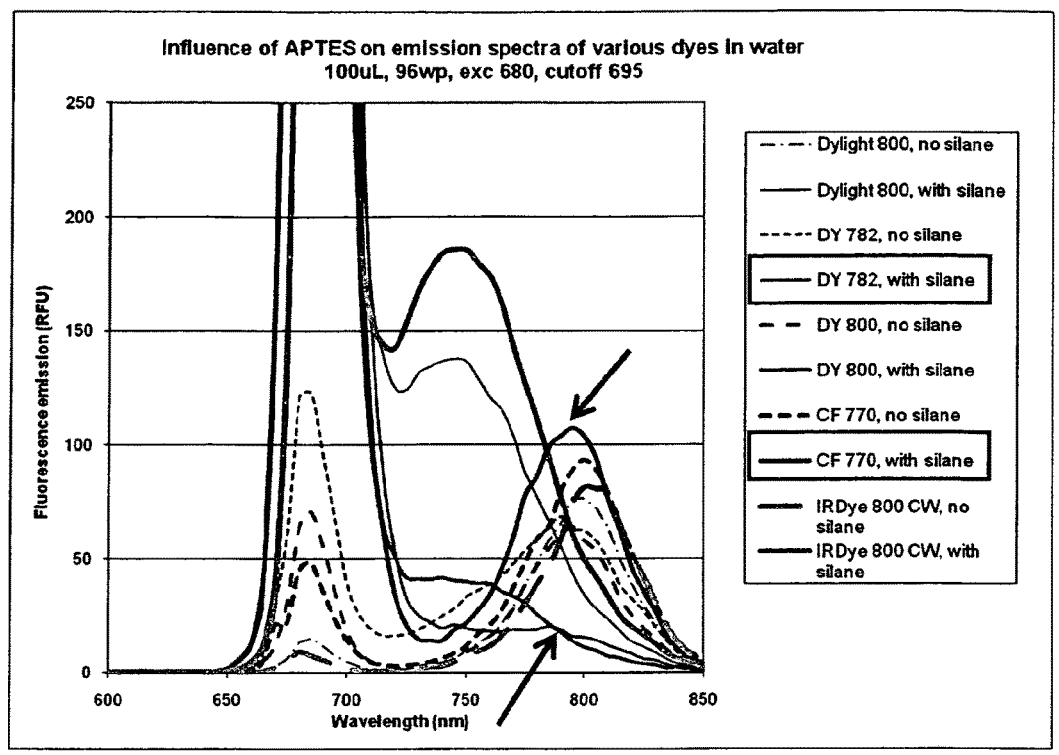
FIG. 25: Emission spectra of several infrared dyes, upon excitation at 680 nm.

Then, 7.4 μL of each reaction mixture were added to 9934 of milliQ water, and the fluorescence spectra of these samples were measured on a spectrophotometer (Spectramax, Molecular Devices), using an excitation wavelength of 680 nm and a cutoff of 695 nm. These spectra are shown on FIG. 25.

Example 2

Steady State Anisotropy Calculations

The calculations of the steady state anisotropy are given in the following equation:

$$r_n = r_{mono} \frac{1 + \left(\frac{R_0}{R}\right)^6}{1 + N\left(\frac{R_0}{R}\right)^6} + r_{et} \frac{(N-1)\left(\frac{R_0}{R}\right)^6}{1 + N\left(\frac{R_0}{R}\right)^6}$$

The relation between the anisotropy $r_n$ and the polarization P, is given by the following equation:

$$P = \frac{3r_n}{2 + r_n}$$

N is the number of dimers in the nanoparticles.

rmono is the steady state anisotropy for one fluorophore when the energy transfer between two dyes goes down to zero.

$r_{et}$ is the theoretical minimum value if the energy transfer is equal 100% between dyes. $r_{et}$ is equal to 0.016.

R is the distance between donor and acceptor.

$R_0$ is the Förster distance at which the energy transfer efficiency is 50% and given by the equation:

$$K^2 = (\cos\theta - 3\cos^2\beta)^2$$

In our case, Q is the quantum field of the fluorophore in the nanoparticles.

n is the refractive index of the silica assumed equal to 1.475, $K^2$ the orientation factor of the fluorophore. $K^2=2/3$ is often assumed. This value is obtained when both dyes can be considered to be isotropically oriented during the excited state lifetime.

J is the spectral overlap integral between the absorption and the emission spectra of the dyes.

Figure 4:
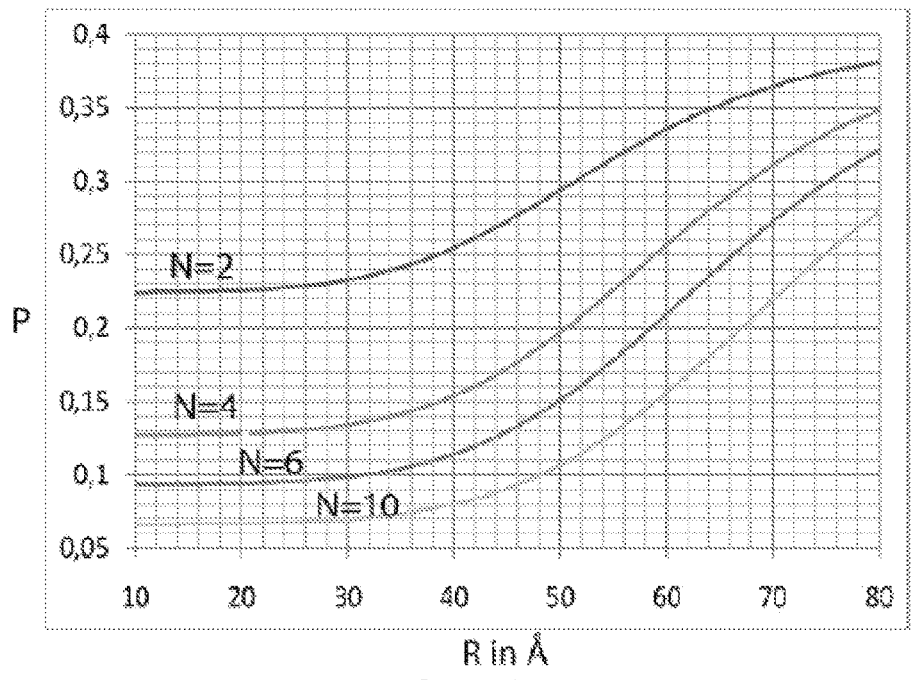
FIG. 4: Steady state polarization versus interfluorophore distance R and the number of dimers in nanoparticles of $R_0=55$ Å in silica nanoparticles.

The FIG. 4 describes the steady state versus the inter fluorophore distance R, and the number N of dimers if the Förster distance $R_0$ is equal to 5.5 nm.

Based on the theoretical simulation, we can approach the number of fluorescent molecules per bead of certain size, necessary to drop down the FP signal around 50 mP. A good working range is shown to be 20 molecules in 15 nm diameter nanoparticles. 15 nm size particles are accessible by the silicate route synthesis. And including 20 molecules in the beads, mean that we will get enough clusters (>4) for all the beads especially if we consider the distribution of molecules through the particles as following the Poisson distribution. And the mean the distance between clusters will be in average around 4.4 nm that's around $0.8 \times R_0$ (the best compromise between FRET and self quenching).

The measurements of the steady intensity It and of the state polarization P are made by a multispectral confocal fluorescence microscope by the following equations:

$$I_t = I_{par} + 2I_{per}$$

$$P = \frac{I_{par} - I_{per}}{I_{par} + I_{per}}$$

with Ipar and Iper being the emission parallel and perpendicular respectively to the excitation polarization direction Example 3

Calculation of the Mean Distance between Fluorophores in Nanoparticles as a Function of the Particles Size and the Number of Fluorescent Molecules The table presented in FIG. 5 presents the mean distance between fluorophores in nanoparticles as a function of particles size and number of dyes per particle.

The shadowed zone comprises distances lower than the Förster distance $R_0$ but higher than the quenching distance, that enable FRET effect to take place. This table gives the experimental conditions for this to happen: the radius of the nanoparticles has to be between 6 and 10 nm, and the dye content must be between 15 and 22 molecules per particle. Based on this, it is now possible to set the amount of dye to add in the synthesis, and the growth protocol to use.

Example 4

Polarization/Intensity 2D encoding Study

Studying the multiplexing capability of the system demonstrated the relation between the intensity and the polarization together, are not linear with the concentration of the corresponding dye. The explanation lies in the following equations:

Mixture of free and bound dye (FP; I)=$f(c_f; c_b)$ $$I = \varepsilon'_f \cdot c_f + \varepsilon'_b \cdot c_b$$

$$P = \frac{P_{min} \cdot \varepsilon'_f \cdot c_f + P_{max} \cdot \varepsilon'_b \cdot c_b}{\varepsilon'_f \cdot c_f + \varepsilon'_b \cdot c_b}$$

$$\varepsilon' = 2,3\varepsilon \cdot l \cdot c \cdot \phi \cdot k \cdot P_o$$

I is the fluorescent intensity, P is the fluorescence polarization, $c_f$ and $c_b$ are the concentrations of free and bound dye, l is the optical length of the sample, E is the extinction coefficient of the dye, $\phi$ is the quantum yield and k is a factor.

The plot illustrating the bi-dimensional coding obtained by mixing two kinds of material having high FP and low FP demonstrate that the error coming from solution handling (pipetting), is affecting a lot the resolution of the discrete code generated. To improve the resolution, we propose to do the synthesis of intermediate FP values nanoparticles that will be just diluted to create the different levels in intensity. Two closest FP nanoparticles can be combined to get an intermediate FP level, with lower deviation.

Figure 6:
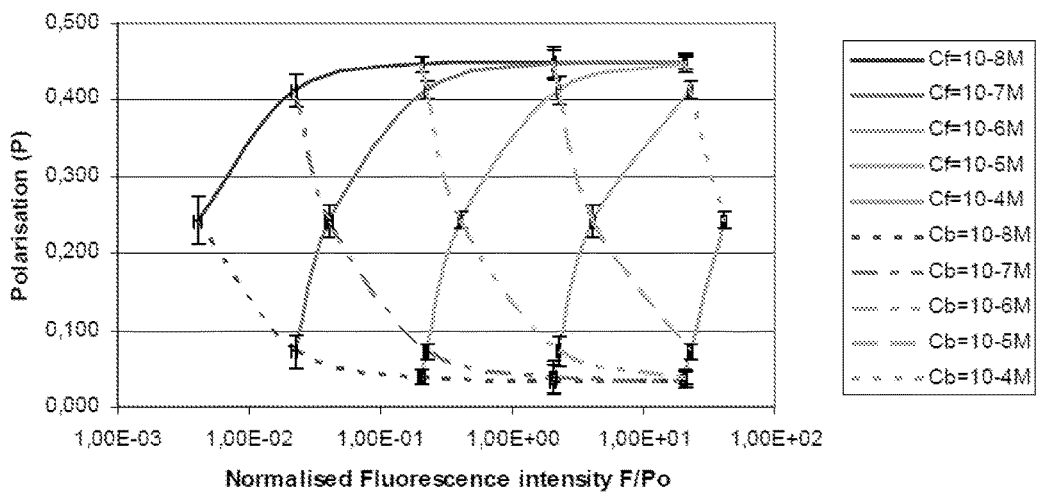
FIG. 6: Fluorescence Intensity—Polarization mapping by varying beads and fluorescein concentration.

FIG. 6 represents the fluorescence intensity/polarization mapping by varying fluorescein in nanoparticles and free fluorescein concentrations.

Example 5

Nanoparticles Characterizations

1. Size Characterization of the Nanoparticles

Figure 7:
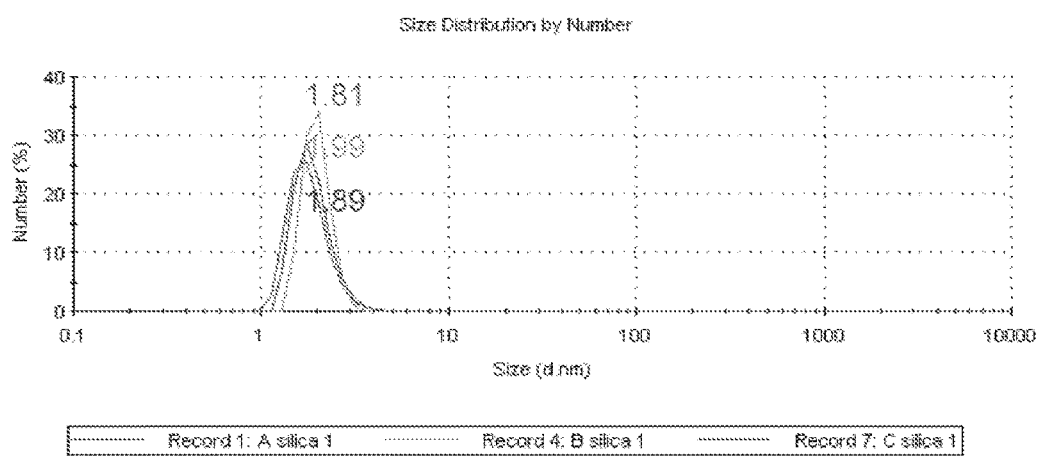
FIG. 7: Size distribution by number: influence of the dye loading on the final diameter of the nanoparticles.

Silica nanoparticles size distribution is measured by dynamic light scattering. Results are provided on FIG. 7. The nanoparticles were prepared by silicate condensation following the protocol 5. The size is independent of the dye concentration. These nanoparticles are especially small, and were never described earlier within this size range.

Figure 8:
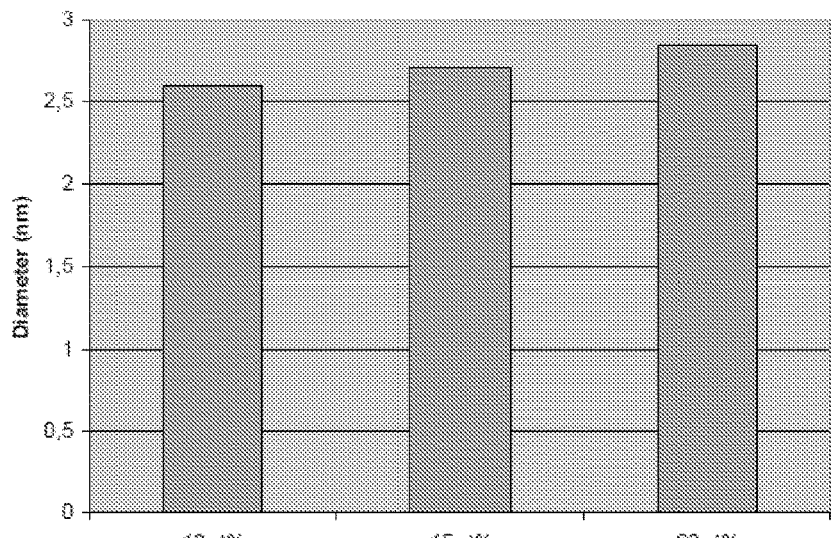
FIG. 8: Influence of silica wt percentage on final diameter.

2. Study of the Effect of the Initial Silicate Concentration on the Particles Size:

Results of this study are presented on FIG. 8. The initial silicate concentration effect on the particles size, following the protocol 4 seems not to change drastically the final particle size, which stays between 2.5 nm and 3 nm.

3. Manual Layer-by-layer Growth of SNPs by Successive Silicate Additions

Figure 9:
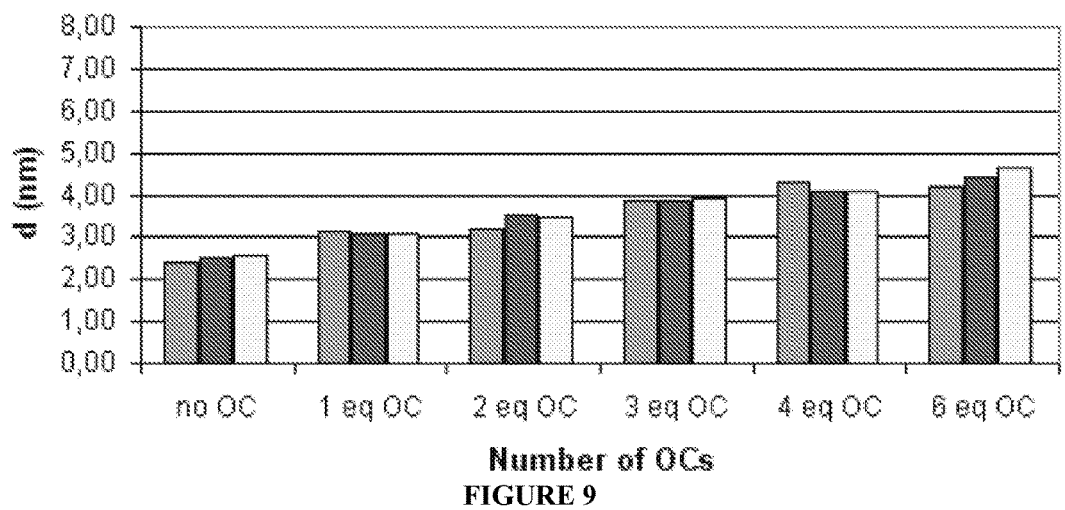
FIG. 9: Evolution of particle size upon successive overcoatings, measured by double exponential fit.

FIG. 9 presents the evolution of particles size measured by double exponential fit in function of the number of overcoatings (OCs).

The silica nanoparticles were grown using the layer by layer method described in the protocol 3.

The dynamic light scattering measurements affords the size characterization and demonstrate the increase of the particles diameter, from 2.5 nm to 4.5 nm as a function of the number of silicate equivalents that was added. It is a significant increase considering the repeatability of the experiments, and the continuity of the data.

Figure 10:
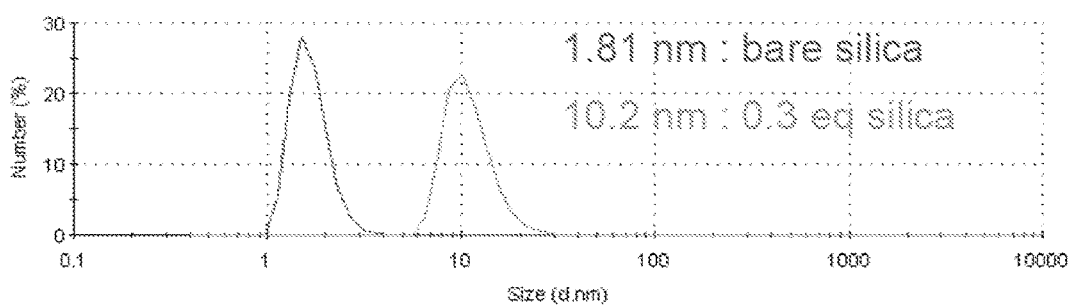
FIG. 10: Size distribution by number of particles: influence of the amount of silicate added for overcoating on the final particle size.

We demonstrate also that we can grow the nanoparticles using the protocol 3 up to 10 nm without affecting the polydispersity. As an example, FIG. 10 compares the polydispersity of nanoparticles with different number of OCs and thus different diameters by dynamic light scattering. The polydispersity is not affected by the diameter increase.

Nevertheless, as the growth is not linear with the silicate weight added (the diameter is proportional to (silicate mass/density)^(1/3)), more than 60 additions are necessary to reach 20 nm particles size by using this protocol. An automated system would be useful for such sizes.

4. Quantum Yield and FP Properties (2.5 Nm Diameter Particles)

Nanoparticles were synthesised according to protocol 5.

Figure 11:
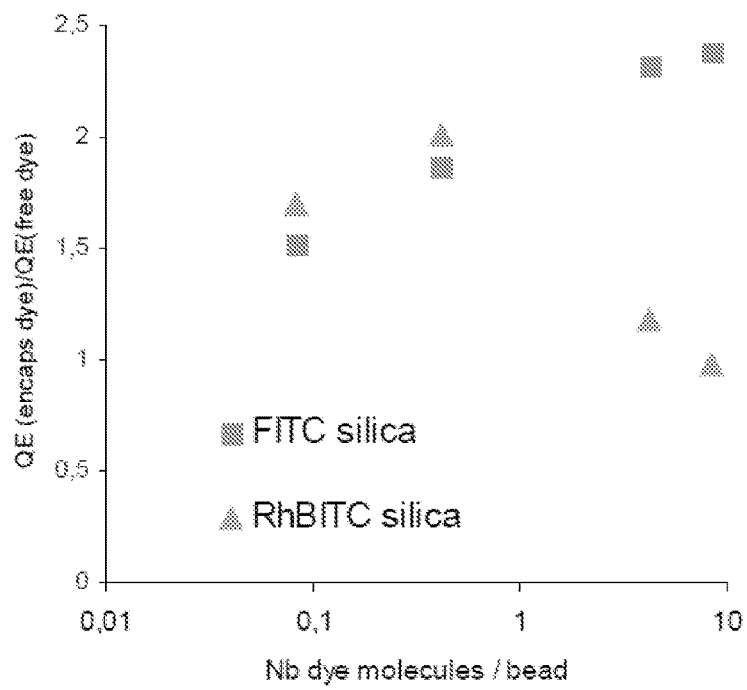
FIG. 11: Brightness ratios of the silica nanoparticles as a function of their fluorophore concentration.
Figure 12:
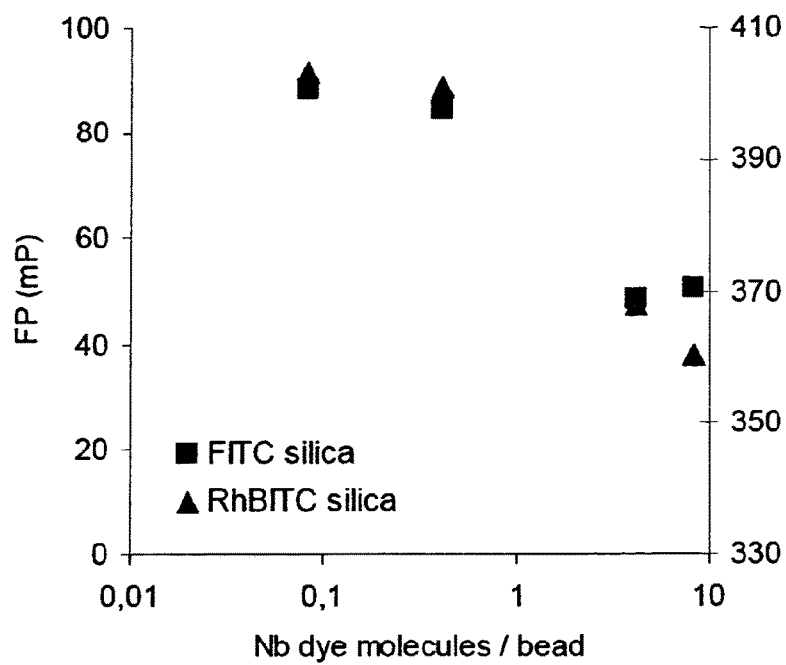
FIG. 12: Fluorescence polarization at maximum emission wavelength of 2.5 nm diameter particles as a function of their fluorophore concentration.

The absorbance and fluorescence spectra were measured on a UV-vis spectrophotometer (Spectramax E5, Molecular Devices), as well as the FP value at maximum emission wavelength. The brightness ratios and FP values of each sample are plotted on FIG. 11 and FIG. 12.

In this preliminary study we demonstrate also for these tiny nanoparticles that we can observe an enhancement of the fluorescence brightness (increase of the quantum yield efficiency compare to the free dye) at least 2 times the free dye, as long as we do not reach the quenching condition (molecules too close from each other).

We demonstrate also an increase of the fluorescence polarization properties, and these properties can be tuned by playing on the number of fluorescent molecule per particles.

5. Emission Spectra of Different Silica Nanoparticles Prepared Using the Protocol 2.

Figure 13:
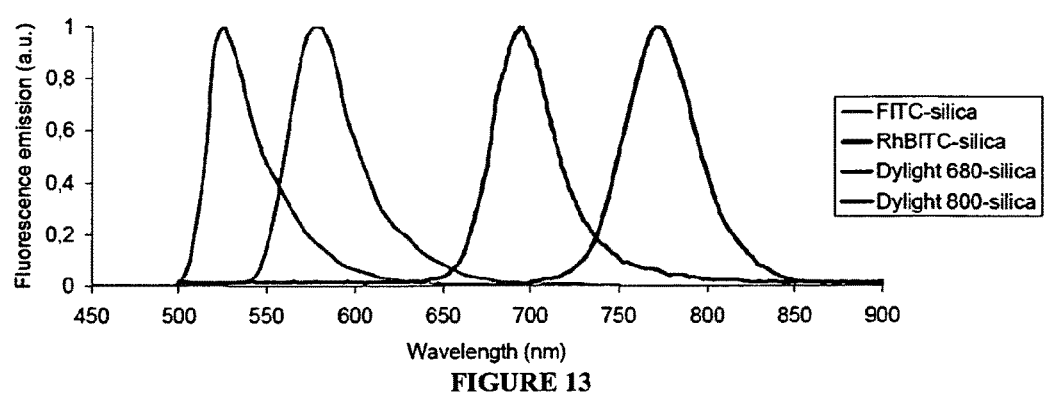
FIG. 13: Emission spectra of different silica nanoparticles prepared using the protocol 1.

FIG. 13 presents the emission spectra of different nanoparticles prepared using protocol 2.

These spectra were measured with a Jobin-Yvon Fluoro; max fluorimeter. A wide range of fluorescent nanoparticles can be prepared using the protocol 2, covering the visible and near infrared spectrum. In the emission spectra on FIG.

13, the FWMH (full-width half-maximum) of the emission signal stays narrow in near IR.

6. Nanoparticles Resistance to Photobleaching.

FIG. 26 presents the photobleaching of dyes prepared using protocol 5, compared to the photobleaching of the equivalent amount of free dye in water.

This experiment was performed by putting 10 uL of sample between glass slide and coverslip, and illuminating them continuously on a Nikon Eclipse Ti microscope with a Nikon Intensilight C-HGFI 100 W lamp. The emitted light was filtered by a bandpass filter, and pictures were recorded at constant time intervals with Nikon NIS elements software.

The pictures were then analyzed with ImageJ software, and for each, the mean intensity was calculated and plotted as a function of time.

This figure shows that the photobleaching is greatly reduced in the case of rhodamine B ITC, and reduced slightly in the case of FITC. This difference is maybe due to the lower purity of the FITC compared to rhodamine B ITC: there is still free FITC, that photobleached faster.

Example 6

Figure 14:
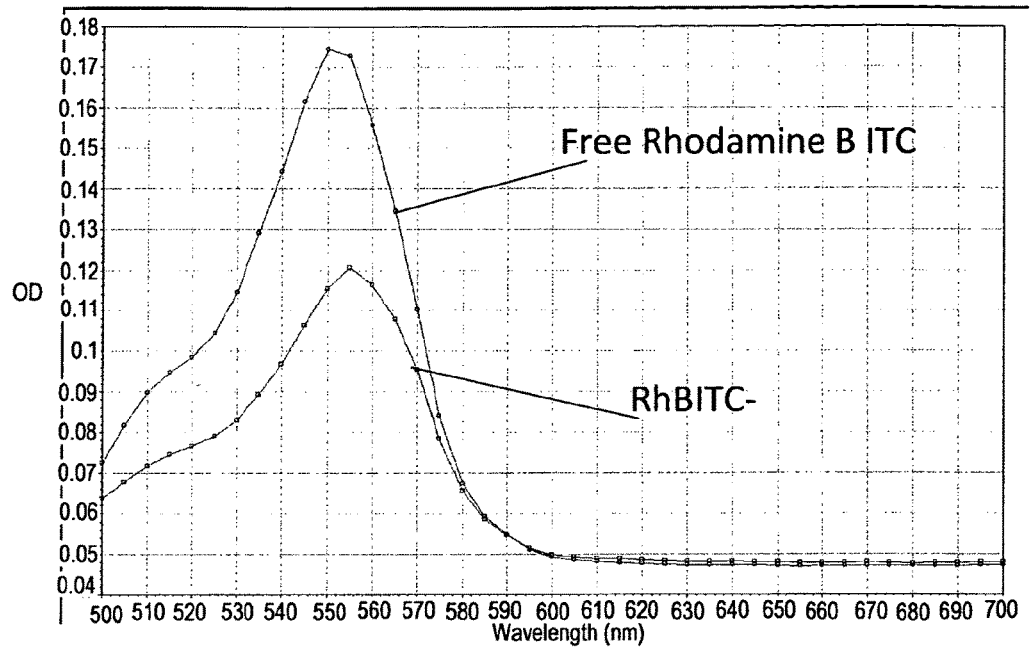
FIG. 14: Absorbance spectra of free and encapsulated rhodamine B ITC.
Figure 15:
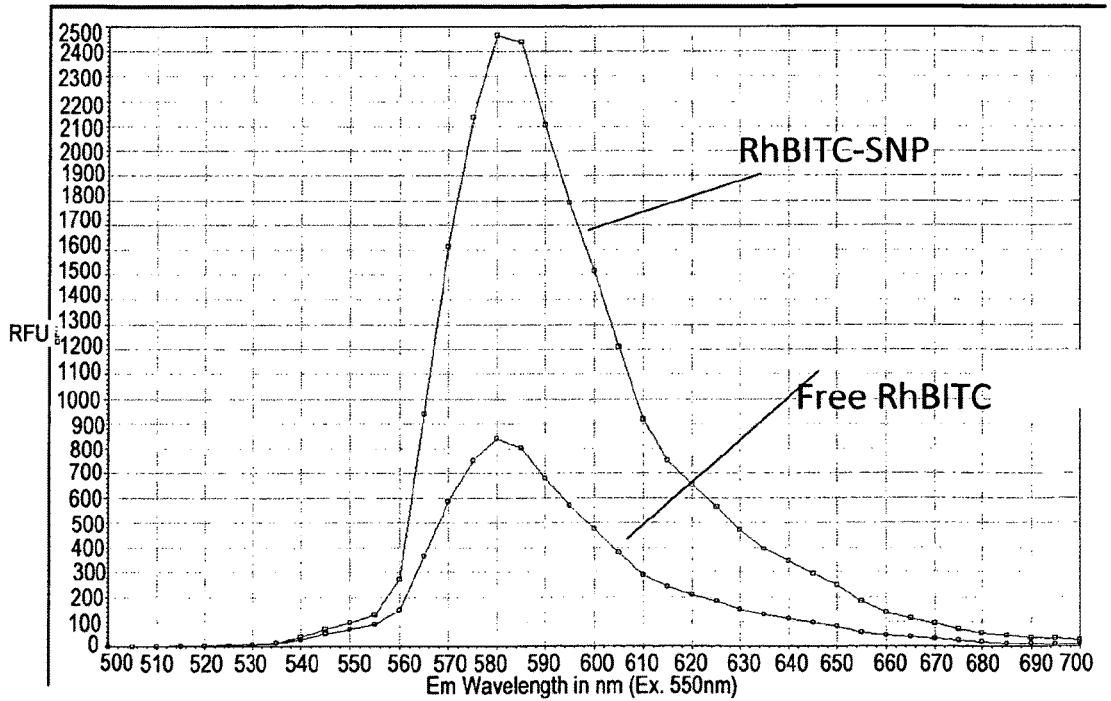
FIG. 15: Fluorescence spectra of free and encapsulated rhodamine B ITC.

Enhancement of Fluorescence of Dyes Embedded in Nanoparticles of the Invention FIGS. 14 and 15 present the absorption and fluorescence spectra of rhodamine B ITC as a free dye and embedded in a silica nanoparticle according to the invention. The nanoparticles are synthesised according to protocol 2. Encapsulation in silica nanoparticle enhances Rhodamine B ITC brightness with a ratio of 5.1. The brightness ratio is defined according to the following formula:

$$\text{brightness} = \frac{\frac{I_{fluo}^{max}(SNP)}{I_{fluo}^{max}(freedye)}}{\frac{I_{abs}^{max}(SNP)}{I_{abs}^{max}(freedye)}}.$$

These spectra compare the absorption and emission properties of the dye in its free form, and after encapsulation in the silica nanoparticles. Both spectra are made with an equivalent fluorophore concentration of 50 µM.

To compare optical performances of the dye in both states, a "brigthness ratio" was defined as above. It means to measure how much more fluorescent encapsulated dyes are, compared to dyes in free form, for an equivalent absorbance maximum.

Figure 16:
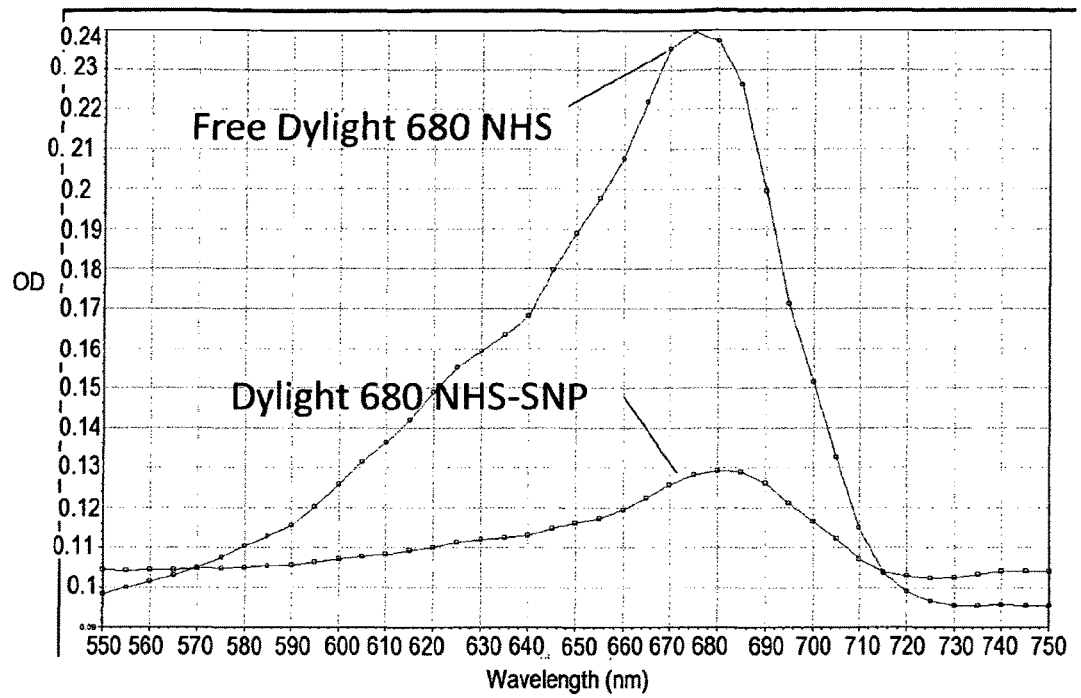
FIG. 16: Absorbance spectra of free and encapsulated Dylight 680-NHS.
Figure 17:
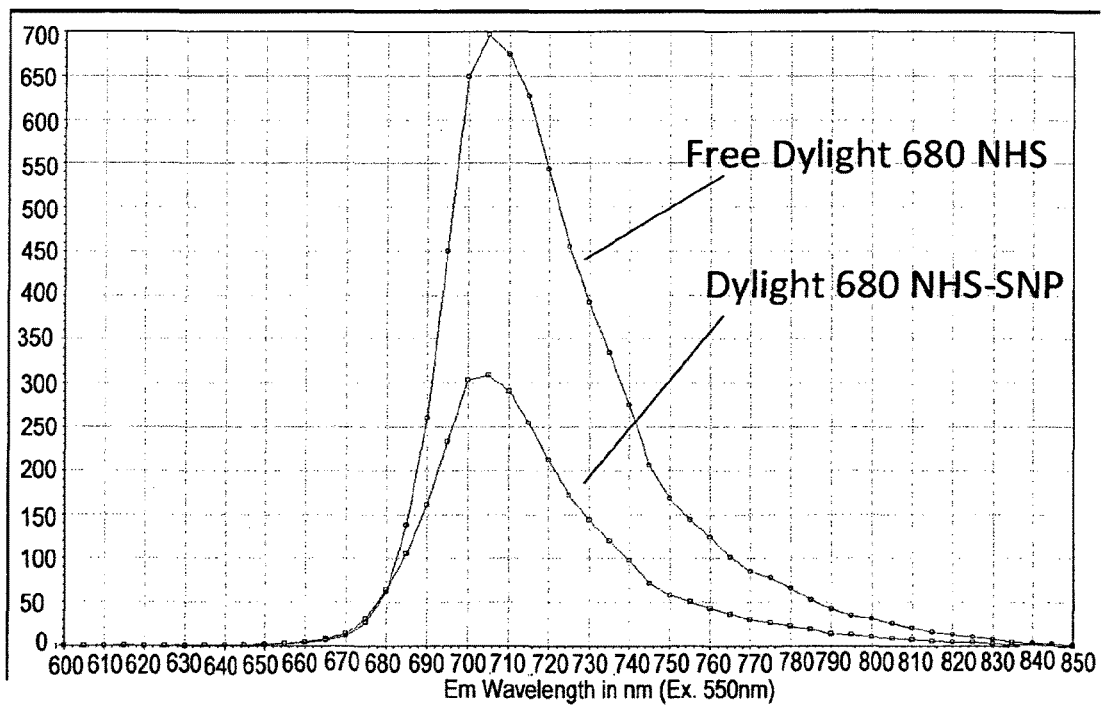
FIG. 17: Fluorescence spectra of free and encapsulated Dylight 680-NHS.

FIGS. 16 and 17 present the absorption and fluorescence spectra of Dylight® 680 NHS as a free dye and embedded in a silica nanoparticle according to the invention. The nanoparticles are synthesised according to protocol 2. Encapsulation in silica nanoparticle enhances Dylight® 680 NHS brightness with a ratio of 1.66.

The lower enhancement compared to the case with rhodamine B may be due to the different nature of the reactive moiety (NHS versus ITC), or to the higher molecular weight of the fluorophore (around 1000 g/mol, compared to 536 g/mol in the case of Rhodamine B ITC).

Example 7

Creation of a 5×5 Optical Barcode Library in Droplets

Among the SNPs synthesized in example 1, protocol 2, the FITC and Dylight 680-coated ones were used to create a 5×5 fluorescent barcode library.

First, each of these 2 color SNPs were diluted in series A to E with borate buffer pH 9.2, by mixing both according to the following table:

| Sample name | A | B | C | D | E |
|---|---|---|---|---|---|
| Dilution factor | 1 | 2 | 4 | 8 | 16 |
| SNP solution volume (uL) | 128 | 64 | 32 | 16 | 8 |
| Borate buffer volume (uL) | 0 | 64 | 96 | 112 | 120 |

FITC solutions were called A1 to E1, Dylight 680 solutions were called A2 to E2

Then, in a 384 well plate, solutions were mixed according to the following table (20 uL of each):

| Well | 1 | | 2 | | 3 | | 4 | | 5 | |
|---|---|---|---|---|---|---|---|---|---|---|
| A | A1 | A1 | B1 | A2 | C1 | A2 | D1 | A2 | E1 | A2 |
| B | A1 | B2 | B1 | B2 | C1 | B2 | D1 | B2 | E1 | B2 |
| C | A1 | C2 | B1 | C2 | C1 | C2 | D1 | C2 | E1 | C2 |
| D | A1 | D2 | B1 | D2 | C1 | D2 | D1 | D2 | E1 | D2 |
| E | A1 | E2 | B1 | E2 | C1 | E2 | D1 | E2 | E1 | E2 |

The plate was sealed with aluminium foil and centrifuged at 1200 rpm during 10 s.

Then, a droplet library of those barcodes was generated by automatically pipetting some content of each well, generating droplets on a microfluidic chip and collecting the total content in a vial. The vial was shaken to homogenize the droplet content, then the droplets were reinjected on-chip.

The droplets were illuminated by 2 lasers, one at 488 nm (Coherent Sapphire 488-20), one at 680 nm (Newport LQC690-30) and their fluorescence signal was simultaneously detected by 2 PMTs, in front of which bandpass filters (Semrock) were installed to get respective detection windows of 531±20 nm (green) and 720±7 nm.

The signal was processed using a FPGA card and Labview (National Instruments) in-house detection software. This detection was performed 3 h and 18 h after the droplet library generation. FIGS. 19 to 24 were plotted using an in-house Labview software.

Figure 19:
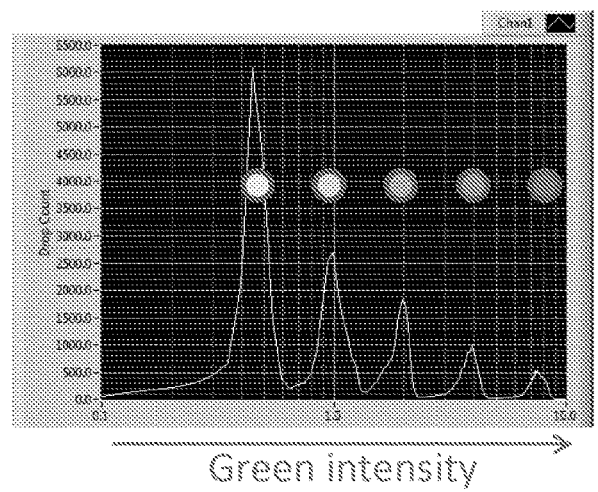
FIG. 19: Histogram of number of droplets in library vs green fluorescence intensity, 3 h after library generation
Figure 20:
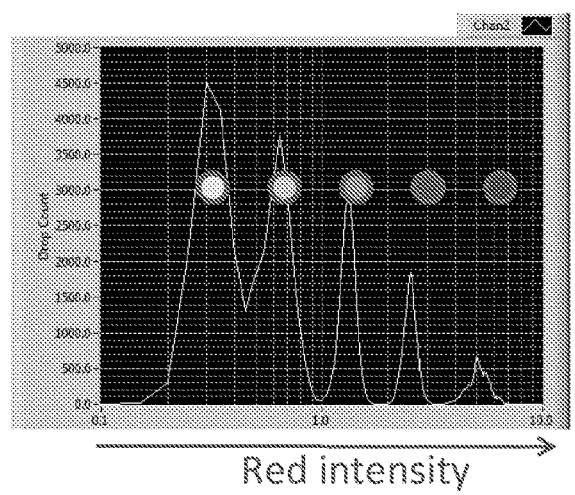
FIG. 20: Histogram of number of droplets in library vs infrared fluorescence intensity, 3 h after library generation.

FIGS. 19 and 20 show 5 distinct peaks for each color, showing that the pipetting was made accurately according to the previous table. The peaks are not split in subpeaks, indicating that all droplets containing the same amount of one dye have the same intensity of that color, independently of the amount of the other dye.

Figure 21:
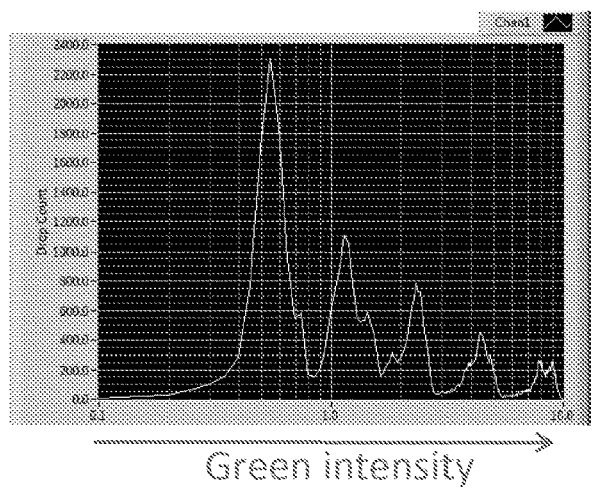
FIG. 21: Histogram of number of droplets in library vs green fluorescence intensity, 18 h after library generation.
Figure 22:
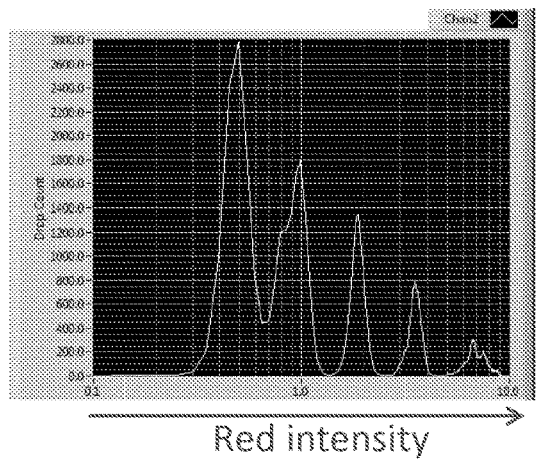
FIG. 22: Histogram of number of droplets in library vs infrared fluorescence intensity, 18 h after library generation.

FIGS. 21 and 22 show that the 5 peaks in each color remain very distinct even after 18 h.

Figure 23:
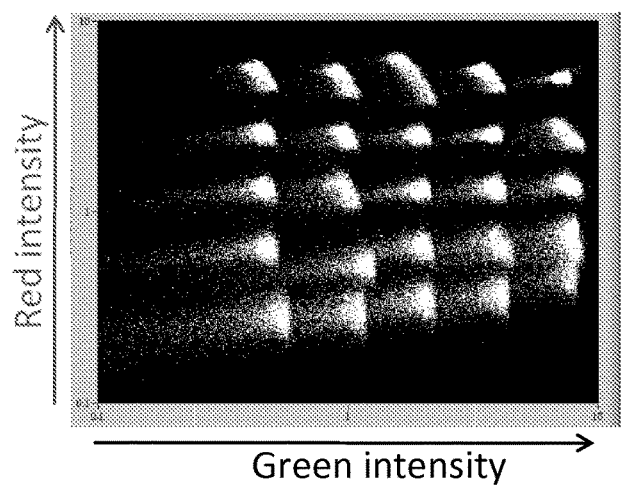
FIG. 23: Scatterplot of red vs green fluorescence intensity of droplet library, 3 h after its generation.

FIG. 23 shows the 25 labels that are distinct and nearly form a square grid, as expected. The slight deviation of the lower line is due to the optical crossover between the dyes, but can be easily circumvented by adjusting concentrations of both colors.

Figure 24:
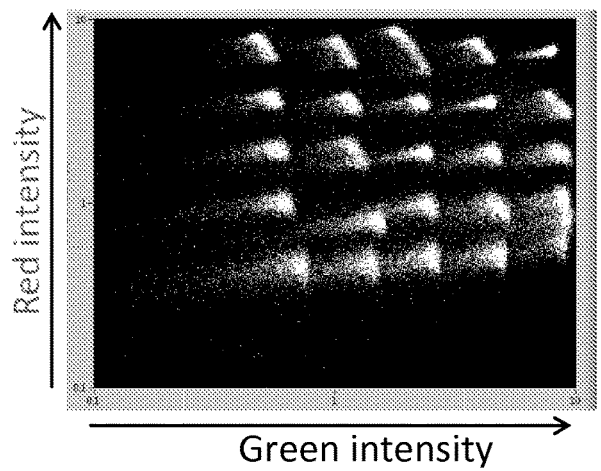
FIG. 24: Scatterplot of red vs green fluorescence intensity of droplet library, 18 h after its generation.

Finally, FIG. 24 shows that the code remains nearly completely inchanged, which shows that the size and content of the droplets did not vary overnight.

The invention claimed is:

1. A nanoparticle comprising:
a nonporous silica core, having a diameter of about 1 nanometer to about 200 nanometers, and comprising a first organic label bound to the silica core, wherein the first organic label is a first fluorescent dye or a first phosphorescent dye;

a silica shell surrounding the silica core, the silica shell comprising a second organic label distinct from the first organic label; and a layer of polyethylene glycol molecules covalently bound to the silica shell.

2. The nanoparticle of claim 1, further comprising a third organic label bound to the core.

3. The nanoparticle of claim 1, wherein the second organic label is a second fluorescent dye or a second phosphorescent dye.

4. The nanoparticle of claim 1, wherein the first organic label is selected from the group consisting of fluoresceine-ITC, Rhodamine B ITC, Dylight 680-NHS, Dylight 800-NHS, CF770 NHS, CF 790 NHS, DY-782-NHS, IRDye 800CW NHS, IRDye 800RS NHS, xanthene, benzo[a]xanthene, benzo[b]xanthene, benzo [c]xanthene, coumarin, benzocoumarin, alizarin, azo, phenoxazine, benzo[a]phenoxazine, benzo[b]phenoxazine, benzo[c]phenoxazine, naphthalimide, naphtho lactam, azolactone, methyne, oxazine, thiazine, diketopyrrolopyrrole, quinacridone, thioepindoline, lactamimide, diphenylmaleimide, acetoacetamide, imidazothiazine, benzanthrone, phthalimide, benzotriazole, pyrimidine, pyrazine, triazine, acridine, oxazine, cyanine, thiazole, anthraquinone, azamethine, polyene, oxonol, benzimidazole, indolenine, Dabcyl, QXL, IRDye QC, QSY, ATT0488, BODIPY FL, DyLight 488, Sodium fluorescein, DY-682, green fluorescent protein (GFP), EGFP, blue fluorescent proteins (EBFP), cyan fluorescent proteins (ECFP), YFP, DsRed, Keima, and a mixture thereof.

5. The nanoparticle of claim 1, wherein the first label is a fluorescent dye.

6. The nanoparticle of claim 1, wherein the nanoparticle has a diameter present of about 1 nanometer to about 25 nanometers.

7. The nanoparticle of claim 6, wherein the nanoparticle has a diameter of between about 2 nanometers and about 15 nanometers.

8. A method for making a nanoparticle of claim 1, comprising the steps of:
(a) providing a first organic label bound to a first molecule comprising silane, thereby forming a silane functionalized label;
(b) providing a first solution comprising free silicon-containing molecules;
(c) mixing the silane functionalized label and the first solution to form a first mixed solution;
(d) reducing the pH of the first mixed solution thereby allowing conditions for the formation of covalent bonds among the silicon-containing molecules to form silica within which the first organic label is covalently bound, thereby nucleating the core; and
(e) allowing sufficient time for the core to grow until stopped.

9. The method of claim 8, wherein step (d) includes adding an ion-exchange resin to the first mixed solution, thereby to reduce the pH.

10. The method of claim 8, wherein the silane comprises APTES, APTMS, MPTMS, or MPTES.

11. The method of claim 8, wherein the method further comprises:
(f) mixing the grown core with a second solution comprising free silicon-containing molecules to form a second mixed solution;
(g) reducing the pH of the second mixed solution thereby growing a shell; and
(h) allowing sufficient time for the shell to grow until stopped.

12. The method of claim 11, wherein the second solution further comprises a second organic label.

13. The method of claim 11, wherein steps (f) through (h) are repeated one or more times, and wherein the second solution comprises an organic label different than the first or preceding organic labels during each repeat.

14. The method of claim 11, further comprising the steps of:
(i) optionally adding a functionalizing agent surrounding the shell to form a functionalized shell; and
(j) tuning one or more properties of the nanoparticle by grafting one or more surface molecules to the shell or, if present to the functionalized shell.

15. The method of claim 14, wherein the functionalizing agent comprises silanes, maleimides, thiols, or amines.

16. The method of claim 14, wherein the surface molecules comprise a polymer, protein, antibody, antigen, sugar, PEG, organic molecule, or enzyme.

17. The method of claim 8, wherein growth of the core or the shell is stopped by depletion of a constituent, addition of a quenching reagent, changing temperature, or changing pH.

18. A method of detecting a biological entity, comprising the steps of:
(a) attaching a nanoparticle of claim 1 to the biological entity; and
(b) detecting the first organic label.

19. The method of claim 2, wherein the third organic label is a third fluorescent dye or a third phosphorescent dye.

* * * * *